US010736935B2

(12) United States Patent
Watnick

(10) Patent No.: US 10,736,935 B2
(45) Date of Patent: \*Aug. 11, 2020

(54) SAPOSIN-A DERIVED PEPTIDES AND USES THEREOF

(71) Applicant: Children's Medical Center Corporation, Boston, MA (US)

(72) Inventor: Randolph S. Watnick, Newton, MA (US)

(73) Assignee: CHILDREN'S MEDICAL CENTER CORPORATION, Boston, MA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 14/367,577

(22) PCT Filed: Dec. 21, 2012

(86) PCT No.: PCT/US2012/071424
§ 371 (c)(1),
(2) Date: Jun. 20, 2014

(87) PCT Pub. No.: WO2013/096868
PCT Pub. Date: Jun. 27, 2013

(65) Prior Publication Data
US 2015/0320825 A1     Nov. 12, 2015

Related U.S. Application Data

(60) Provisional application No. 61/579,095, filed on Dec. 22, 2011.

(51) Int. Cl.
| | | |
|---|---|---|
| *A61K 38/08* | (2019.01) | |
| *C07K 7/06* | (2006.01) | |
| *C07K 5/113* | (2006.01) | |
| *C07K 16/00* | (2006.01) | |
| *A61K 38/07* | (2006.01) | |
| *A61K 39/395* | (2006.01) | |
| *G01N 33/50* | (2006.01) | |
| *C12Q 1/6886* | (2018.01) | |
| *G01N 33/74* | (2006.01) | |
| *G01N 33/68* | (2006.01) | |
| *G01N 33/574* | (2006.01) | |
| *C07K 5/11* | (2006.01) | |
| *A61K 45/06* | (2006.01) | |
| *C07K 14/475* | (2006.01) | |
| *A61K 39/00* | (2006.01) | |
| *A61K 38/00* | (2006.01) | |

(52) U.S. Cl.
CPC .............. *A61K 38/08* (2013.01); *A61K 38/07* (2013.01); *A61K 39/39591* (2013.01); *A61K 45/06* (2013.01); *C07K 5/1019* (2013.01); *C07K 5/1021* (2013.01); *C07K 7/06* (2013.01); *C07K 14/475* (2013.01); *C07K 16/00* (2013.01); *C12Q 1/6886* (2013.01); *G01N 33/5023* (2013.01); *G01N 33/574* (2013.01); *G01N 33/6893* (2013.01); *G01N 33/74* (2013.01); *A61K 38/00* (2013.01); *A61K 2039/505* (2013.01); *C07K 2319/30* (2013.01); *C07K 2319/31* (2013.01); *C12Q 2600/106* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,696,080 A | 12/1997 | O'Brien et al. | |
| 5,700,909 A | 12/1997 | O'Brien | |
| 5,714,459 A | 2/1998 | O'Brien et al. | |
| 6,500,431 B1 * | 12/2002 | Gill .................... | C07K 14/475 424/184.1 |
| 7,166,691 B2 | 1/2007 | Koochekpour et al. | |
| 7,341,730 B1 | 3/2008 | Gill | |
| 2002/0177551 A1 | 11/2002 | Terman | |
| 2003/0211521 A1 * | 11/2003 | Taylor-Papadimitriou .................. | C07K 14/4748 435/6.14 |
| 2004/0120961 A1 | 6/2004 | Koochekpour et al. | |

(Continued)

FOREIGN PATENT DOCUMENTS

| | | |
|---|---|---|
| WO | WO 95/03821 A1 | 2/1995 |
| WO | WO 00/02902 A1 | 1/2000 |

(Continued)

OTHER PUBLICATIONS

PeptideAtlas, p. 1, Sep. 16, 2019.*

(Continued)

*Primary Examiner* — Alana Harris Dent
(74) *Attorney, Agent, or Firm* — Foley & Lardner LLP

(57) ABSTRACT

Disclosed herein are polypeptides and fusion polypeptides that have anti-angiogenic activity that can be used to inhibit tumor growth and tumor metastasis. The polypeptide consists of 9 or less consecutive amino acid residues (e.g., 8, 7, 6, 5, or 4) comprising the active core amino acid sequence DWLP, or an amino acid substitution variant thereof. Specific amino acid substitutions are disclosed herein. In some embodiments, the peptide consists essentially of 4-6 mers identified as exhibiting the activity of prosaposin A. Also disclosed herein are therapeutic compositions comprising the polypeptides and fusion polypeptides, and their use in the treatment, prevention, and inhibition of angiogenesis-related diseases and disorders such as cancer and cancer metastasis.

14 Claims, 23 Drawing Sheets

Specification includes a Sequence Listing.

(56) References Cited

U.S. PATENT DOCUMENTS

| | | | |
|---|---|---|---|
| 2004/0175361 | A1 | 9/2004 | Blaschuk et al. |
| 2004/0229799 | A1 | 11/2004 | Qi |
| 2006/0275274 | A1 | 12/2006 | Onichtchouk et al. |
| 2007/0099251 | A1 | 5/2007 | Zhang et al. |
| 2009/0163410 | A1 | 6/2009 | Baty et al. |
| 2009/0269373 | A1 | 10/2009 | Qi |
| 2010/0144025 | A1 | 6/2010 | Miyakawa et al. |
| 2010/0144603 | A1 | 6/2010 | Watnick |
| 2011/0271357 | A1* | 11/2011 | Kim ................. G01N 33/57419 800/13 |
| 2013/0072425 | A1 | 3/2013 | Watnick |
| 2014/0113310 | A9* | 4/2014 | Skolnick .......... G01N 33/57434 435/7.4 |
| 2016/0033513 | A1 | 2/2016 | Watnick |

FOREIGN PATENT DOCUMENTS

| | | |
|---|---|---|
| WO | WO 02/24952 A1 | 3/2002 |
| WO | WO-2004/048411 | 6/2004 |
| WO | WO 2004/084930 A1 | 10/2004 |
| WO | WO 2004/096159 A2 | 11/2004 |
| WO | WO-2005/038000 | 4/2005 |
| WO | WO 2005/073374 A1 | 8/2005 |
| WO | WO-2006/062776 | 6/2006 |
| WO | WO 2007/047796 A2 | 4/2007 |
| WO | WO 2007/047796 A3 | 4/2007 |
| WO | WO 2007/066018 A2 | 6/2007 |
| WO | WO 2009/002931 A2 | 12/2008 |
| WO | WO-2010/090756 | 8/2010 |
| WO | WO 2010/105256 A1 | 9/2010 |
| WO | WO-2011/084685 | 7/2011 |
| WO | WO 2011/084685 A2 | 7/2011 |
| WO | WO-2012/021786 | 2/2012 |

OTHER PUBLICATIONS

Peptide Database Search Results, p. 1, Sep. 16, 2019.*
Peptide Atlas database, SEQ ID No. 5, 3 sheets, Mar. 27, 2020.*
Clezardin et al., Expression of thrombospondin (TSP1) and its receptors (CD36 and CD51) in normal, hyperplastic, and neoplastic human breast. Cancer Res. Mar. 15, 1993;53(6):1421-30.
Febbraio et al., CD36: a class B scavenger receptor involved in angiogenesis, atherosclerosis, inflammation, and lipid metabolism. J Clin Invest. Sep. 2001;108(6):785-91.
Simantov et al., CD36: a critical anti-angiogenic receptor. Front Biosci. Sep. 1, 2003,;8:s874-82.
Dawson et al., CD36 mediates the In vitro inhibitory effects of thrombospondin-1 on endothelial cells. J Cell Biol. Aug. 11, 1997;138(3):707-17.
Dooley et al., "Selective ligands for the mu, delta, and kappa opioid receptors identified from a single mixture based tetrapeptide positional scanning combinatorial library", The Journal of Biological Chemistry, 1998, 11 pages.
Moriyama et al., "CA homolog of mammalian PRL-releasing peptide (fish arginyl-phenylalanyl-amide peptide) is a major hypothalamic peptide of PRL release in teleost fish", Endocrinology, 2002, 9 pages.
Examination Report for Australian Application No. 2012358269 dated Sep. 19, 2017, 4 pages.
Examination Report for Australian Application No. 2012358269 dated Oct. 11, 2017, 7 pages.
[No Author Listed] Myc and Human cancer database. John Hopkins University School of medicine & john hopkins health system. Last updated Apr. 14, 2013. Last accessed at http://www.myccancergene.org/site/cancerDB.asp?PageID=1 on Jul. 15, 2013.
Campana et al., Secretion of prosaposin, a multifunctional protein, by breast cancer cells. Biochim Biophys Acta. May 24, 1999;1427(3):392-400.
De Fraipont et al., Expression of the angiogenesis markers vascular endothelial growth factor-A, thrombospondin-1, and platelet-derived endothelial cell growth factor in human sporadic adrenocortical tumors: correlation with genotypic alterations. J Clin Endocrinol Metab. Dec. 2000;85(12):4734-41.
Doll et al., Thrombospondin-1, vascular endothelial growth factor and fibroblast growth factor-2 are key functional regulators of angiogenesis in the prostate. Prostate. Dec. 1, 2001;49(4):293-305.
Genbank Submission; NIH/NCBI, Accession No. EAW54436. Venter et al., Dec. 18, 2006. 3 pages.
Gopalakrishnan et al., Purified recombinant human prosaposin forms oligomers that bind procathepsin D and affect its autoactivation. Biochem J. Nov. 1, 2004 ;383(Pt. 3):507-15.
Hu et al., Prosaposin down-modulation decreases metastatic prostate cancer cell adhesion, migration, and invasion. Mol Cancer. Feb. 4, 2010;9:30.
Kalas et al., Oncogenes and Angiogenesis: down-regulation of thrombospondin-1 in normal fibroblasts exposed to factors from cancer cells harboring mutant ras. Cancer Res. Oct. 1, 2005;65(19):8878-86.
Kang et al., Prosaposin inhibits tumor metastasis via paracrine and endocrine stimulation of stromal p53 and Tsp-1. Proc Natl Acad Sci U S A. Jul. 21, 2009;106(29):12115-20. Epub Jul. 6, 2009. Erratum in: Proc Natl Acad Sci U S A. Sep. 8, 2009;106(36):15513.
Koochekpour et al., Prosaposin is an AR-target gene and its neurotrophic domain upregulates AR expression and activity in prostate stromal cells. J Cell Biochem. Aug. 15, 2008;104(6):2272-85.
Koochekpour et al., Amplification and overexpression of prosaposin in prostate cancer. Genes Chromosomes Cancer. Dec. 2005;44(4):351-64.
Koochekpour et al., Prosaposin is a novel androgen-regulated gene in prostate cancer cell line LNCaP. J Cell Biochem. Jun. 1, 2007;101(3):631-41.
Koochekpour, PSAP (prosaposin (variant Gaucher disease and variant metachromatic leukodystrophy)). Atlas Genet Cytogenet Oncol Haematol. 2007;11(1):12-18.
Lee et al., Saposin C promotes survival and prevents apoptosis via PI3K/Akt-dependent pathway in prostate cancer cells. Mol Cancer. Nov. 17, 2004;3:31.
Morimoto et al., Saposin A: second cerebrosidase activator protein. Proc Natl Acad Sci U S A. May 1989;86(9):3389-93.
O'Brien et al., Coding of two sphingolipid activator proteins (SAP-I and SAP-2) by same genetic locus. Science. Aug. 26, 1988;241(4869):1098-101.
O'Brien et al., Saposin proteins: structure, function, and role in human lysosomal storage disorders. FASEB J. Mar. 1, 1991;5(3):301-8.
Panigone et al., Up-regulation of prosaposin by the retinoid HPR and the effect on ceramide production and integrin receptors. FASEB J. Jun. 2001;15(8):1475-7.
Qi et al., Functional human saposins expressed in *Escherichia coli*. Evidence for binding and activation properties of saposins C with acid beta-glucosidase. J Biol Chem. Jun. 17, 1994;269(24):16746-53.
Vogelstein et al., p53: The most frequently altered gene in human cancers. Nature education. 2010;3(9):6. Last accessed at http://www.nature.com/scitable/topicpage/p53-the-most-frequently-altered-gene-in-14192717 on Jul. 15, 2013.
Yabkowitz et al., Motility of human carcinoma cells in response to thrombospondin: relationship to metastatic potential and thrombospondin structural domains. Cancer Res. Jan. 15, 1993;53(2):378-87.
Examination Report for AU 2012358269 dated Oct. 25, 2016.
U.S. Appl. No. 14/773,596, filed Sep. 8, 2015, Watnick.
EP 12859931.3, Apr. 6, 2016, Supplementary European Search Report.
PCT/US2014/026546, Jul. 28, 2014, International Search Report and Written Opinion.
PCT/US2014/026546, Sep. 24, 2015, International Report on Patentability.
PCT/US2015/022745, May 29, 2015, Invitation to Pay Additional Fees.

(56) References Cited

OTHER PUBLICATIONS

PCT/US2015/022745, Aug. 12, 2015, International Search Report and Written Opinion.
U.S. Appl. No. 15/128,617, filed Sep. 23, 2016, Watnick.

* cited by examiner

"-"=untreated
"LN4"=PC3M-LN4 conditioned media (metastatic cells)
"PC3"=PC3 conditioned media (non-metastatic cells)

Lung Fibroblasts

1. CDWLPK (SEQ ID NO: 3)
2. DWLPK (SEQ ID NO: 4)
3. DWLP (SEQ ID NO: 5)
4. DWL
5. WLPK (SEQ ID NO: 45)
6. LPK

Lung Tissue 4-day treatment 20mg/kg daily i.p.

1. DWLP (SEQ ID NO: 5)
2. AWLP (SEQ ID NO: 124)
3. DALP (SEQ ID NO: 125)
4. DWAP (SEQ ID NO: 6)
5 DWLA (SEQ ID NO: 126)

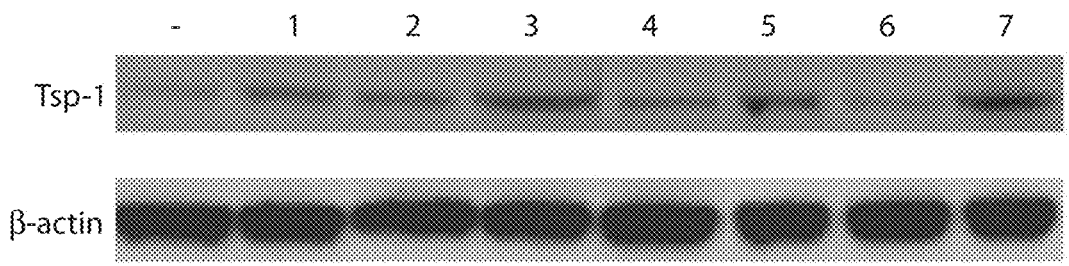
1. DWLPK (SEQ ID NO: 4)
2. EWLPK (SEQ ID NO: 127)
3. DYLPK (SEQ ID NO: 7)
4. DWIPK (SEQ ID NO: 128)
5. DWVPK (SEQ ID NO: 8)
6. DWMPK (SEQ ID NO: 129)
7. DWLPR (SEQ ID NO: 9)
Fig. 5
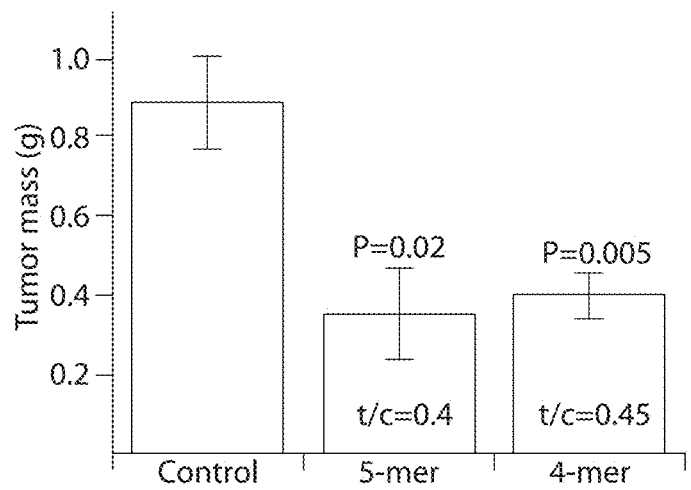
Injected 2x10⁶ PC3M-LN4 cells orthotopically in prostate gand, after 26 days treatment commenced with 4- and 5- amino acid peptides at 30mg/kg/day for 16 days at which point the mice were sacrificed.
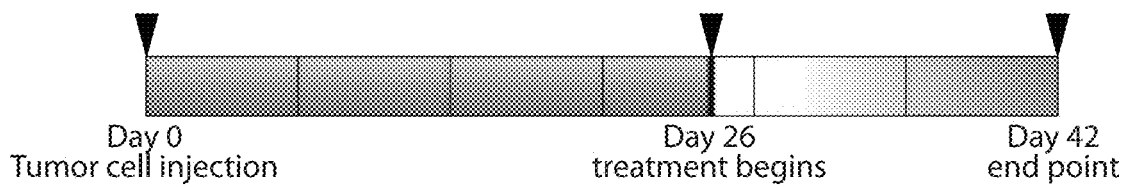
Fig. 6

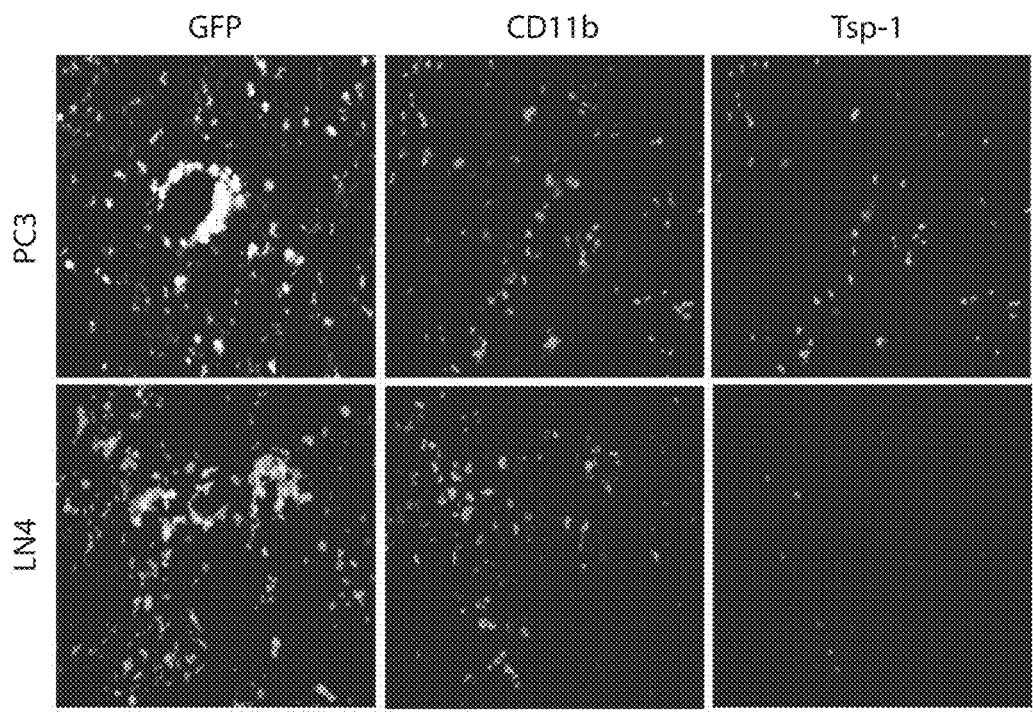
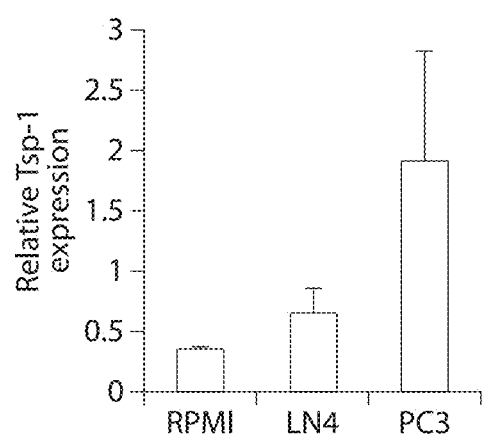
Fig. 12

| Tissue Category | No | Mean SI[1] | P-value[2] |
|---|---|---|---|
| Prostate Hyperplasia[3] | 41 | 8.9 | <0.0005 |
| Localized Carcinoma | 104 | 6.1 | |
| Castration Resistant Carcinoma | 33 | 5.9 | |
| Skeletal Metastasis[4] | 13 | 4.4 | 0.023 |
| Non-Skeletal Metastasis | 28 | 5.2 | |
| Total | 219 | | <0.0005 |

[1]Prosaposin expression, SI; Staining Index (range 0-9)
[2]Kruskal-Wallis test
[3]All carcinoma groups significantly lower than hyperplasia
[4]Skeletal metastasis lowest among carcinomas

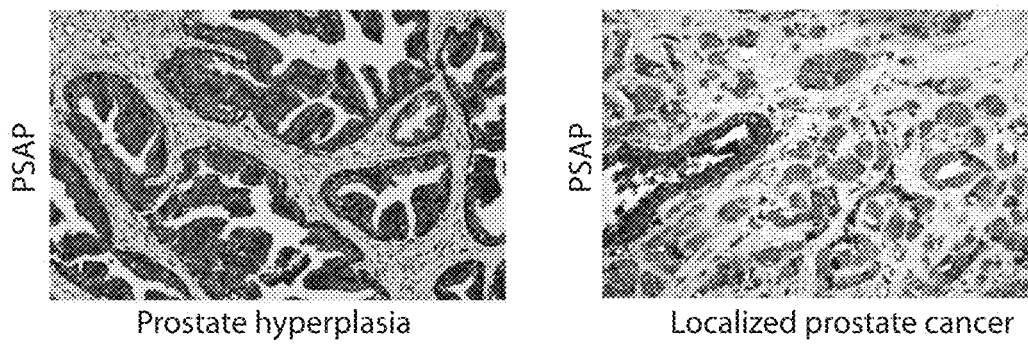

Prostate hyperplasia     Localized prostate cancer

Skeletal Metastasis

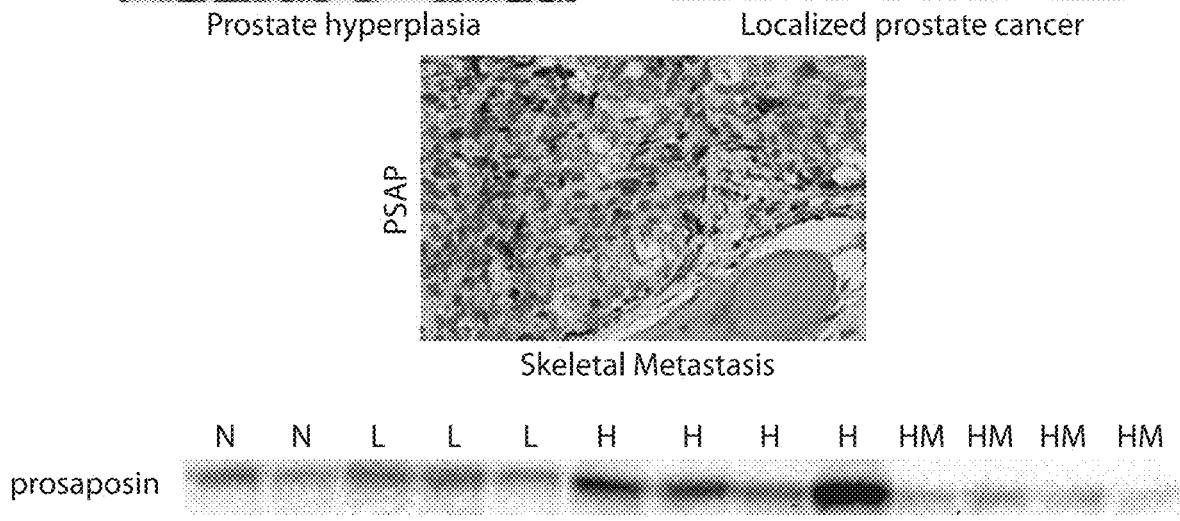

Colorectal Cancer Patient Serum

N = normal patients (no cancer)
L = low grade CRC ($T_{1/2}M_0$)
H = high grade CRC ($T_3M_0$)
HM = high grade CRC with metastases ($T_{3/4}M_0$)

Fig. 13

| Variables | No | Hazard ratio | 95% CI | P* |
|---|---|---|---|---|
| Clinical recurrence | | | | |
| Gleason score† | | | | 0.001 |
| ≤3+4 | 42 | 1.0 | | |
| ≥4+3 | 55 | 4.6 | 1.6-13.2 | |
| Pathological stage‡ | | | | ns |
| pT2 | 29 | 1.0 | | |
| ≥PT3 | 68 | 1.9 | 0.6-5.6 | |
| Preoperative s-PSA§ | | | | ns |
| ≤20 ng/ml | 72 | 1.0 | | |
| >20 ng/ml | 25 | 1.0 | 0.5-2.3 | |
| Prosaposin expression | | | | 0.074 |
| Strong | 75 | 1.0 | | |
| Weak | 22 | 2.1 | 1.0-4.4 | |
| Patient survival | | | | |
| Gleason score† | | | | ns |
| ≤3+4 | 42 | 1.0 | | |
| ≥4+3 | 55 | 1.0 | 0.4-2.5 | |
| Pathological stage‡ | | | | ns |
| pT2 | 29 | 1.0 | | |
| ≥PT3 | 68 | 1.9 | 0.6-5.6 | |
| Preoperative s-PSA§ | | | | ns |
| ≤20 ng/ml | 72 | 1.0 | | |
| >20 ng/ml | 25 | 0.5 | 0.2-1.4 | |
| Prosaposin expression | | | | 0.026 |
| Strong | 75 | 1.0 | | |
| Weak | 22 | 2.7 | 1.2-6.0 | |

*Likelihood ratio test
†Gleason score examined in prostatectomy specimens
‡Pathological stage (UICC/TNM 1992)
§Six cases lacking information on preoperative s-PSA

Fig. 14

* 10/12 mice died
** 6/12 mice still alive 3 had tumors
*** 1 mouse with tumor all mice alive Injected 1 million ovarian cancer cells intraperitoneally and began treatment 17 days later with cisplatin (4mg/kg QOD), psaptide (40mg/kg QD), a combination of cisplatin and psaptide or PBS QD. Cisplatin treated mice lost ~35-40% body weight, psaptide treated mice did not lose any weight.

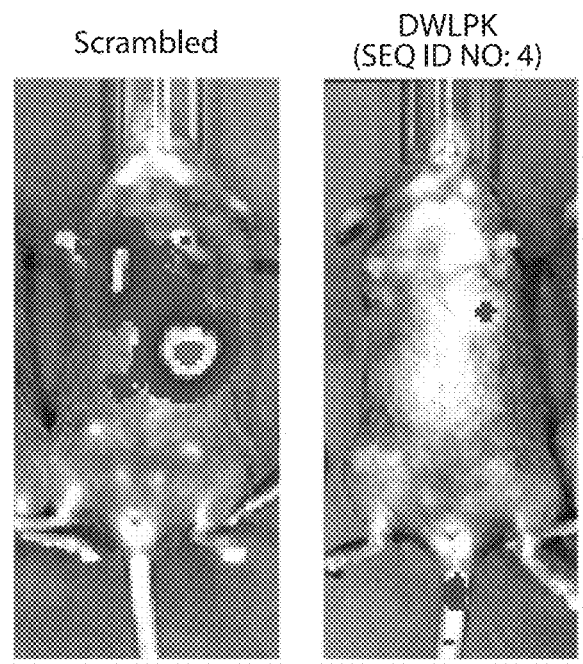
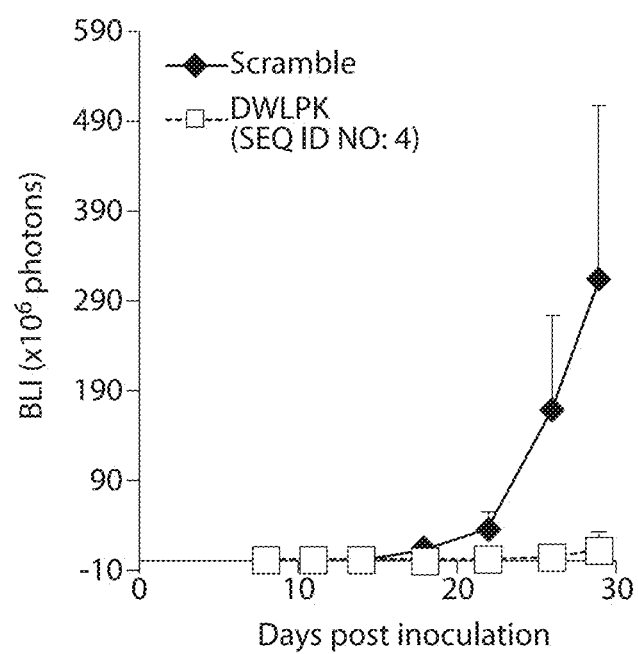
Fig. 22

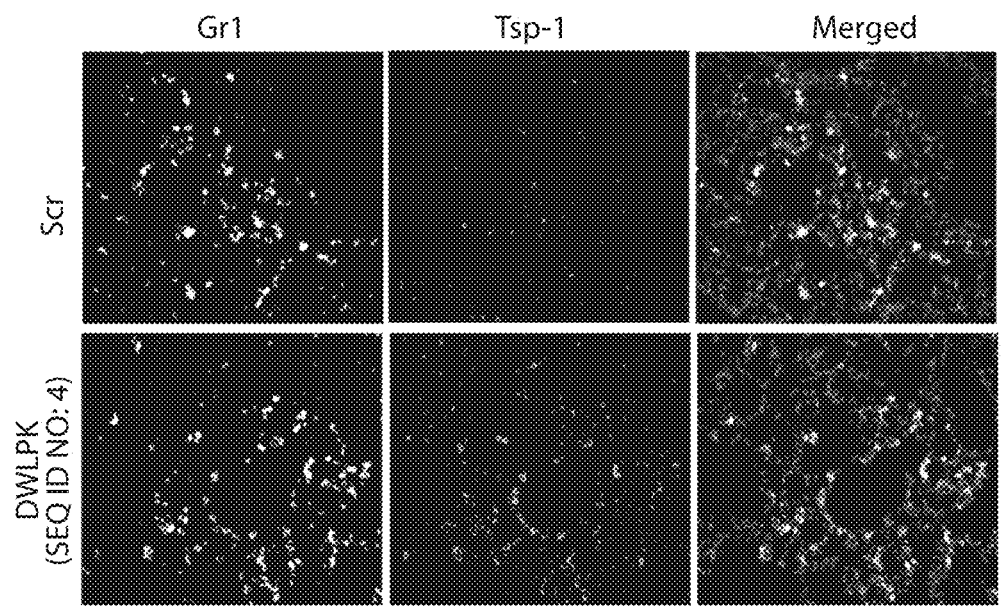
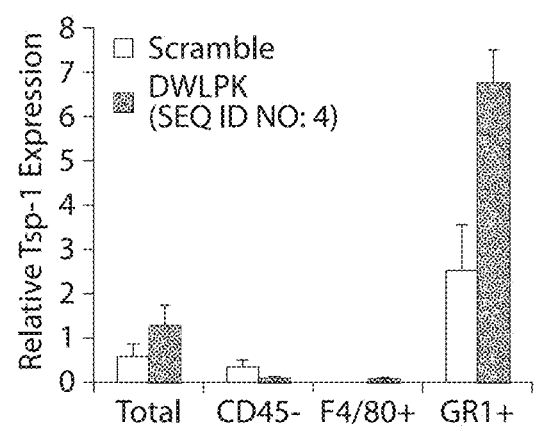
Fig. 23

SAPOSIN-A DERIVED PEPTIDES AND USES THEREOF

CROSS-REFERENCE TO RELATED APPLICATIONS

This application is the U.S. National Stage of International Patent Application No. PCT/US2012/071424, filed Dec. 21, 2012, which claims priority from U.S. Provisional Patent Application No. 61/579,095, filed Dec. 22, 2011, the contents of these applications are incorporated herein by reference in their entirety.

GOVERNMENTAL SUPPORT

This invention was made with. Government support under R01 CA135417 awarded by the National Institutes of Health. The Government has certain rights in the invention.

FIELD OF THE INVENTION

The present disclosure relates to methods for treating a primary tumor, of treating tumor metastasis, as well as methods for preventing and inhibiting tumor metastasis, and preventing relapse. The disclosure further relates to treating angiogenesis-dependent diseases and disorders and preventing relapse.

BACKGROUND OF THE INVENTION

The spread of cancer cells from a primary tumor site to distant organs is known as metastasis. The progression of human cancer to metastatic disease is the major contributing factor to its lethality. Metastasis has been considered one of the most intriguing aspects of the pathogenesis of cancer. Cancer tumor metastasis, or otherwise known as metastatic disease, is responsible for most therapeutic failures in treating the disease, as patients succumb to the multiple tumor growth, accounting for more than 90% of human cancer related deaths. See, for example, Cancer, A Comprehensive Treatise, F. F. Becker (editor), Volume 4, Chapter 3, Plenum Press, New York, 1975.

In order for a tumor to form lethal metastases it must acquire the ability to carry out a complex series of steps. These steps include: gaining access to the vasculature or lymphatic system (intravasation), surviving during transit, exiting the vascular or lymphatic channels (extravasation), and proliferating at the metastatic site. One of the rate limiting steps in the proliferation of tumors, both at the primary and metastatic sites, is the acquisition of the angiogenic phenotype (Folkman, 1971). The induction of angiogenesis not only allows tumors to grow beyond the size limitation imposed by the diffusion limit of oxygen, but also provides a conduit through which the tumor cells can travel and colonize distant organs (Brown et al., 1999; MacDougall and Matrisian, 1995). Once the tumor cells arrive at the metastatic site they must also induce neovascularization in order to grow beyond a microscopic size. It has been documented, however, that metastatic colonies can remain in a microscopic or dormant state and not progress beyond this size for months or years following the initial colonization (Fidler, 2003).

The presence of dormant or micro-metastases indicates that tumor growth and proliferation is not governed solely by cell-autonomous processes and that the conditions present in the microenvironment that permitted proliferation at the primary site can not exist at the metastatic site. Thus, the ability of a tumor to communicate with the surrounding stroma, composed of fibroblasts, immune cells and endothelium must be reestablished upon arrival at the metastatic site. One way in which heterotypic tumor-stromal signaling could affect tumor growth is through the regulation of the production and secretion of pro- and anti-angiogenic proteins by the surrounding stromal fibroblasts and endothelial cells.

The molecular and genetic events that facilitate escape from the primary site and homing to the metastatic site have been well studied. It has been demonstrated in a murine model of breast cancer metastasis that escape from the primary site was largely dependent on the activity of the transcription factor Twist (Yang et al., 2004). Furthermore, microarray analyses of metastatic human breast cancer cells, derived by serial injection into immuno-compromised mice, revealed sets of genes whose expression correlated with their preferred metastatic destination of bone or lung (Kang et al., 2003; Minn et al., 2005). These studies, though yielding key insights into two critical steps of tumor metastasis, namely intravasation and homing, did not address the requirements for tumor establishment and growth at the metastatic site.

It has been previously demonstrated that tumor cells can stimulate the expression of the pro-angiogenic protein VEGF in the surrounding stroma (Dong et al., 2004; Fukumura et al., 1998). However, the regulation of Thrombospondin (Tsp-1), one of the most potent endogenous anti-angiogenic proteins, in the tumor-associated stroma has not been as well studied (Kalas et al., 2005).

New research into the cell-to-cell signaling events between metastatic tumors and their surrounding stroma can yield novel strategies for treating metastatic disease. There is still a need for methods of treating metastatic disease that have less systemic toxicity than the current standard treatments comprising chemotherapy and/or radiation therapy.

The gold standard for cancer treatment is chemotherapy, which broadly targets all dividing cells and has many adverse side effects.

Newer treatments target discrete proteins (e.g., VEGF, Her2, VEGFR, EGFR, Bcr-Abl, etc.), but are limited to targeting single proteins/pathways. Thus, there is efficacy in a limited subset of patients and resistance generally occurs due to mutations or compensation.

There are no FDA approved drugs effectively treating advanced/aggressive cancers. Thus, there is a need for a cancer therapy that avoids these limitations, can inhibit tumor growth and metastasis, and can lead to increased patient survival.

SUMMARY OF THE INVENTION

In cancer patients, tumor and micrometastases can remain for prolonged periods of time in a dormant asymptomatic state before diagnosis and development of disease. Embodiments of the present disclosure are based in part on the discovery that specific polypeptide sequences derived from the protein Saposin A, between 4 and 6 amino acids long, exhibit the anti-angiogenic activity of Saposin A as independent polypeptides, in that they stimulate the expression of p53 and thrombospondin (Tsp-1), and inhibit growth of primary tumors and also metastasis in vivo.

One aspect of the disclosure relates to an isolated polypeptide consisting of 9 or fewer (e.g., 8, 7, 6, 5, or 4) consecutive amino acid residues comprising the active core amino acid sequence DWLP (SEQ ID NO: 5), or an amino acid substitution variant thereof, wherein the amino acid substitution is Tyrosine (Y) for Tryptophan (W); a conservative amino acid substitution for Leucine (L); an Alanine (A) or Glycine (G) for Leucine (L); a D-isomer of Aspartic Acid (D) for an L-isomer of Aspartic Acid (D) and/or a D-isomer of Leucine (L) for a L-isomer of Leucine (L); a D-isomer of Tryptophan (W) for an L-isomer of Tryptophan (W) and/or a D-isomer of Proline (P) for an L-isomer of Proline (P); or combinations thereof; wherein the polypeptide has one or more of the activities of stimulating Tsp-1 expression, activating p53, inhibiting angiogenesis, inhibiting tumor growth, inhibiting tumor invasiveness, and inhibiting tumor metastasis. In some embodiments, the amino acid substitution is a conservative amino acid substitution for Leucine (L); an Alanine (A) or Glycine (G) for Leucine (L); a D-isomer of Aspartic Acid (D) for an L-isomer of Aspartic Acid (D) and/or a D-isomer of Leucine (L) for a L-isomer of Leucine (L); or a D-isomer of Tryptophan (W) for an L-isomer of Tryptophan (W) and/or a D-isomer of Proline (P) for an L-isomer of Proline (P). In some embodiments, the amino acid substitution is a D-isomer of Aspartic Acid (D) for an L-isomer of Aspartic Acid (D) and/or a D-isomer of Leucine (L) for a L-isomer of Leucine (L); or a D-isomer of Tryptophan (W) for an L-isomer of Tryptophan (W) and/or a D-isomer of Proline (P) for an L-isomer of Proline (P). In some embodiments, the isolated polypeptide consists of 9 or fewer (e.g., 8, 7, 6, 5, or 4) consecutive amino acid residues comprising the active core amino acid sequence DWLP (SEQ ID NO: 5).

In some embodiments, the isolated polypeptide has the amino acid sequence DWLPKPNMS (SEQ ID NO: 12), CDWLPKPNM (SEQ ID NO: 13), TCDWLPKPN (SEQ ID NO: 14), KTCDWLPKP (SEQ ID NO: 15), EKTCDWLPK (SEQ ID NO: 16), LEKTCDWLP (SEQ ID NO: 17), or any of said amino acid sequences having a conservative amino acid substitution for an amino acid flanking the DWLP or amino acid substitution variant thereof.

Another aspect of the disclosure relates to an isolated polypeptide consisting essentially of the amino acid sequence CDWLPK (SEQ ID NO: 3), DWLPK (SEQ ID NO: 4), or DWLP (SEQ ID NO: 5), or an amino acid substitution variant thereof; wherein the amino acid substitution is Tyrosine (Y) for Tryptophan (W); a conservative amino acid substitution for Leucine (L); Arginine (R) for Lysine (K); an Alanine (A) or Glycine (G) for Leucine (L); a D-isomer of Aspartic Acid (D) for an L-isomer of Aspartic Acid (D) and/or a D-isomer of Leucine (L) for a L-isomer of Leucine (L); a D-isomer of Tryptophan (W) for an L-isomer of Tryptophan (W) and/or a D-isomer of Proline (P) for an L-isomer of Proline (P); or combinations thereof; wherein the polypeptide has one or more of the activities of stimulating Tsp-1 expression, activating p53, inhibiting angiogenesis, inhibiting tumor growth, inhibiting tumor invasiveness, and inhibiting tumor metastasis. In some embodiments, the amino acid substitution is a conservative amino acid substitution for Leucine (L); an Alanine (A) or Glycine (G) for Leucine (L); a D-isomer of Aspartic Acid (D) for an L-isomer of Aspartic Acid (D) and/or a D-isomer of Leucine (L) for a L-isomer of Leucine (L); or a D-isomer of Tryptophan (W) for an L-isomer of Tryptophan (W) and/or a D-isomer of Proline (P) for an L-isomer of Proline (P). In some embodiments, the amino acid substitution is a D-isomer of Aspartic Acid (D) for an L-isomer of Aspartic Acid (D) and/or a D-isomer of Leucine (L) for a L-isomer of Leucine (L); or a D-isomer of Tryptophan (W) for an L-isomer of Tryptophan (W) and/or a D-isomer of Proline (P) for an L-isomer of Proline (P). In some embodiments, the isolated polypeptide consists essentially of the amino acid sequence CDWLPK (SEQ ID NO: 3), DWLPK (SEQ ID NO: 4), or DWLP (SEQ ID NO: 5). In some embodiments, the isolated polypeptide consists essentially of the amino acid sequence DWLPK (SEQ ID NO: 4) or DWLP (SEQ ID NO: 5). In some embodiments, the isolated polypeptide consisting essentially of the amino acid sequence DWLPK (SEQ ID NO: 4) or DWLP (SEQ ID NO: 5), or an amino acid substitution variant thereof. In some embodiments, the isolated polypeptide consists essentially of the amino acid sequence DWLP (SEQ ID NO: 5). In some embodiments, the isolated polypeptide consisting essentially of the amino acid sequence DWLP (SEQ ID NO: 5), or an amino acid substitution variant thereof.

In some embodiments of any of the polypeptides described above, the isolated polypeptide the conservative amino acid substitution for Leucine is Valine (V). In some embodiments of any of the polypeptides described above, the amino acid substitution for Leucine (L) is Glycine (G) or Alanine (A). In some embodiments of any of the polypeptides described above, the amino acid substitution for Leucine (L) is Glycine (G).

In some embodiments of any of the polypeptides described above, the polypeptide is fused/conjugated to at least one therapeutic molecule.

Another aspect of the disclosure relates to a chimeric polypeptide comprising at least a first portion and at least a second portion, wherein the first portion is a polypeptide described above, and wherein the second portion is a non-Psap polypeptide. In some embodiments, the second portion comprises an amino acid sequence or a polymer that enhances the serum half-life of said first portion. In some embodiments, the second portion comprises an antibody Fc domain. In some embodiments, the second portion comprises an antibody. In some embodiments, the first portion is not contained within a CDR region of an antibody. In some embodiments, the second portion does not comprise any of SEQ ID NOs: 120-123. In some embodiments, the second portion is a therapeutic molecule.

In some embodiments of any of the polypeptides described above, or any chimeric polypeptide described above, the polypeptide or chimeric polypeptide is functionally modified to enhance stability. In some embodiments, any of the polypeptides described above, or any chimeric polypeptide described above, comprise an N-terminal acetyl group and/or a C terminal amide group. In some embodiments, any of the polypeptides described above, or any chimeric polypeptide described above, comprise an N-terminal acetyl group and a C terminal amide group. In some embodiments, the polypeptide is Ac-dWlP-Amide or Ac-DWLP-Amide (Ac=acetyl group, lower case D and L indicate D-amino acids, SEQ ID NOs: 132 and 133, respectively).

Another aspect of the disclosure relates to an isolated nucleic acid encoding the polypeptide or chimeric polypeptide described above. Another aspect of the disclosure relates to a nucleic acid vector comprising the isolated nucleic acid.

Another aspect of the disclosure relates to a peptoid molecule based on the amino acids sequence of the polypeptide or chimeric polypeptide described above.

Another aspect of the disclosure relates to a composition comprising a peptide or chimeric polypeptide described above, and a pharmaceutically acceptable carrier.

Another aspect of the disclosure relates to a method or use of a peptide or chimeric polypeptide described above, for the treatment of an angiogenesis-dependent disease or disorder.

Another aspect of the disclosure relates to a method or use of a peptide or chimeric polypeptide described above, for inhibiting angiogenesis in a subject in need thereof. In some embodiments, the subject in need thereof has an angiogenesis-dependent disease or disorder. In some embodiments, the subject has cancer.

Another aspect of the disclosure relates to a method or use of a peptide or chimeric polypeptide described above, for stimulating expression of Tsp-1 in a subject (in need thereof. In some embodiments, the subject in need thereof has an angiogenesis-dependent disease or disorder. In some embodiments, the subject has cancer.

Another aspect of the disclosure relates to a method or use of a peptide or chimeric polypeptide described above, for inhibiting the recurrence of an angiogenesis-dependent disease or disorder in a subject.

Another aspect of the disclosure relates to a method or use of a peptide or chimeric polypeptide described above, for inhibiting growth and/or metastasis of cancer in a subject diagnosed with cancer.

Another aspect of the disclosure relates to use of a peptide or chimeric polypeptide described above, for the manufacture of a medicament for the treatment of an angiogenesis-dependent disease or disorder.

Another aspect of the disclosure relates to use of a peptide or chimeric polypeptide described above, for the manufacture of a medicament for inhibiting angiogenesis in a subject in need thereof. In some embodiments, the subject in need thereof has an angiogenesis-dependent disease or disorder. In some embodiments, the subject has cancer.

Another aspect of the disclosure relates to use of a peptide or chimeric polypeptide described above, for the manufacture of a medicament, for stimulating expression of Tsp-1 in a subject in need thereof. In some embodiments, the subject in need thereof has an angiogenesis-dependent disease or disorder. In some embodiments, the subject has cancer.

Another aspect of the disclosure relates to use of a peptide or chimeric polypeptide described above, for the manufacture of a medicament for inhibiting the recurrence of an angiogenesis-dependent disease or disorder.

Another aspect of the disclosure relates to use of a peptide or chimeric polypeptide described above, for the manufacture of a medicament for inhibiting growth and/or metastasis of cancer in a subject diagnosed with cancer.

In some embodiments of any of the uses described above the angiogenesis-dependent disease or disorder is selected from a group consisting of cancer, psoriasis, age-related macular degeneration, thyroid hyperplasia, preeclampsia, rheumatoid arthritis and osteoarthritis, inflammatory bowel disease (IBD), Alzheimer's disease, obesity, pleural effusion, atherosclerosis, endometriosis, diabetic/other retinopathies, neovascular glaucoma, age-related macular degeneration, hemangiomas, and corneal neovascularization.

In some embodiments of any of the uses described above the peptide or polypeptide is administered in conjunction with chemotherapy, radiation therapy, a cytostatic agent, an anti-VEGF agent, an anti-angiogenesis factor, and/or a p53 reactivation agent.

Another aspect of the disclosure relates to a method of treating an angiogenesis-dependent disease or disorder, comprising administering to a subject in need thereof a therapeutically effective amount of a composition described above.

Another aspect of the disclosure relates to a method of inhibiting the recurrence of an angiogenesis-dependent disease or disorder, the method comprising administering to a subject in need thereof a therapeutically effective amount of a composition described above.

Another aspect of the disclosure relates to a method of inhibiting growth and/or metastasis of cancer in a subject diagnosed with cancer, the method comprising administering to the subject a therapeutically effective amount of a composition described above.

Another aspect of the disclosure relates to a method of treating an individual diagnosed with cancer. In some embodiments, the method comprises: (a) determining a level of Psap in a sample obtained from said individual; (b) comparing the Psap level determined in (a) with a reference Psap level; and (c) administering a therapeutically effective amount of a composition described above if said Psap level determined in (a) is lower than 95% of said reference Psap level.

Another aspect of the disclosure relates to a method of determining the likelihood of an individual diagnosed with cancer to respond to a Psap treatment. In some embodiments, the method comprises: (a) determining a level of Psap in a sample obtained from said individual; and (b) comparing the Psap level determined in (a) with a reference Psap level, wherein if said Psap level determined in (a) is lower than 95% of said reference Psap level indicates that the individual is likely to respond to administration of a composition described above.

In some embodiments of the methods described above, the angiogenesis-dependent disease or disorder is selected from a group consisting of cancer, psoriasis, age-related macular degeneration, thyroid hyperplasia, preeclampsia, rheumatoid arthritis and osteoarthritis, inflammatory bowel disease (IBD), Alzheimer's disease, obesity, pleural effusion, atherosclerosis, endometriosis, diabetic/other retinopathies, neovascular glaucoma, age-related macular degeneration, hemangiomas, and corneal neovascularization.

In some embodiments of the methods described above, the composition is administered in conjunction with chemotherapy, radiation therapy, a cytostatic agent, an anti-VEGF agent, an anti-angiogenesis factor, and/or a p53 reactivation agent.

BRIEF DESCRIPTION OF THE DRAWINGS

FIG. 5 provides two photographs of experimental results performed to study conservative amino acid substitution analysis of the indicated peptides.

FIG. 6 is a bar graph of experimental results that indicate the tested Psap fragments significantly inhibit prostate tumor growth.

FIG. 12 is a photograph of experimental results by staining tissue indicating that PC3 cells stimulate Tsp-1 in BM-derived cells in vivo.

FIG. 13 is a table, a photograph of stained tissue, and a photograph of a Western blot indicating that Psap correlates clinically with prostate cancer progression.

FIG. 14 is a table of clinical data indicating that Prosaposin levels correlate with recurrence and patient survival.

FIG. 22 is a photograph and graph of experimental data indicating that a Psap peptide inhibits lung metastasis.

FIG. 23 is a photograph of stained tissue and a graph of experimental data indicating that a Psap peptide stimulates Tsp-1 in BM-derived cells in vivo.

DETAILED DESCRIPTION OF THE INVENTION

Figure 1:
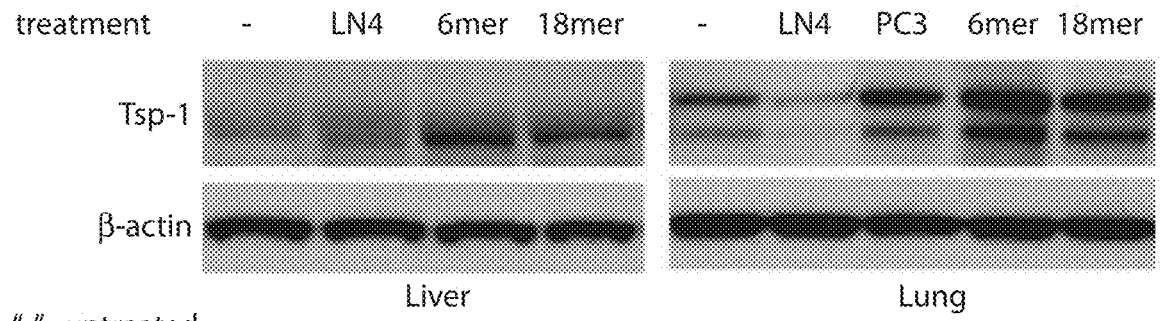
FIG. 1 is a collection of photographs of results of experiments that indicates the 6-mer and 18-mer peptides derived from Saposin A stimulate Tsp-1 in vivo.

It has previously been shown that non- or weakly metastatic tumor cells secrete a protein that stimulates the expression of thrombospondin (Tsp-1) in the surrounding environment of the tumor cells, namely the stroma comprised of fibroblasts and endothelial cells. There was also strong correlation between metastasis, Psap and Tsp-1 expression in the tumor cells, and Psap and Tsp-1 expression in the tumor stroma. In addition, there was a strong correlation between metastasis and the Psap level in the plasma and/or platelets of patients with metastatic cancers. Both the plasma and platelets of patients with non-metastatic cancers contained elevated levels of Psap compared to normal individuals not diagnosed with cancers. In contrast, the plasma and platelets of patients with metastatic cancers contain Psap levels that are comparable to normal individuals with no diagnosed cancers. While not wishing to be bound by theory, the shift from elevated levels of Psap levels to normal or lower than normal Psap levels indicates the transition from non-metastatic to metastatic cancer. Furthermore, the increase in expression of Tsp-1 in the stroma is thought to prevent the tumor cells from metastasizing. Tsp-1 is a potent endogenous anti-angiogenic factor that has been previously explored as a cancer therapy. Abbott Laboratories developed a Tsp-1 peptide that showed preclinical efficacy and showed no toxicity in Phase I clinical trials, but failed phase II (no significant efficacy). Stimulation of Tsp-1 expression by the tumor-derived protein is via the activation of the tumor suppressor p53. The tumor suppressor p53 is a transcription activator of Tsp-1 expression. This tumor-associated protein secreted by non- or weakly metastatic tumor cells is prosaposin (Psap). In addition, two peptide fragments from Saposin A, Saposin A being a cleavage product of Psap, were also capable of stimulating Tsp-1 expression in vitro and in vivo. These two peptide fragments were CDWLPKPNM-SASC (SEQ ID NO: 41) and LEKTCDWLPKPNM-SASCKEI (SEQ ID NO: 37). Described herein are experiments which indicate, surprisingly, that fragments of Saposin A as small as four amino acids retain the activity of the Saposin A protein and fragments previously identified.

Prosaposin (Psap) is the saposin precursor protein made up of approximately 524-527 amino acids which includes a 16 amino acids signal peptide. The full-length precursor 53-kDa polypeptide undergoes co-translational glycosylation and modification in the endoplasmic reticulum and Golgi system to yield a 70-72 kDa precursor protein. After transport to the lysosome, cathepsin D participates in its proteolytic processing to yield intermediate molecular forms of 35 to 53 kDa and then to a 13-kDa glycoprotein and finally to the mature 8-11 kDa partially glycosylated forms of individual saposin molecules (O'Brien J. S., and Kishimoto Y, The FASEB J., 5: 301-8, 1991; Kishimoto Y. et al., J. Lipid Res. 33:1255-67, 1992), There are currently three known splice variants of the precursor protein; isoforms a, b and c.

Psap and the individual saposin proteins are expressed by a wide variety of cell types originating from ectodermal, mesodermal, and endodermal germ layers including but not limited to lung, skin, fibroblast, stromal cells, bone, smooth muscle, skeletal muscle, cardiac muscle, placenta, red and white blood cells, pancreas, lymphoreticular system (spleen, thymus, liver), micro and macrovascular system, genitourinary system (e.g., prostate, testes, seminal vesicle), and central and peripheral nervous system. Prosaposin and saposins are also present as soluble proteins in extracellular space/fluid including pleural fluid, cerebrospinal fluid, seminal fluid, milk, and serum (Campana W M., et al., 1999; Kishimoto Y. et al., 1992).

Definitions

As used herein, the term "stroma" or "tumor stroma" refers to the connective tissue framework and non-tumor cells of a tumor. Examples of some non-tumor cells found in a tumor stroma are fibroblasts and endothelial cells.

As used herein, the term "tumor" means a mass of transformed cells that are characterized, at least in part, by containing angiogenic vasculature. The transformed cells are characterized by neoplastic uncontrolled cell multiplication which is rapid and continues even after the stimulus that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e., a metastatic tumor), a tumor also can be nonmalignant, (i.e., lacking the ability to metastasize). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to the progression of a tumor at the original site of tumor development (known as a primary tumor) to a secondary location. Such a tumor at the secondary location is referred to as a "secondary tumor" in that it grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location.

As used herein, a "malignant tumor" is one having the properties of invasion and metastasis and showing a high degree of anaplasia. Anaplasia is the reversion of cells to an immature or a less differentiated form, and it occurs in most malignant tumors.

As used herein, the term "recurrence" of an angiogenic disease or disorder refers to the re-manifestation/re-development of known symptoms associated with the angiogenic disease or disorder after previous successful treatment of the angiogenic disease or disorder. For example, a "recurrence" of a tumor refers to the enlargement of an existing tumor whose growth had stopped or reduced during an anti-cancer therapy, or the emergence of a tumor at the original (primary) site of tumor discovery after the original tumor had been excised or reduced in size. The recurrence of a tumor can also mean new tumor growth(s) of the same tumor type as the original tumor at a site different from the original site of tumor discovery. This can be an indication that the original primary tumor has spread to other locations, or the primary tumor has emerged as an anti-angiogenic resistant form. For example, a recurrence of rheumatoid arthritis can include localized swelling/pain/joint stiffness, and elevated leukocyte ingression after a period of disease remission and symptom free.

As used herein, the term "inhibit" or "inhibition" means the reduction or easing of a phenomenon, such as tumor growth and/or tumor metastasis and/or angiogenesis. Inhibition includes slowing of a rate of progression (e.g., of tumor growth and metastasis). The rate can be reduced by about 20%, about 30%, about 40%, about 50%, about 60%, about 70%, about 80%, about 90%, about 100%, about 125%, about 150% or more compared to an appropriate control, (e.g., an untreated tumor of the same type). Inhibition can also mean a reduction in overall symptom (e.g. reduction in the size of a tumor). Reduction can be at least 10%, at least 20%, at least 30%, at least 40%, at least 50%, at least 60%, at least 70%, at least 80%, at least 90%, at least 100% or more compared to an appropriate control.

As used herein, the term "enhance", "enhancing", "stimulate" or "stimulating" means the increase of a phenomenon, such as expression of Tsp-1. This increase can be by about 20%, about 30%, about 40%, about 50%, about 60%, about 70%, about 80%, about 90%, about 100%, about 125%, about 150%, about 200%, about 500%, or more compared to an appropriate control (e.g., a cell, tumor, portion of a tumor, stroma surrounding a tumor, plasma, whole blood or a fibroblast with basal or minimal Tsp-1 expression). These terms also encompass increasing a phenomenon from a zero state (e.g., no or undetectable Tsp-1 expression in a cell, tumor, portion of a tumor, stroma surrounding a tumor, plasma, whole blood or a fibroblast) to a non-zero state (e.g., some Tsp-1 expression or detectable Tsp-1 expression in a cell, tumor, portion of a tumor, stroma surrounding a tumor, plasma, whole blood or a fibroblast).

The term "prevention" as used to refer to tumor growth and/or metastasis means no further increase in the size of the tumors from the time of start of treatment administration. Prevention also means status quo of no new metastatic tumors detected (i.e., no further spread of cancer) and/or an increase amount of tumor markers detected by methods known in the art.

As used herein, the term "therapeutically effective amount" refers to the amount that is safe and sufficient to produce a clinically beneficial result in a subject. Such results, for example are prevention or delay of the development and further spread of metastases in a cancer patient, cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastasis.

The term "treat" or "treatment" refers to obtaining therapeutic or palliative benefit for a subject, wherein the object is to slow down, and/or halt the development or worsening of, or reverse progression of a disease (e.g., spread of a tumor). Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with the disease or disorder as well as those likely to develop the disease or a secondary form of the disease (e.g., secondary tumors due to metastasis).

The term "angiogenesis", as used herein refers to the sprouting of new blood vessels from pre-existing blood vessels, characterized by endothelial cell proliferation and migration triggered by certain pathological conditions, such as the growth of solid tumors and metastasis.

As used herein, the term "angiogenesis-dependent disease or disorder" refers to diseases or disorders that are dependent on a rich blood supply and blood vessel proliferation for the disease's pathological progression (e.g., metastatic tumors) or diseases or disorders that are the direct result of aberrant blood vessel proliferation (e.g., diabetic retinopathy and hemangiomas). Examples include abnormal vascular proliferation, ascites formation, psoriasis, age-related macular degeneration, thyroid hyperplasia, preeclampsia, rheumatoid arthritis and osteoarthritis, inflammatory bowel disease (IBD), Alzheimer's disease, obesity, pleural effusion, atherosclerosis, endometriosis, diabetic/other retinopathies, ocular neovascularizations such as neovascular glaucoma and corneal neovascularization.

As used herein, the term "nucleic acid" refers to DNA or RNA. The term encompasses sequences that include any of the known base analogs of DNA and RNA.

The term "vector" used herein refers to a self-perpetuating nucleic acid sequence which can receive and perpetuate heterologous nucleic acid sequences. Vectors typically contain an origin of replication and other sequences that are required for replication by a host organism. Useful vectors include, without limitations, viral vectors, plasmids, bacteriophage, bacterial artificial chromosomes or yeast artificial chromosomes. A vector can be a DNA or RNA vector. A vector can be either a self-replicating extrachromosomal vector or a vector which integrate into a host genome. A vector can be prokaryotic, eukaryotic or both. A vector can be designed for use in bacterial and/or mammalian cells. A vector may further be an "expression vector", which refers to the incorporation of coding sequences operably linked to the expression/regulatory sequences that function in the expression of the coding sequences when in the appropriate context (e.g., in a prokaryotic or eukaryotic cell). Expression vectors can be bacterial or mammalian or both. In general, expression vectors of utility in recombinant DNA techniques are often in the form of "plasmids" which refer to circular double stranded DNA loops which, in their vector form are not bound to the chromosome. Other expression vectors can be used in different embodiments of the disclosure, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors can be for stable or transient expression of the encoded protein product.

As used herein, the term "viral vector," refers to a nucleic acid vector construct that includes at least one element of viral origin and includes elements sufficient for or permissive of packaging into a viral vector particle. A viral vector can contain the coding sequence for a Psap protein in place of non-essential viral genes. The vector and/or particle can be utilized for the purpose of transferring DNA, RNA or other nucleic acids into cells either in vitro or in vivo. Numerous forms of viral vectors are known in the art. In some embodiments, the viral vector is designed for expression of the incorporated coding sequences (e.g., a viral expression vector) when in the appropriate context.

As used herein, the term "prognosis" encompasses predictions and likelihood analysis of disease progression, particularly tumor recurrence, metastatic spread, and disease relapses. The prognosis method described herein is intended for clinical use in making decision concerning treatment modalities, including therapeutic interventions, diagnostic criteria such as disease staging, and disease monitoring and surveillance for metastasis or recurrence of neoplastic disease.

As used herein, a "sample" refers to a portion, piece, part, segment, or fraction of a tissue which is obtained or removed from an intact tissue or organ of a subject or a bodily fluid (e.g., blood, plasma, urine, saliva) obtained from the subject, preferably a human subject.

As used herein, a "subject" refers to a mammal, preferably a human. The term "individual", "subject", and "patient" are used interchangeably.

As used herein, a "tumor sample" refers to a portion, piece, part, segment, or fraction of a tumor, for example, a tumor which is obtained or removed from a subject (e.g., removed or extracted from a tissue of a subject), preferably a human subject.

The terms "polypeptide" and "peptide" are used interchangeably herein to refer to a polymer of amino acids. These terms do not connote a specific length of a polymer of amino acids. Thus, for example, the term includes oligomeric peptides, made up of two or more physically linked peptides, whether produced using recombinant techniques, chemical or enzymatic synthesis, or naturally occurring.

The term "heterologous" when describing a plurality of polypeptide or proteins is used to refer to two or more different amino acid sequences that typically are found in nature within separate, different and distinct proteins. Such as when two naturally unrelated polypeptides are linked together by engineering in a laboratory.

As used herein, the term "variant" when used in reference to a polypeptide, refers to a polypeptide that has one or more amino acid substitutions (e.g., a conservative amino acid substitution, or a D-isomer amino acid substitution). The term "substitution variant," "variant peptide" and "amino acid substitution variant" are used interchangeably herein. The term "splice variant" encompasses a separate definition, as known in the art.

As used herein, the term "non-Psap polypeptide" is used to refer to a protein or polypeptide that is not the Psap protein (does not have the amino acid sequence of the intact Psap protein), and to refer to a protein or polypeptide with an amino acid sequence that is not otherwise derived from the amino acid sequence of the Psap protein.

As used herein, the term "Psap protein" refers to the various isoforms encoded by the nucleic acids of Psap (Genbank Accession No. NM_002778, NM_001042465, or NM_001042466). For example, the splice variant full-length human prosaposin isoform A preproprotein (Genbank Accession Nos.: NM_002778, NP_002769.1; UniProtKB/Swiss-Prot P07602, UniProtKB/TrEMBL Q53Y86), the splice variant full-length human prosaposin isoform B preproprotein (Genbank Accession Nos.: NM_001042465.1, NP_001035930.1); UniProtKB/Swiss-Prot entry P07602), and the splice variant full-length human prosaposin isoform C preproprotein (Genbank Accession Nos.: NM_001042466.1, NP_001035931.1); GenPept/UniProtKB/TrEMBL: O75905, P07602.2, Q53FJ5, Q59EN5, Q5BJH1, Q5JQ36, and Q5JQ37.

The term "modified polypeptide" or "derivatized polypeptide" refer to polypeptides that have additional features other than amino acid content. As used herein, a "modification" or "derivative" of a peptide produces a modified or derivatized polypeptide, which is a form of a given peptide that is chemically modified relative to the reference peptide, the modification including, but not limited to, oligomerization or polymerization, modifications of amino acid residues or peptide backbone, cross-linking, cyclization, conjugation, pegylation, glycosylation, acetylation, phosphorylation, fusion to additional heterologous amino acid sequences, or other modifications that substantially alter the stability, solubility, or other properties of the peptide while substantially retaining Tsp-1 expression stimulating activity described herein.

By "PEGylated" is meant the covalent attachment of at least one molecule of polyethylene glycol to a biologically active molecule. The average molecular weight of the reactant PEG is preferably between about 3,000 and about 50,000 daltons, more preferably between about 10,000 and about 40,000 daltons, and most preferably between about 15,000 and about 30,000 daltons. Particularly preferred are PEGs having nominal average sizes of about 20,000 and about 25,000 daltons. The method of attachment is not critical, but preferably does not alter, or only minimally alters, the activity of the biologically active molecule. Preferably the increase in half-life is greater than any decrease in biological activity. A preferred method of attachment is via N-terminal linkage to a polypeptide or peptide.

As used herein, the term "differentially glycosylated" refers to differences in glycosylation at the available glycosylation sites of full-length Psap. There are five glycosylation sites on the full-length protein. For instance, a full-length Psap can have anywhere from zero and up to five glycosylated groups. In addition, the term also refers to the presence of different sugar groups on a polypeptide.

As used herein, the term "peptide mimetic" or "peptidomimetic" refers to a synthetic agent or molecule that biologically mimics the activity if a peptide described herein, such as stimulation of Tsp-1 and/or p53 expression. By "biologically mimics" is meant that a peptidomimetic derivative of a peptide as described herein has at least 50% of the biological activity of the peptide itself.

As used herein, the term "cancer" refers to any of various malignant neoplasms characterized by the proliferation of anaplastic cells that tend to invade surrounding tissue and metastasize to new body sites as well as to the pathological conditions characterized by such malignant neoplastic growths.

As used herein, the term "promptness" refers to any time within one month of positive laboratory test results confirming presence of cancer cells.

As used herein, the phrase "development of cancer" or "cancer development" refers to the development of primary or initial cancer, the development of metastasis from benign and/or malignant tumors, and/or the development of malignancy from benign tumors.

As used herein, the term "fusion protein" or "fusion polypeptide" refers to a protein created by contiguously joining two heterologous genes or two heterologous proteins/polypeptides or portions thereof together, typically through genetic engineering, to thereby produce one contiguous protein. By "heterologous" in reference to genes and proteins means the genes or proteins are two different and not similar entities. For example, two heterologous genes encode two different and not similar proteins respectively. Thus, a "fusion protein" or "fusion polypeptide" is a chimeric protein, made of at least two different types of proteins or portions thereof. In the laboratory, a "fusion protein" or "fusion polypeptide" is achieved through the creation of a fusion gene which is done, for example, through the removal of the stop codon from a DNA sequence of the first protein and then attaching the DNA sequence of the second protein in frame. The resulting DNA sequence can then be transcribed and translated by a cell into a single protein. Alternatively, in a fusion protein, the two heterologous proteins can be joined together with a linker or spacer peptide added between the two proteins. This linker or spacer peptide can often contain protease cleavage site(s) to facilitate the separation of the two different proteins after expression and purification. The making of fusion proteins as a technique is commonly used for the identification and purification of proteins through the fusion of a GST protein, FLAG peptide or a hexa-His peptide.

As used herein, a "peptide linker" is a short sequence of amino acids that is not part of the sequence of either of two peptides being joined to form a fusion protein or fusion polypeptide. A peptide linker is attached on its amino-terminal end to one polypeptide or polypeptide domain and on its carboxyl-terminal end to another polypeptide or polypeptide domain. Examples of useful linker peptides include, but are not limited to, glycine polymers ((G)n) including glycine-serine and glycine-alanine polymers (e.g., a (Gly4Ser)n repeat where n=1-8, preferably, n=3, 4, 5, or 6). The peptide linker can be a flexible linker, in that the peptide sequence does not adopt any secondary structures known in proteins, e.g., alpha helices. Such flexible linkers are predominantly made of non-charged, apolar amino acid residues and are hydrophobic. Secondary protein structures can be determined by methods known in the art, for example, circular dichroism. An example of a flexible peptide linker is LGGGGSGGGGSA (SEQ ID NO: 1). Alternately, the peptide linker can take the form a monomeric hydrophilic α-helix, for example, AEAAAKEAAAKEA (SEQ ID NO: 2).

In one respect, the term "comprising" in reference to the herein described compositions and methods, refers to respective component(s) thereof, as essential to the compositions and methods, yet open to the inclusion of unspecified elements, essential or not.

In some embodiments, other elements that can be included in the description of the composition, method or respective component thereof are limited to those that do not materially affect the basic and novel characteristic(s) of the composition, method or respective component thereof. This is referred to using the term "consisting essentially of". This applies equally to steps within a described method as well as compositions, peptides and components therein. In other embodiments, the peptides, compositions, methods, and respective components thereof, described herein are intended to be exclusive of any element not recited with respect to that composition, element, component or method. This is referred to using the term "consisting of".

The "essential" part of a polypeptide described herein, is the polypeptide sequence that has the activity, at the minimum, of stimulation of Tsp-1 expression (e.g., in the assays described herein), and may also stimulate p53 expression. Such activity is seen in the 4-6 mers described herein. Other possible essential activities include one or any combination of the inhibition of angiogenesis, inhibition of tumor growth, inhibition of tumor invasiveness, and inhibition of tumor metastasis, as described herein. Non-essential components of the compositions described herein would be contributed, for example, by heterologous polypeptide sequences that are non-Psap polypeptides, fusion portion of a peptidal fusion protein that is not Psap, and any modifications (e.g., post-translational) to the polypeptide.

The term "reducing the likelihood" in reference to the development of certain conditions refers to a reduction by at least 20% compared to when no treatment or administration of a therapeutically effective amount of a Psap protein or a vector described herein. The reduction can also be at least 30%, at least 40%, at least 50%, at least 60%, at least 70%, at least 80%, at least 90%, at least 100%, including all the percent between 20% and 100%.

Aspects of the disclosure described herein stem from the identification of short peptide/polypeptides (between 4 and 6 amino acids) that exhibit the activity (some of which exhibit increased activity), of Saposin A, in that they stimulate Tsp-1 expression, and inhibit tumor growth, invasiveness and metastasis. These polypeptides are referred to herein as "the 4-6 mers". These 4-6 mers exhibit biological activity as isolated polypeptides, cyclic polypeptides, and also when in the context of larger fusion polypeptides. As such, the present disclosure relates to these 4-6 mers, fusion proteins comprising these 4-6 mers linked to heterologous polypeptides, nucleic acids encoding the 4-6 mers (e.g., isolated and/or purified), nucleic acids encoding the fusion proteins, and pharmaceutical compositions comprising these 4-6 mer polypeptides and/or nucleic acids. Methods of treatment described herein that utilize these compositions are further encompassed.

In some embodiments, the 4-6 mers or fusion proteins described herein are modified or derivatized.

The 4-6 mers that exhibit the activity of Saposin A include polypeptides with the amino acid sequence CDWLPK (SEQ ID NO: 3), DWLPK (SEQ ID NO: 4), DWLP (SEQ ID NO: 5), DWAP (SEQ ID NO: 6), DYLPK (SEQ ID NO: 7), DWVPK (SEQ ID NO: 8), DWLPR(SEQ ID NO: 9), DWAPK (SEQ ID NO: 10), and DYLP (SEQ ID NO: 11). In addition, any of these polypeptides having a conservative amino acid substitution for Leucine (L) or an Alanine (A) or Glycine (G) for Leucine (L) is also considered a 4-6 mer as described herein. Furthermore, any of these polypeptides having one or more D-amino acid substitutions (e.g., at Tryptophan (W) and Proline (P) and/or Aspartic Acid (D) and Leucine (L)) are also considered a 4-6 mer as described herein.

Aspects of the disclosure relate to a peptide/polypeptide consisting of the 4-6 mer described herein. Other aspects of the disclosure relate to the nucleic acid that encodes the polypeptide consisting of the 4-6 mer described herein.

One aspect of the disclosure relates to a polypeptide consisting of the amino acid sequence CDWLPK (SEQ ID NO: 3), DWLPK (SEQ ID NO: 4), or DWLP (SEQ ID NO: 5), or an amino acid substitution variant thereof, wherein the amino acid substitution is a) Tyrosine (Y) for Tryptophan (W); b) a conservative amino acid substitution for Leucine (L); c) Arginine (R) for Lysine (K); or d) a D-isomer of Aspartic Acid (D) for the L-isomer of Aspartic Acid (D) and/or a D-isomer of Leucine (L) for the L-isomer of Leucine (L); e) or a D-isomer of Tryptophan (W) for the L-isomer of Tryptophan (W) and/or a D-isomer of Proline (P) for the L-isomer of Proline (P); or f) an Alanine (A) or Glycine (G) for Leucine (L).

Aspects of the disclosure relate to a polypeptide consisting essentially of the 4-6 mer described herein. Other aspects of the disclosure relate to the nucleic acid that encodes the polypeptide consisting essentially of the 4-6 mer described herein.

In some embodiments, the present disclosure involves the amino acid sequences identified herein as having the Saposin A activity, (e.g., the 4-6 mer) and the nucleic acids encoding them, in the context of heterologous flanking sequences. Put another way, the specific polypeptide sequences described herein (e.g., CDWLPK (SEQ ID NO: 3), DWLPK (SEQ ID NO: 4), DWLP (SEQ ID NO: 5)) or nucleic acid encoding them, when in the context of a larger polypeptide, are present in that larger peptide in the absence of directly adjacent sequences (e.g., 5, 6, 7, 8, 9, or 10 or more directly adjacent amino acids or nucleic acid encoding said amino acids) which are found in nature in that context. By way of example, the polypeptides (CDWLPK (SEQ ID NO: 3), DWLPK (SEQ ID NO: 4), DWLP (SEQ ID NO: 5), DWAP (SEQ ID NO: 6), DYLPK (SEQ ID NO: 7), DWVPK (SEQ ID NO: 8), DWLPR (SEQ ID NO: 9), DWAPK (SEQ ID NO: 10), and DYLP (SEQ ID NO: 11)) are typically found in nature in the context of flanking amino acids of an entire protein (e.g., Saposin A). The nucleic acids encoding the 4-6mers are typically found in nature in the form of a chromosome or an mRNA, with flanking nucleic acid sequences encoding the entire protein (e.g., the Saposin A protein), and regulatory sequences. Such non-heterologous forms of these specific polypeptide sequences are not considered as part of this embodiment of the present disclosure. In some embodiments, the present embodiment is specifically limited to the 4-6 mers described herein, either independent of any flanking amino acid sequences, or in the context of flanking amino acid sequences (either C-terminal, N-terminal, or both) that are heterologous to the 4-6 mers. Such sequences are necessarily intentionally combined by the skilled practitioner in a laboratory setting.

In some embodiments, the peptide/polypeptide of the present disclosure that includes a 4-6 mer described herein (e.g., as the essential part) is no greater than 4-6 amino acids in length, respectively (e.g., CDWLPK (SEQ ID NO: 3), DWLPK (SEQ ID NO: 4), or DWLP (SEQ ID NO: 5), or variants thereof described herein). Put another way, there are no additional amino acids other than the 4, 5, or 6 amino acids specified herein. In some embodiments, the polypeptide of the present disclosure that includes the 4-6 mer described herein is no greater than 7 amino acids in length, no greater than 8 amino acids in length, or no greater than 9 amino acids in length. In some embodiments, the polypeptide of the invention is 9 or fewer (e.g., 8, 7, 6, 5, or 4) amino acids in length. In some embodiments, the peptide/polypeptide of the present disclosure has one or more activities of stimulating Tsp-1 expression, activating p53, inhibiting angiogenesis, inhibiting tumor growth, inhibiting tumor invasiveness, and inhibiting tumor metastasis.

One aspect of the disclosure relates to a polypeptide consisting essentially of the amino acid sequence CDWLPK (SEQ ID NO: 3), DWLPK (SEQ ID NO: 4), or DWLP (SEQ ID NO: 5), or an amino acid substitution variant thereof, wherein the amino acid substitution is a) Tyrosine (Y) for Tryptophan (W); b) a conservative amino acid substitution for Leucine (L); c) Arginine (R) for Lysine (K); or d) a D-isomer of Aspartic Acid (D) for the L-isomer of Aspartic Acid (D) and/or a D-isomer of Leucine (L) for the L-isomer of Leucine (L); or e) or a D-isomer of Tryptophan (W) for the L-isomer of Tryptophan (W) and/or a D-isomer of Proline (P) for the L-isomer of Proline (P); or f) an Alanine (A) or Glycine (G) for Leucine (L).

Amino Acid Isomers

As described herein, polypeptides having D-amino acid substitutions were also shown to have the activity of Saposin A. As such, amino acid substitution variants resulting from substitution of one or more D-amino acids for the like L-amino acid are further encompassed by the term 4-6 mer. In some embodiments, one D-amino acid substitution is present. In some embodiments, 2 or more D-amino acid substitutions are present. In some embodiments, 3, 4, or 5 D-amino acid substitutions are present. In some embodiments, the D-amino acid substitutions are evenly spaced, e.g., every other amino acid, of the 4-6 mer. In some embodiments, the D-amino acid substitution is for Tryptophan (W) and/or Proline (P). In some embodiments, the D-amino acid substitution is for Aspartic Acid (D) and/or Leucine (L)).

Of the standard α-amino acids, all but glycine can exist in either of two optical isomers, called L or D amino acids, which are mirror images of each other. While L-amino acids represent all of the amino acids found in proteins during translation in the ribosome, D-amino acids are found in some proteins produced by enzyme posttranslational modifications after translation and translocation to the endoplasmic reticulum. The L and D convention for amino acid configuration refers not to the optical activity of the amino acid itself, but rather to the optical activity of the isomer of glyceraldehyde from which that amino acid can, in theory, be synthesized (D-glyceraldehyde is dextrorotary; L-glyceraldehyde is levorotary).

Fusion/Chimeric Polypeptides

Another aspect of the present disclosure relates to a fusion/chimeric polypeptide comprising at least a first portion and at least a second portion, wherein the first portion is a polypeptide consisting of a 4-6 mer as described herein or a polypeptide of 9 or fewer (e.g., 8, 7, 6, 5, or 4) amino acid residues as described herein and the second portion is another heterologous polypeptide (e.g., a non-Psap polypeptide). Useful second portions of the fusion polypeptide are described herein. A 4-6mer occurring within the context of a naturally occurring polypeptide is not encompassed by fusion polypeptides as described herein.

Another aspect of the present disclosure relates to a fusion/chimeric polypeptide comprising at least a first portion and at least a second portion, wherein the first portion is a polypeptide consisting essentially of a 4-6 mer as described herein or a polypeptide of 9 or fewer (e.g., 8, 7, 6, 5, or 4) amino acid residues as described herein and the second portion is another heterologous polypeptide (e.g., a non-Psap polypeptide). Useful second portions of the fusion polypeptide are described herein.

Another aspect of the disclosure relates to a nucleic acid encoding the fusion polypeptides described herein. The nucleic acids described herein may be in the context of a vector. As such, another aspect of the disclosure relates to a vector comprising the isolated nucleic acid described herein.

Non-limiting examples of useful second portions of the fusion polypeptide of the present disclosure are serum transferrin or portions thereof, albumin, transthyretin, Fc domain of IgG (see, e.g., G. M. Subramanian, (2007), Nature Biotechnology 25, 1411-141). In some embodiments, the second portion comprises an antibody Fc domain or an antibody. In some embodiments, the second portion comprising an antibody Fc domain or an antibody does not have the amino acid sequence of any of SEQ ID NOs: 120-121 In some embodiments, the fusion/chimeric polypeptide comprises at least a first portion consisting of a 4-6 mer as described herein or a polypeptide of 9 or fewer (e.g., 8, 7, 6, 5, or 4) amino acid residues as described herein that is not contained within a complementarity determining region (CDR) of an antibody and a second portion comprising an antibody Fc domain. The second portion can be another therapeutic molecule. In some embodiments of the fusion polypeptide, the second portion comprises an amino acid sequence or a polymer that enhances the serum half-life of the first portion. In some embodiments of the isolated fusion polypeptide, the second portion is a therapeutic molecule. In some embodiments, the second portion is another anti-angiogenic molecule.

The polypeptides described herein can be fused with other anti-angiogenic factors and/or anti-VEGF agents as the second portion of a fusion protein, e.g., angiostatin or endostatin to enhance anti-angiogenic potency. Fusions or conjugates of such peptides have dual functions: activate p53 and induce Tsp-1 expression as well as anti-angiogenic activity. Methods of determining p53 activating activity and Tsp-1 expression inducing activity are described herein. Determining anti-angiogenic activities are well known to one skilled in the art, for example by, a chick chorioallantoic membrane assay.

The polypeptides, fusion polypeptides, multimers, and nucleic acids disclosed herein (e.g., used to prepare the compositions described herein) may be in a substantially purified form. This refers to the fact that the polypeptide or nucleic acid in a preparation in which more than 90%, e.g. 95%, 98% or 99% of the protein or nucleic acid in the preparation is the polypeptide or nucleic acid described herein.

In some embodiments, the polypeptide or fusion polypeptide composition described herein can be a differentially glycosylated form.

In some embodiments, the fusion polypeptide is 5, 6, 7, 8, 9, 10, 11, 12, 13, 14, 15, 16, 17, 18, 19, 20, 25, 30, 35, 40, 45, 50, 55, 60; 65, 70, 75, 80, 85, 90, 95, 100, 150, 200, 250, 300, 350, 400, 450, 500 or fewer amino acids in length.

Amino Acid Substitutions

Polypeptides that substantially retain the activity of the 4-6 mer, resulting from conservative amino acid substitution of the 4-6 mers described herein, are also envisioned. Conservative amino acid substitutions can be replacement of one amino acid residue with an amino acid residue having a side chain with a similar charge, size, polarity, hydrophobicity, or combination thereof. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Conservative amino acid substitutions typically do not change the overall structure of the peptide and/or the type of amino acid side chains available for forming van der Waals bonds with a binding partner. In some embodiments, a conservative substitution for Leucine is Valine.

In some embodiments, conservative or non-conservative substitutions for Leucine are contemplated. In some embodiments, the substitution for Leucine is Valine, Glycine or Alanine. In some embodiments, the substitution for Leucine is Glycine or Alanine. In some embodiments, the substitution for Leucine is Alanine. In some embodiments, a substitution for Leucine is Glycine. In some embodiments, a substitution for Leucine is Glycine or Valine. In some embodiments, a conservative substitution for Leucine is not Alanine.

In some embodiments, an amino acid substitution variant polypeptide or chimeric polypeptide consisting of 9 or fewer amino acid residues (e.g., 8, 7, 6, 5, or 4) comprising an Alanine substitution for Leucine is not: DWAPK (SEQ ID NO: 10), DWAPIK (SEQ ID NO: 48), DWAPIPK (SEQ ID NO: 49), DWAPIPCK (SEQ ID NO: 50), DWAPIPCSK (SEQ ID NO: 51), or DWAPIPCAK (SEQ ID NO: 52). In some embodiments, an amino acid substitution variant polypeptide consisting of 9 or fewer amino acid residues (e.g., 8, 7, 6, 5, or 4) comprising a substitution of Alanine for Leucine consists of 4 amino acids. In some embodiments, an amino acid substitution variant polypeptide consisting essentially of the amino acid sequence CDWLPK (SEQ ID NO: 3), DWLPK (SEQ ID NO: 4), or DWLP (SEQ ID NO: 5) is not: DWAPK (SEQ ID NO: 10). In some embodiments, an amino acid substitution variant polypeptide (a) consisting of 9 or fewer amino acid residues (e.g., 8, 7, 6, 5, or 4) or (b) consisting essentially of the amino acid sequence CDWLPK (SEQ ID NO: 3), DWLPK (SEQ ID NO: 4), or DWLP (SEQ ID NO: 5) comprising an Alanine substitution for Leucine is DWAP (SEQ ID NO: 6). In some embodiments, an amino acid substitution variant polypeptide or a chimeric polypeptide consisting of 10 or more amino acids comprising an Alanine substitution for Leucine is not: DWAPIPCSMK (SEQ ID NO: 53), DWAPIPCSLK (SEQ ID NO: 54), DWAPIPCASK (SEQ ID NO: 55), or QPLRHHQDWAPD (SEQ ID NO: 56). In some embodiments, an amino acid substitution variant polypeptide or a chimeric polypeptide consisting of 10 or more amino acids comprising a substitution of Alanine for Leucine consists of 11 amino acids. In some embodiments, an amino acid substitution variant polypeptide or a chimeric polypeptide consisting of 10 or more amino acids comprising a substitution of Alanine for Leucine consists of 11 or 13 or more amino acids. In some embodiments, an amino acid substitution variant polypeptide or chimeric polypeptide consisting of 9 or fewer amino acid residues (e.g., 8, 7, 6, 5, or 4) comprising a substitution of Alanine for Leucine is not a polypeptide as disclosed in U.S. Pat. No. 7,476,509 or 7,892,770 (both of which are incorporated herein by reference in their entirety). In some embodiments, an amino acid substitution variant polypeptide or a chimeric polypeptide consisting of 10 or more amino acids comprising a substitution of Alanine for Leucine is not a polypeptide as disclosed in U.S. Pat. No. 7,476,509 or 7,892,770.

In some embodiments, the amino acid substitution is a Tyrosine (Y) for a Tryptophan (W). In some embodiments, an amino acid substitution variant polypeptide consisting of 9 or fewer amino acid residues comprising a substitution of a Tyrosine (Y) for a Tryptophan (W) is not one of (or any of) SEQ ID NOs: 57-65. In some embodiments, an amino acid substitution variant polypeptide or chimeric polypeptide consisting of 9 or fewer amino acid residues (e.g., 8, 7, 6, 5, or 4) comprising a substitution of a Tyrosine (Y) for a Tryptophan (W) consists of 4-8 amino acid residues. In some embodiments, an amino acid substitution variant polypeptide or chimeric polypeptide consisting of 9 or fewer amino acid residues (e.g., 8, 7, 6, 5, or 4) comprising a substitution of a Tyrosine (Y) for a Tryptophan (W) is not 9 amino acid residues in length. In some embodiments, an amino acid substitution variant polypeptide or a chimeric polypeptide consisting of 10 or more amino acids comprising a substitution of a Tyrosine (Y) for a Tryptophan (W) is 11, 12, 13, 14, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more amino acids in length but less than 100, 150, 200, 250, 300, 350, 400, 450, or 500 amino acids in length. In some embodiments, an amino acid substitution variant polypeptide or a chimeric polypeptide consisting of 10 or more amino acids comprising a substitution of a Tyrosine (Y) for a Tryptophan (W) does not consist of 10, 15, 107, 178, 253, 322, or 328 amino acid residues. In some embodiments, an amino acid substitution variant polypeptide or a chimeric polypeptide consisting of 10 or more amino acids comprising a substitution of a Tyrosine (Y) for a Tryptophan (W) is not one of (or any of) SEQ ID NOs: 66-123. In some embodiments, an amino acid substitution variant polypeptide or a chimeric polypeptide consisting of 10 or more amino acids comprising a substitution of a Tyrosine (Y) for a Tryptophan (W) is not a full length 158P3D2 protein, a variant thereof, or a fragment thereof as described in U.S. Pat. No. 7,811,575 (which is incorporated herein by reference in its entirety). In some embodiments, an amino acid substitution variant polypeptide or chimeric polypeptide consisting of 9 or fewer amino acid residues (e.g., 8, 7, 6, 5, or 4) comprising a substitution of a Tyrosine (Y) for a Tryptophan (W) is not a polypeptide as disclosed in U.S. Pat. No. 7,811,575, 7,005,503, or 5,948,763 (which are incorporated herein by reference in their entirety). In some embodiments, an amino acid substitution variant polypeptide or a chimeric polypeptide consisting of 10 or more amino acids comprising a substitution of a Tyrosine (Y) for a Tryptophan (W) is not a polypeptide as disclosed in U.S. Pat. Nos. 7,811,575, 7,005,503, or U.S. Pat. No. 5,948,763.

Amino acid substitution can be achieved during chemical synthesis of the peptide by adding the desired substitute amino acid at the appropriate sequence in the synthesis process. Alternatively, molecular biology methods can be used. Non-conservative substitutions are also encompassed to the extent that they substantially retain the activities of those peptides described herein.

The amino acid substituted polypeptide will substantially retain the activity of the non-substituted polypeptide. By "substantially retain" means one or more activity of the variant is at least 50% compared to the activity of the original polypeptide in a similar assay, under similar conditions; preferably the activity is at least 60%, at least 70%, at least 80%, at least 90%, at least 95%, at least 99%, at least 100%, at least 2-fold, at least 5-fold, at least 10-fold, at least 100-fold or higher activity compared to the original polypeptide.

In some aspects, the disclosure relates to a isolated polypeptide consisting of 9 or fewer consecutive amino acid residues (e.g., 8, 7, 6, 5, or 4) comprising the active core amino acid sequence DWLP, or an amino acid substitution variant thereof, wherein the amino acid substitution is a) Tyrosine (Y) for Tryptophan (W); b) a conservative amino acid substitution for Leucine (L); c) a D-isomer of Aspartic Acid (D) for an L-isomer of Aspartic Acid (D) and/or a D-isomer of Leucine (L) for a L-isomer of Leucine (L); d) a D-isomer of Tryptophan (W) for an L-isomer of Tryptophan (W) and/or a D-isomer of Proline (P) for an L-isomer of Proline (P); or e) Alanine (A) or Glycine (G) for Leucine (L). In some embodiments, the amino acid substitution is a) Tyrosine (Y) for Tryptophan (W); c) a D-isomer of Aspartic Acid (D) for an L-isomer of Aspartic Acid (D) and/or a D-isomer of Leucine (L) for a L-isomer of Leucine (L); or d) a D-isomer of Tryptophan (W) for an L-isomer of Tryptophan (W) and/or a D-isomer of Proline (P) for an L-isomer of Proline (P). In some embodiments, the amino acid substitution is Tyrosine (Y) for Tryptophan (W). In some embodiments, the amino acid substitution is a conservative amino acid substitution for Leucine (L) or Alanine (A) or Glycine (G) for Leucine (L). In some embodiments, the amino acid substitution is a conservative amino acid substitution for Leucine (L). In some embodiments, the amino acid substitution is c) a D-isomer of Aspartic Acid (D) for an L-isomer of Aspartic Acid (D) and/or a D-isomer of Leucine (L) for a L-isomer of Leucine (L), or d) a D-isomer of Tryptophan (W) for an L-isomer of Tryptophan (W) and/or a D-isomer of Proline (P) for an L-isomer of Proline (P). In some embodiments, the amino acid substitution is a D-isomer of Aspartic Acid (D) for an L-isomer of Aspartic Acid (D) and/or a D-isomer of Leucine (L) for a L-isomer of Leucine (L). In some embodiments, the amino acid substitution is a D-isomer of Tryptophan (W) for an L-isomer of Tryptophan (W) and/or a D-isomer of Proline (P) for an L-isomer of Proline (P).

Modifications and Derivatives

The polypeptides described herein can further be modified or derivatized. The modified or derivatized polypeptides will typically substantially retain the activity of the base polypeptide (pre-modified/derivatized). Examples of modifications and derivatives are pegylation, glycosylation, acetylation, amidation, and phosphorylation. Methods of acetylation (e.g., N-terminal acetylation) and amidation (e.g., C-terminal amidation) are well known to those of skill in the art. Modifications, derivatives and methods of derivatizing polypeptides are described in Published International Application WO 2010/014616, the contents of which are incorporated herein by reference.

The polypeptides described herein can be conjugated or otherwise covalently attached to other molecules (e.g., using a chemical linker). One such form of attachment is through a non-amide linkage (e.g., a disulfide bond). In some embodiments, the polypeptide or fusion polypeptide is linked to a polymer that enhances the serum half-life of the first portion. In some embodiments, the polypeptide is covalently attached (e.g., via a linker molecule) to an antibody or a domain thereof suitable for enhancing the half-life of the molecule (e.g., one or more constant domains in an Fc domain). In some embodiments, the polypeptide is linked to an Fc domain (e.g., IgG, IgA, IgM, IgD, or IgE).

In some embodiments, the polypeptide of the present disclosure is linked to a non-amino acid polymer. Polymers such as polyethylene glycol can be used for the purpose of enhancing the serum half-life. Suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Such a polymer may or may not have its own biological activity. The polymers can be covalently or non-covalently conjugated to the polypeptide. Methods of conjugation for increasing serum half-life and for radiotherapy are known in the art, for example, in U.S. Pat. Nos. 5,180,816, 6,423,685, 6,884,780, and 7,022,673, which are hereby incorporated by reference in their entirety.

In some embodiments, the polypeptide is conjugated to a therapeutic molecule. In some embodiments, the therapeutic molecule is an anti-angiogenic therapeutic molecule, e.g., angiostatin and endostatin. Numerous anti-angiogenic therapeutic molecules are known in the art, including but not limited to bevacizumab sunitinib, thalidomide, lenalidomide and sorafenib. In some embodiments, the therapeutic molecule is an anti-VEGF agent. In another embodiment, the therapeutic molecule can be a toxin, a radiotherapy molecule or anti-cancer drug such as thalidomide and lenalidomide. Again, numerous anti-angiogenic therapeutic molecules are known in the art.

In some embodiments, the polypeptides described herein are modified by NH2-terminal acylation, e.g., acetylation, or thioglycolic acid amidation, by terminal-carboxylamidation, e.g., with ammonia, methylamine, and the like terminal modifications that are known in the art. Terminal modifications are useful to reduce susceptibility by proteinase digestion, and therefore serve to prolong half-life of the peptides in solutions, particularly biological fluids where proteases may be present. In some embodiments, any of the polypeptides described herein comprise an N-terminal acetyl group and/or a C terminal amide group. In some embodiments, any of the polypeptides herein comprise an N-terminal acetyl group and a C terminal amide group. In some embodiments, the polypeptide is Ac-dWlP-Amide or Ac-DWLP-Amide (Ac=acetyl group, lower case D and L indicate D-amino acids, SEQ ID NOs: 132 and 133, respectively).

In some embodiments, the polypeptide or fusion polypeptide described herein is linked to a polymer that enhances the serum half-life.

In some embodiments, the polypeptide or fusion polypeptide described herein is a cyclic peptide. Cyclic peptides (or cyclic proteins) are polypeptide chains whose amino and carboxyl termini are they linked together with a peptide bond or other covalent bond, forming a circular chain. In some embodiments, the polypeptide contains amino and carboxyl terminal cysteine amino acid residues. Cysteines facilitate S—S disulfide bond formation. In some embodiments, the polypeptide contains additional cysteine amino acid residues, wherein the cysteine amino acid residues are near the termini but not necessarily at the very end. In some embodiments, the cysteine amino acid residues are within five amino acid residues at the termini of the polypeptide. Methods of design and synthesis of cyclic peptides are well known in the art, e.g., as described in U.S. Pat. Nos. 5,596,078; 5,990,273; 7,589,170 and U.S. Patent Application No. 20080287649. A skilled artisan would be readily able to modify and apply the methods and techniques for the synthesis of a polypeptide described herein.

In some embodiments, the polypeptide or fusion polypeptide described herein, whether monomeric, oligomeric or cyclic, is PEGylated. PEGylation is the process of covalent attachment of Polyethylene glycol polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins. PEGylation, by increasing the molecular weight of a molecule, can impart several significant pharmacological advantages over the unmodified form, such as: improved drug solubility, reduced dosage frequency, without diminished efficacy with potentially reduced toxicity, extended circulating life, increased drug stability, and enhanced protection from proteolytic degradation. In addition, PEGylated drugs are have wider opportunities for new delivery formats and dosing regimens. Methods of PEGylating molecules, proteins and peptides are well known in the art, e.g., as described in U.S. Pat. Nos. 5,766,897; 7,610,156; 7,256,258 and the International Application No. WO/1998/032466.

In some embodiments, the polypeptides or fusion polypeptides described herein are further modified within the sequence, such as, modification by terminal-NH₂ acylation, e.g., acetylation, or thioglycolic acid amidation, by terminal-carboxylamidation, e.g., with ammonia, methylamine, and the like terminal modifications. Terminal modifications are useful, and are well known, to reduce susceptibility to proteinase digestion, and therefore serve to prolong half-life of the polypeptides in solutions, particularly biological fluids where proteases may be present.

All combinations of the different modifications and derivativizations are envisioned for the polypeptides and the fusion polypeptides and oligomer polypeptides described herein.

The various versions of polypeptides described herein, and modifications and derivatizations, encompassed by the present disclosure are expected to retain a significant amount of the biological activity exhibited by the 4-6 mers (e.g., as reported in the Examples section herein). In some embodiments, about 100% of the activity is retained in a given assay. In some embodiments, about 90%, 80%, 70%, 60% or 50% of the activity is retained. One such activity is the ability to stimulate expression of Tsp-1. Stimulation of expression is a significant, reproducible amount of increased expression that occurs from contact of the polypeptide described herein with an appropriate target cell, as compared to an identical or sufficiently similar target cell (control target cell) that has not been contacted with the polypeptide. Another such activity is the ability to activate p53. Another such activity is the ability to prevent angiogenesis in a model system or a subject. The methods for determining p53 activating activity and Tsp-1 expression induction activity are described herein and are also well known to one skilled in the art.

Another aspect of the disclosure relates to a peptide composition comprising repeating 4-6 mer units described herein, e.g., concamaterically linked units. The joining of a plurality of such units, such as by a molecular linker, results in an oligomer of polypeptides. In some embodiments, the oligomer is of a polypeptide consisting of, or consisting essentially of the 4-6 mer described herein. Such oligomer polypeptides can be further modified or derivatized as described herein. The composition can comprise an oligomeric polypeptide that is a dimer of two polypeptides, a trimer of three polypeptides, a tetramer of four polypeptides, or a pentamer of five polypeptides, etc. In some embodiments, the oligomeric polypeptide is a dimer of two polypeptides and/or a trimer of three polypeptides. In some embodiments, the oligomeric polypeptide is a homo-oligomericpolypeptide, comprising identical polypeptides according to the disclosure herein. Hetero-oligomeric peptides comprising different polypeptides are also contemplated.

In some embodiments, the molecular linker that joins the polypeptides to form an oligomeric polypeptide can be a peptide linker molecule or a chemical linker. The peptide linker molecule can comprise e.g., at least 2, 3, 4, 5, 6, 7, 8, 9, 10 or more amino acids residues and preferably less that 50 amino acids residues.

In some embodiments, the composition can also include the monomeric polypeptide along with an oligomeric peptide. It is contemplated that all possible combinations of monomeric, dimeric, trimeric, tetrameric, and pentameric polypeptides, and homo-oligomeric polypeptides as well as hetero-oligomeric polypeptides comprising the 4-6 mers described herein are potentially encompassed by the present disclosure.

In some embodiments, the molecular linker used for forming the oligomeric polypeptides is a peptide linker molecule. In some embodiments, the peptide linking molecule comprises at least one amino acid residue which links at least two peptides according to the disclosure. The peptide linker comprises, e.g., at least 2, 3, 4, 5, 6, 7, 8, 9, 10 or more amino acids residues and preferably less that 50 amino acids residues. The peptide linking molecule can couple polypeptides or proteins covalently or non-covalently. Typical amino acid residues used for linking are glycine, tyrosine, cysteine, lysine, glutamic and aspartic acid, or the like. A peptide linker is attached on its amino-terminal end to one peptide, polypeptide or polypeptide domain (e.g., a C-peptide) and on its carboxyl-terminal end to another peptide, polypeptide or polypeptide domain (again, e.g., a C-peptide). Examples of useful linker peptides include, but are not limited to, glycine polymers ((G)n) including glycine-serine and glycine-alanine polymers (e.g., a (Gly4Ser)n repeat where n=1-8, preferably, n=3, 4, 5, or 6). Other examples of peptide linker molecules are described in U.S. Pat. No. 5,856,456 and are hereby incorporated by reference.

In another embodiment, the molecular linker is a chemical linker such as linkages by disulfide bonds between cysteine amino acid residues or by chemical bridges formed by amine crosslinkers, for example, glutaraldehyde, bis(imido ester), bis(succinimidyl esters), diisocyanates and diacid chlorides. Extensive data on chemical cross-linking agents can be found at INVITROGEN's Molecular Probe under section 5.2.

In some embodiments, the oligomeric peptide can be made by linking individual isolated polypeptides. The individual polypeptides can be made by chemical methods known in the art or by recombinant methods also known in the art. For recombinant methods, the DNA coding sequence of a polypeptide can be made by amplification using the polymerase chain reaction (PCR). Specially designed PCR primers that incorporate restriction enzyme digestion sites and/or extra spacer or tag amino acid residues can be used to facilitate DNA ligation, recombinant protein expression, and protein purification. In order to facilitate linking of the polypeptides together, additional amino acid residues can be added, by way of the DNA coding sequence, to the polypeptides. For example, the thiol-group containing amino acid cysteine and the amine-group containing amino acid lysine can be added. The thiol-group and the amine group provide reactive groups useful for cross-linking reactions. In some embodiments, the additional amino acids are added at the ends of the polypeptides. The extra amino acids can be engineered into the coding sequence using standard recombinant molecular biology methods that are known in the art. In addition, extra amino acids that constitute a tag can be added to facilitate polypeptide expression and purifications. Examples of such tags include the thioredoxin first 105 amino acids, the tandem six histidine-tag, HA-tag, and the flag-tag.

The DNA sequences encoding the different individual polypeptides can be ligated into expression vectors which are then transfected into appropriate expression host cells and induced to express the recombinant peptide. Subsequently, the expressed recombinant peptide can be isolated (and optionally purified) and then used in cross-linking to form the dimeric, trimer, tetrameric, or pentameric oligomeric polypeptide compositions described herein by methods known in the art.

In the instance where the polypeptide contains no available reactive thiol-group for chemical cross-linking, several methods are available for introducing thiol-groups into proteins and peptides, including but not limited to the reduction of intrinsic disulfides, as well as the conversion of amine or carboxylic acid groups to thiol group. Such methods are known to one skilled in the art and there are many commercial kits for that purpose, such as from Molecular Probes division of Invitrogen Inc; and Pierce Biotechnology.

In another embodiment, the oligomeric peptide can be made by recombinant methods without the need for linking individual isolated polypeptides by chemical cross linking. Recombinant methods can be used to synthesize a single coding DNA sequence that comprises the several coding sequences of a peptide. For example, two and up to five coding sequences are ligated in tandem. Additional amino acid coding sequences, coding for, e.g., 2-10 amino acids, can be added between each pair of adjoining polypeptides as spacer sequences. When the single coding DNA is transcribed and translated, the expressed polypeptide can contain tandem repeats of peptides, each separated by, e.g., 2-10 extra amino acids. Typical amino acid residues used for spacing sequences are glycine, tyrosine, cysteine, lysine, proline, glutamic and aspartic acid, or the like. In a preferred embodiment, the oligomeric polypeptide is expressed in an amino-carboxyl-amino-carboxyl tandem configuration. Similarly, the oligomeric polypeptide synthesized can include a tag amino acid sequence for facilitating oligomeric polypeptide expression, identification and purifications. Such recombinant methods are well known to one skilled in the art.

Peptidomimetics

Also encompassed by the present disclosure are peptidomimetics based on the polypeptide sequences described herein (e.g., D-peptides, β peptides and peptoids). The peptidomimetics utilized can encompass the entire length of the peptide described herein, or only a portion of the peptide. In some embodiments, the peptide described herein is represented by a peptidomimetic and that mimic is covalently attached to a second polypeptide (e.g., a therapeutic molecule) as described herein.

In some embodiments the polypeptide is in the form of a peptidomimetic that is a peptoid (U.S. Pat. No. 5,811,387; Simon et al. Proceedings of the National Academy of Sciences USA, (1992), 89(20), 9367-9371). Peptoids are poly-N-substituted glycines. In peptoids the side chain is connected to the nitrogen of the peptide backbone, instead of the α-carbon as in peptides. Various peptoid modifications are being developed to adopt the secondary structure of peptide sequences. In some embodiments the peptoid contains nitroaromatic monomer units (Fowler et al., J Org Chem. 2009 Feb. 20; 74(4):1440-9). In some embodiments, the peptoid is N-substituted with alpha-chiral aromatic side chains (Gorske et al., J Am Chem Soc. 2006 Nov. 8; 128(44):14378-87) at one or more residues.

Other Polypeptide Modifications

It is to be understood that modified versions of the peptides described herein are encompassed in the present disclosure. Conservative substitutions are discussed herein above. Non-conservative substitutions are encompassed to the extent that that they substantially retain the activities of those peptides. Modification to a polypeptide described herein can be performed as described in U.S. published application 20080090760 and/or U.S. published application 20060286636, each of which is incorporated herein by reference in its entirety. The following provides a non-limiting discussion of various other peptide modifications encompassed within the scope of the disclosure.

Encompassed by the present disclosure are chemical derivatives of a polypeptide described herein, so long as it substantially retains the activities of the non-derivatized polypeptide. A "chemical derivative" is a subset of peptide derivatives as described herein and refers to a subject polypeptide having one or more residues chemically derivatized by reaction of a functional side group. In addition to side group derivatizations, a chemical derivative can have one or more backbone modifications including alpha-amino substitutions such as N-methyl, N-ethyl, N-propyl and the like, and alpha-carbonyl substitutions such as thioester, thioamide, guanidino and the like. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. Also included as chemical derivatives are those peptides which contain one or more non-limiting, non-natural amino acids, examples include those available for peptide synthesis from commercial suppliers (e.g. Bachem Catalog, 2004 pp. 1-276). For examples: 4-hydroxyproline may be substituted for proline; 5-hydroxylysine may be substituted for lysine; 3-methylhistidine may be substituted for histidine; homoserine may be substituted for serine; ornithine may be substituted for lysine; β-alanine may be substituted for alanine; norleucine may be substituted for leucine; phenylglycine may be substituted for phenylalanine, and L-1,2,3,4-tetrahydronorharman-3-carboxylic acid or H-β-(3-Benzothienyl)-Ala-OH may be substituted for tryptophan.

In certain embodiments, chemical modifications to the peptide include, but are not limited to the inclusion of, alkyl, alkoxy, hydroxyalkyl, alkoxyalkyl, alkoxycarbonyl, alkenyl, alkynyl, cycloalkyl, amino, alkylamino, aminoalkyl, dialkylamino, aminodialkyl, halogen, heteroatom, carbocycle, carbocyclyl, carbocyclo, carbocyclic, aryl, aralkyl, aralkoxy, aryloxyalkyl, heterocycle, heterocyclyl, heterocyclic, heteroaryl, and/or aliphatic groups.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic C3-C12 hydrocarbons which are completely saturated or which contain one or more units of unsaturation, but which are not aromatic. Lower alkyl refers to an alkyl group containing 1-6 carbons.

The term "amino" refers to an NH2 group. The term "alkylamino" or "aminoalkyl" refers to an amino group wherein one of the hydrogen atoms is replaced by an alkyl group. The term "dialkylamino" or "aminodialkyl" refers to an amino group wherein the hydrogen atoms are replaced by alkyl groups, wherein the alkyl group may be the same or different. The term "halogen" means F, Cl, Br, or I. The term "heteroatom" means nitrogen, oxygen, or sulfur with a carbon ring structure and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR+(as in N-substituted pyrrolidinyl). The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having six to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Examples of heterocyclic rings include 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl, [1,3]-dioxalanyl, [1,3]-dithiolanyl, [1,3]-dioxanyl, 2-tetra-hydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzoxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquino-linyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on any unsaturated carbon atom of an aryl, heteroaryl, aralkyl, or heteroaralkyl group include a halogen, —R0, —OR0, —SR0, 1,2-methylene-dioxy, 1,2-ethylenedioxy, protected OH (such as acyloxy), phenyl (Ph), substituted Ph, —O(Ph), substituted —O(Ph), —CH2(Ph), substituted —CH2(Ph), CH2CH2(Ph), substituted —CH2CH2(Ph), —NO2, —CN, —N(R0)2, —NR0C(O)R0, NR0C(O)N(R0)2, NR0CO2R0, —NR0NR0C(O)R0, —NR0NR0C(O)N(R0)2, —NR0NR0C2R0, C(O)C(O)R0, C(O)CH2C(O)R0, —CO2R0, —C(O)R0, —C(O)N(R0)2, —OC(O)N(R0)2, S(O)2R0, —SO2N(R0)2, —S(O)R0, —NR0SO2N(R0)2, —NR0SO2R0, —C(=S)N(R0)2, C(=NH)N(R0)2, (CH2) yNHC(O)R0, and —(CH2)yNHC(O)CH(V—R0)(R0); wherein each R0 is independently selected from hydrogen, a substituted or unsubstituted aliphatic group, an unsubstituted heteroaryl or heterocyclic ring, phenyl (Ph), substituted Ph, O(Ph), substituted —O(Ph), —CH2 (Ph), or substituted —CH2(Ph); y is 0-6; and V is a linker group. Examples of substituents on the aliphatic group or the phenyl ring of R0 include amino, alkylamino, dialkylamino, aminocarbonyl, halogen, alkyl, alkyl aminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

An aliphatic group or a non-aromatic heterocyclic ring or a fused aryl or heteroaryl ring may contain one or more substituents. Examples of suitable substituents on any saturated carbon of an aliphatic group or of a non-aromatic heterocyclic ring or a fused aryl or heteroaryl ring include those listed above for the unsaturated carbon of an aryl or heteroaryl group and the following: =O, =S, =NNHR*, =NN(R*)2, =N—, =NNHC(O)R*, =NNHCO2(alkyl), =NNHS02 (alkyl), or =NR*, where each R* is independently selected from hydrogen, an unsubstituted aliphatic group, or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, di alkylaminocarbonyloxy, alkoxy, nitro, cyano, carboxy, alkoxycarbonyl, alkylcarbonyl, hydroxy, haloalkoxy, and haloalkyl.

Suitable substituents on the nitrogen of a non-aromatic heterocyclic ring include R+, —N(R+)2, —C(O)R+, —CO2R+, —C(O)C(O)R+, —C(O)CH2C(O)R+, —SO2R+, —SO2N(R+)2, C(=S)N(R+)2, —C(=NH)—N (R+)2, and —NR+SO2R+; wherein each R+ is independently selected from hydrogen, an aliphatic group, a substituted aliphatic group, phenyl (Ph), substituted Ph, —O(Ph), substituted —O(Ph), —CH2(Ph), substituted —CH2(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

In certain embodiments, the peptide monomers described herein are dimerized or multimerized by covalent attachment to at least one linker moiety. The linker moiety is preferably, although not necessarily, a C1-12 linking moiety optionally terminated with one or two —NH— linkages and optionally substituted at one or more available carbon atoms with a lower alkyl substituent. Preferably the linker comprises —NH—R—NH— wherein R is a lower (C1-6) alkylene substituted with a functional group, such as a carboxyl group or an amino group, that enables binding to another molecular moiety (e.g., as may be present on the surface of a solid support during peptide synthesis or to a pharmacokinetic-modifying agent such as PEG). In certain embodiments the linker is a lysine residue. In certain other embodiments, the linker bridges the C-termini of two peptide monomers, by simultaneous attachment to the C-terminal amino acid of each monomer. In other embodiments, the linker bridges the peptides by attaching to the side chains of amino acids not at the C-termini. When the linker attaches to a side chain of an amino acid not at the C-termini of the peptides, the side chain preferably contains an amine, such as those found in lysine, and the linker contains two or more carboxy groups capable of forming an amide bond with the peptides.

The peptide monomers of the disclosure may be oligomerized using the biotin/streptavidin system. Oligomerization can enhance one or more activities of peptides as described herein. Biotinylated analogs of peptide monomers may be synthesized by standard techniques known to those skilled in the art. For example, the peptide monomers may be C-terminally biotinylated. These biotinylated monomers are then oligomerized by incubation with streptavidin (e.g., at a 4:1 molar ratio at room temperature in phosphate buffered saline (PBS) or HEPES-buffered RPMI medium (Invitrogen) for 1 hour). In a variation of this process, biotinylated peptide monomers may be oligomerized by incubation with any one of a number of commercially available anti-biotin antibodies [e.g., goat anti-biotin IgG from Kirkegaard & Perry Laboratories, Inc. (Washington, D.C.)].

In some aspects, the polypeptides described herein can be linked physically in tandem to form a polymer. The polypeptides making up such a polymer can be spaced apart from each other by a peptide linker. A "peptide linker" is a short (e.g., about 1-40, e.g., 1-20 amino acids) sequence of amino acids that is not part of the flanking Saposin A sequence. A linker peptide is attached on its amino-terminal end to one polypeptide or polypeptide domain and on its carboxyl-terminal end to another polypeptide or polypeptide domain. Examples of useful linker peptides include, but are not limited to, glycine polymers ((G)n) including glycine-serine and glycine-alanine polymers (e.g., a (Gly4Ser)n repeat where n=1-8, preferably, n=3, 4, 5, or 6). The polypeptides described herein can also be joined by chemical bond linkages, such as linkages by disulfide bonds or by chemical bridges. Molecular biology techniques that are well known to those skilled in the art can be used to create a polymer of the polypeptides. In some embodiments, combination of a polypeptide and variant peptide is found in the polymer. Peptide sequences of the present disclosure can also be linked together using non-peptide cross-linkers (Pierce 2003-2004 Applications Handbook and Catalog, Chapter 6) or other scaffolds such as HPMA, polydextran, polysaccharides, ethylene-glycol, poly-ethylene-glycol, glycerol, sugars, and sugar alcohols (e.g. sorbitol, mannitol).

In some embodiments, polyethylene glycol (PEG) may serve as a linker that dimerizes two polypeptide monomers: for example, a single PEG moiety containing two reactive functional groups may be simultaneously attached to the N-termini of both peptide chains of a peptide dimer. These peptides are referred to herein as "PEG linked peptides." In yet another embodiment, a linker moiety may comprise a molecule containing two carboxylic acids and optionally substituted at one or more available atoms with an additional functional group such as an amine capable of being bound to one or more PEG molecules. Such a molecule can be depicted as: —CO—(CH2)n-uX—(CH2)m-CO— where n is an integer between zero and 10, m is an integer between one and 10, X is selected from O, S, N(CH2)pNR1, NCO (CH2)pNR1, and CHNR1, R1 is selected from H, Boc (tert-butyloxycarbonyl), Cbz, and p is an integer between 1 and 10. In certain embodiments, one amino group of each of the peptides forms an amide bond with the linker. In certain other embodiments, the amino group of the peptide bound to the linker is the epsilon amine of a lysine residue or the alpha amine of the N-terminal residue, or an amino group of an optional spacer molecule. In some embodiments, a linker is used to cyclize peptides. In another embodiment, a spacer can be used in addition to a linker molecule for separating moieties as desired. In some embodiments, both n and m are one, X is NCO(CH2)pNR1, p is two, and R1 is Boc. Optionally, the Boc group can be removed to liberate a reactive amine group capable of forming a covalent bond with a suitably activated PEG species such as mPEG-SPA-NHS or mPEG-NPC (Nektar Therapeutics, San Carlos Calif.). Optionally, the linker contains more than one reactive amine capable of being derivatized with a suitably activated PEG species. Optionally, the linker contains one or more reactive amines capable of being derivatized with a suitably activated pharmacokinetic (PK) modifying agent such as a fatty acid, a homing peptide, a transport agent, a cell-penetrating agent, an organ-targeting agent, or a chelating agent.

A polypeptide monomer, dimer, multimer or oligomer as described herein may further comprise one or more linker and/or spacer moieties. In some embodiments, the linker moiety is a C1-12 linking moiety optionally terminated with —NH— linkages or carboxyl (—COOH) groups, and optionally substituted at one or more available carbon atoms with a lower alkyl substituent. In some embodiments, the linker is R—COOH wherein R is a lower (C1-6) alkyl optionally substituted with a functional group such as a carboxyl group or an amino group that enables binding to another molecular moiety. For example, the linker may be a glycine (G) residue, or an amino hexanoic acid (Ahx) such as 6-amino hexanoic acid. In other embodiments, the linker is —NH—R—NH— wherein R is a lower (C1-6) alkyl substituted with a functional group such as a carboxyl group or an amino group that enables binding to another molecular moiety. For example, the linker may be a lysine (K) residue or a lysine amide (K—NH2, a lysine residue wherein the carboxyl group has been converted to an amide moiety —CONH2).

In some embodiments, the linker moiety has the following structure: —NH—(CH2)a-[O—(CH2)b]g-O d-(CH2)e-Y— where a, b, g, d, and e are each integers whose values are independently selected. In some embodiments, a, b, and e are each integers whose values are independently selected between one and about six, d is zero or one, g is an integer selected between zero and about ten, except that when g is greater than one, b is two, and Y is selected from NH or CO. In some embodiments, a, b, and e are each equal to two, both g and d are equal to 1, and Y is NH. In another embodiment, g and d are zero, a and e together equal five, and Y is CO.

The polypeptide monomers, dimers, or multimers as described herein may further comprise one or more water soluble polymer moieties. Preferably, these polymers are covalently attached to the peptide compounds of the disclosure. Preferably, for therapeutic use of the end product preparation, the polymer is pharmaceutically acceptable. One skilled in the art will be able to select the desired polymer based on such considerations as whether the polymer-peptide conjugate will be used therapeutically, and if so, the desired dosage, circulation time, resistance to proteolysis, and other considerations. The water soluble polymer may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl-pyrrolidone) polyethylene glycol, propropylene glycol homopolymers, polypropylene oxide/ethylene oxide copolymers, and polyoxyethylated polyols. A preferred water soluble polymer is PEG.

The polymer may be of any molecular weight, and may be branched or unbranched. A preferred PEG for use in the present disclosure is linear, unbranched PEG having a molecular weight of from about 5 kilodaltons (kDa) to about 60 kDa (the term "about" indicating that in preparations of PEG, some molecules will weigh more, and some less, than the stated molecular weight). More preferably, the PEG has a molecular weight of from about 10 kDa to about 40 kDa, and even more preferably, the PEG has a molecular weight from 20 to 30 kDa. Other sizes may be used, depending on the desired therapeutic profile (e.g., duration of sustained release desired; effects, if any, on biological activity; ease in handling; degree or lack of antigenicity; and other effects of PEG on a therapeutic peptide known to one skilled in the art).

The number of polymer molecules attached may vary; for example, one, two, three, or more water-soluble polymers may be attached to a peptide of the disclosure. The multiple attached polymers may be the same or different chemical moieties (e.g., PEGs of different molecular weight).

In certain embodiments, PEG may be attached to at least one terminus (N-terminus or C-terminus) of a peptide monomer or dimer. In other embodiments, PEG may be attached to a linker moiety of a peptide monomer or dimer. In a preferred embodiment, PEG is attached to the linker moiety of a peptide dimer. Optionally, the linker contains more than one reactive amine capable of being derivatized with a suitably activated PEG species.

Methods for stabilizing peptides known in the art may be used with the methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described by Hirschmann et al. (J. Med. Chem., 1996, 36, 2441-2448, which is incorporated herein by reference in its entirety). Further, pyrrolinone-based peptide mimetics present the peptide pharmacophore on a stable background that has improved bioavailability characteristics (see, for example, Smith et al., J. Am. Chem. Soc. 2000, 122, 11037-11038), which is incorporated herein by reference in its entirety.

Encompassed herein are conjugates of the polypeptide described herein or of a conservative amino acid substitution variant or derivative thereof. These peptides can be conjugated to other polymers in addition to polyethylene glycol (PEG). The polymer may or may not have its own biological activity. Further examples of polymer conjugation include but are not limited to polymers such as polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Conjugation to a polymer can improve serum half-life, among other effects. A variety of chelating agents can be used to conjugate the peptides described herein. These chelating agents include but are not limited to ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis(hydroxybenzyl)ethylenediamine-N,N'-diacetic acid (HBED), triethylenetetraminehexaacetic acid (TTHA), 1,4,7,10-tetra-azacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA). Methods of conjugation are well known in the art, for example, P. E. Thorpe, et. al, 1978, Nature 271, 752-755; Harokopakis E., et. al., 1995, Journal of Immunological Methods, 185:31-42; S. F. Atkinson, et. al., 2001, J. Biol. Chem., 276:27930-27935; and U.S. Pat. Nos. 5,601,825, 5,180,816, 6,423,685, 6,706,252, 6,884,780, and 7,022,673, which are hereby incorporated by reference in their entirety.

In some embodiments, the polypeptides, fusion proteins or conjugates described herein include modifications within the sequence, such as, modification by terminal-NH2 acylation, e.g., acetylation, or thioglycolic acid amidation, by terminal-carboxylamidation, e.g., with ammonia, methylamine, and the like terminal modifications.

One can also modify the amino and/or carboxy termini of the peptides described herein. Terminal modifications are useful, to reduce susceptibility by proteinase digestion, and therefore can serve to prolong half-life of the polypeptides in solution, particularly in biological fluids where proteases may be present. Amino terminus modifications include methylation (e.g., —NHCH3 or —N(CH3)2), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—SO2-, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In certain embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U. S. Patent Application No. 20090035814; Muralidharan and Muir, 2006, Nat Methods, 3:429-38; and Lockless and Muir, 2009, Proc Natl Acad Sci USA. June 18, Epub. C-terminal functional groups of the peptides described herein include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the genetically encoded amino acids (or the stereoisomeric D amino acids) with other side chains, for instance with groups such as alkyl, lower (C1-6) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocycles. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods (e.g., as described in Hruby, et al. (1990) Biochem J. 268:249-262).

The polypeptide compounds described herein also serve as structural models for non-peptidic compounds with similar biological activity. Those of skill in the art recognize that a variety of techniques are available for constructing compounds with the same or similar desired biological activity as the 4-6 mer described herein, but with more favorable activity than the 4-6 mers with respect to solubility, stability, and susceptibility to hydrolysis and proteolysis (See, Morgan and Gainor (1989) Ann. Rep. Med. Chem. 24:243-252). These techniques include, but are not limited to, replacing the peptide backbone with a backbone composed of phosphonates, amidates, carbamates, sulfonamides, secondary amines, and N-methylamino acids.

Larger Polypeptides

Another aspect of the disclosure relates to the findings that polypeptides derived from Saposin A that contain the core 4-6 mers described herein, and are 9 or less consecutive amino acid residues (e.g., 8, 7, 6, 5, or 4) of the native Saposin A sequence, exhibit one or more of the activities of stimulating p53, stimulating Tsp-1 expression, inhibiting angiogenesis, inhibiting tumor growth, inhibiting tumor invasiveness, and inhibiting tumor metastasis. As such, some embodiments of the disclosure relate to a polypeptide consisting of 9 or fewer consecutive amino acid residues (e.g., 8, 7, 6, 5, or 4) comprising the active core amino acid sequence DWLP (SEQ ID NO: 5), DWLPK (SEQ ID NO: 4), or CDWLPK (SEQ ID NO: 3), or an amino acid substitution variant thereof. In some embodiments, the disclosure relates to a polypeptide consisting of 9 or fewer consecutive amino acid residues (e.g., 8, 7, 6, 5, or 4) comprising the active core amino acid sequence DWLP (SEQ ID NO: 5) or DWLPK (SEQ ID NO: 4), or an amino acid substitution variant thereof. In some embodiments, the disclosure relates to a polypeptide consisting of 9 or fewer consecutive amino acid residues (e.g., 8, 7, 6, 5, or 4) comprising the active core amino acid sequence DWLP (SEQ ID NO: 5), or an amino acid substitution variant thereof. The polypeptide has one or more of the activities of stimulating p53, stimulating Tsp-1 expression, inhibiting angiogenesis, inhibiting tumor growth, inhibiting tumor invasiveness, and inhibiting tumor metastasis, as determined by the methods described herein. Some embodiments of the disclosure relates to a polypeptide consisting of 9 or fewer consecutive amino acid residues comprising an active core which is an amino acid substitution variant of the amino acid sequence DWLP (SEQ ID NO: 5), DWLPK (SEQ ID NO: 4), or CDWLPK (SEQ ID NO: 3). In some embodiments, the disclosure relates to a polypeptide consisting of 9 or fewer consecutive amino acid residues (e.g., 8, 7, 6, 5, or 4) comprising the active core amino acid sequence DWLP (SEQ ID NO: 5) or DWLPK (SEQ ID NO: 4). In some embodiments, the disclosure relates to a polypeptide consisting of 9 or fewer consecutive amino acid residues (e.g., 8, 7, 6, 5, or 4) comprising the active core amino acid sequence DWLP (SEQ ID NO: 5). Specific amino acid substitutions are described herein. The polypeptide has one or more of the activities of stimulating p53, stimulating Tsp-1 expression, inhibiting angiogenesis, inhibiting tumor growth, inhibiting tumor invasiveness, and inhibiting tumor metastasis, as determined by the methods described herein.

Examples of such a polypeptide include, without limitation, DWLPKPNMS (SEQ ID NO: 12), CDWLPKPNM (SEQ ID NO: 13), TCDWLPKPN (SEQ ID NO: 14), KTCDWLPKP (SEQ ID NO: 15), EKTCDWLPK (SEQ ID NO: 16), and LEKTCDWLP (SEQ ID NO: 17). Other examples include, without limitation, DWLPKPNM (SEQ ID NO: 18), CDWLPKPN (SEQ ID NO: 19), TCDWLPKP (SEQ ID NO: 20), KTCDWLPK (SEQ ID NO: 21), EKTCDWLP (SEQ ID NO: 22), DWLPKPN (SEQ ID NO: 23), CDWLPKP (SEQ ID NO: 24), TCDWLPK (SEQ ID NO: 25), KTCDWLP (SEQ ID NO: 26), DWLPKP (SEQ ID NO: 27), CDWLPK (SEQ ID NO: 3), TCDWLP (SEQ ID NO: 28), DWLPK (SEQ ID NO: 4), CDWLP (SEQ ID NO: 29).

Also encompassed by the disclosure are the polypeptides of 9 or fewer amino acids (e.g., 8, 7, 6, 5, or 4) described herein, wherein the non-core sequences (the amino acids flanking the DWLP) have one or more amino acid substitutions (i.e., conservative, D-amino acid, and combinations thereof), wherein the polypeptide has one or more of the activities of stimulating p53, stimulating Tsp-1 expression, inhibiting angiogenesis, inhibiting tumor growth, inhibiting tumor invasiveness, and inhibiting tumor metastasis, as determined by the methods described herein.

The modifications to polypeptides described herein (e.g., amino acid substitutions, derivatizations, etc.) can be equally applied to this polypeptide of 9 or fewer amino acid residues (e.g., 8, 7, 6, 5, or 4). Fusion proteins, chimeric proteins, and other compositions (e.g., pharmaceutical compositions) described herein can similarly be made from this polypeptide of 9 or fewer amino acid residues (e.g., 8, 7, 6, 5, or 4) by the skilled practitioner. The 9 or fewer amino acid residues (e.g., 8, 7, 6, 5, or 4), fusion proteins and other compositions can further be used in the therapeutic methods described herein.

Pharmaceutical Compositions

Other aspects of the disclosure relate to compositions comprising the polypeptides and nucleic acids described herein. Such a composition (e.g., a pharmaceutical composition) may comprise a polypeptide, fusion polypeptide, oligomeric polypeptide, nucleic acid or vector comprising the nucleic acid, described herein. Pharmaceutical compositions comprising a polypeptide, fusion polypeptide, oligomeric polypeptide, nucleic acid or vector comprising the nucleic acid, described herein, can be used in various treatment methods.

Treatment Methods

A pharmaceutical composition comprising one or more of the various polypeptides described herein retains the activity of the 4-6 mers contained therein, and as such is useful for at least the following: (1) the treatment of an angiogenesis-dependent disease or disorder; (2) the treatment of cancer; (3) the inhibition of the recurrence of an angiogenesis-dependent disease or disorder; (4) the inhibition of the recurrence of cancer; (5) the inhibition of metastasis of cancer in a subject diagnosed with cancer; (6) the inhibition of recurrence of cancer in a subject diagnosed with cancer; (7) the inhibition of cancer development in a subject at risk of development of cancer; (8) the inhibition of cancer metastasis in a subject previously diagnosed with cancer; (9) the inhibition of the development of cancer malignancy in a subject previously diagnosed with cancer; (10) the inhibition of angiogenesis in a subject in need thereof; and (11) the stimulation of Tsp-1 expression in a subject in need thereof. Without wishing to be bound by theory, administration is expected to lead to a significant increase in Tspl at the target site for the specific disease or disorder. Such a site is a site of angiogenesis that is associated with the disease or disorder and is considered harmful to the subject in the context of the disease or disorder. Examples are the primary tumor site, secondary tumor site, or potential secondary tumor site in a subject diagnosed with a tumor, as in cancer. Thus, again not wishing to be bound by theory, the treatment of an angiogenesis-dependent disease or disorder; the treatment of cancer; the inhibition of the recurrence of an angiogenesis-dependent disease or disorder; the inhibition of the recurrence of cancer; the inhibition of metastasis of cancer in a subject diagnosed with cancer; the inhibition of recurrence of cancer in a subject diagnosed with cancer; the inhibition of cancer development in a subject at risk of development of cancer; the inhibition of cancer metastasis in a subject previously diagnosed with cancer; and the inhibition of the development of cancer malignancy in a subject previously diagnosed with cancer may be achieved through stimulation of Tsp-1 and/or inhibition of angiogenesis.

As such, one aspect of the disclosure relates to the administration of a therapeutically effective amount of one or more of the described polypeptides (e.g., the 4-6 mers) in the form of a pharmaceutical composition to a subject for therapeutic purposes. Another aspect of the disclosure relates to the administration of therapeutically effective amount of the polypeptides described herein consisting essentially of the 4-6 mers, in the form of a pharmaceutical composition to a subject for therapeutic purposes. Another aspect of the disclosure relates to the administration of therapeutically effective amount of the fusion polypeptides described herein that contain the 4-6 mers, in the form of a pharmaceutical composition to a subject for therapeutic purposes. Another aspect of the disclosure relates to the administration of therapeutically effective amount of the nucleic acids described herein, in the form of a pharmaceutical composition to a subject for therapeutic purposes.

In some embodiments, the disclosure provides a method of treating an angiogenesis-dependent disease or disorder, the method comprising administering to a subject in need thereof a therapeutically effective amount of a pharmaceutical composition described herein.

In some embodiments, the disclosure provides a method of inhibiting the recurrence of an angiogenesis-dependent disease or disorder, the method comprising administering to a subject in need thereof, a therapeutically effective amount of pharmaceutical composition described herein.

The angiogenesis-dependent disease or disorder is selected from, but is not limited to, a group consisting of cancer, ascites formation, psoriasis, age-related macular degeneration, thyroid hyperplasia, preeclampsia, rheumatoid arthritis and osteoarthritis, Alzheimer's disease, obesity, pleural effusion, atherosclerosis, inflammatory bowel disease (IBD), endometriosis, diabetic/other retinopathies, neovascular glaucoma, age-related macular degeneration (ARMD), hemangiomas, and corneal neovascularization.

In some embodiments, the angiogenesis-dependent disease or disorder is cancer. In some embodiments the cancer is a cancer known to be responsive to p53 based therapeutics. In some embodiments, administration of the pharmaceutical composition blocks growth of a primary tumor, prevents or inhibits metastasis, or produces a combination of such effects thereof. One such use of the compositions described herein is to treat an inoperable primary tumor (inoperable due to tumor location or health of the subject) while also treating or preventing metastasis. Tumor types thought optimally responsive to such therapy are described herein, and include, without limitation, tumors with increased stromal content.

In some embodiments, the angiogenesis-dependent disease or disorder is cancer, where the rapidly dividing neoplastic cancer cells require an efficient blood supply to sustain their continual growth of the tumor. As used herein, cancer refers to any of various malignant neoplasms characterized by the proliferation of anaplastic cells that tend to invade surrounding tissue and metastasize to new body sites and also refers to the pathological condition characterized by such malignant neoplastic growths. The blood vessels provide conduits to metastasize and spread elsewhere in the body. Upon arrival at the metastatic site, the cancer cells then work on establishing a new blood supply network. Administration of the pharmaceutical composition described herein is expected to lead to the increase in the angiogenesis inhibitor Tsp-1 in the surrounding stroma of the tumor. As a result, in some embodiments, administration of the pharmaceutical composition inhibits angiogenesis. By inhibiting angiogenesis at the primary tumor site and secondary tumor site, embodiments of the disclosure serve to halt, prevent and limit the progression of the disease. Any solid tumor that requires an efficient blood supply to keep growing is a candidate target. For example, candidates for the treatment described herein include carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

In some embodiments, the angiogenesis-dependent disease or disorder is age-related macular degeneration. It is known that VEGF contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula.

In some embodiments, the angiogenic disease or disorder is diabetic retinopathy-abnormal blood vessel growth associated with diabetic eye diseases. The activation of Tsp-1 via prosaposin serves to antagonize VEGF, a substance naturally produced in the body that promotes blood vessel formation. Released by the retina (light-sensitive tissue in back of the eye) when normal blood vessels are damaged by tiny blood clots due to diabetes, VEGF turns on its receptor, igniting a chain reaction that culminates in new blood vessel growth. However, the backup blood vessels are faulty; they leak, bleed and encourage scar tissue that detaches the retina, resulting in severe loss of vision. Such growth is the hallmark of diabetic retinopathy, the leading cause of blindness among young people in developed countries. In some embodiments, the subject in need of treatment can be a mammal, such as a dog or a cat, preferably a human.

In some embodiments, the angiogenesis-dependent disease or disorder is rheumatoid arthritis. Rheumatoid arthritis (RA) is characterized by synovial tissue swelling, leucocyte ingress and angiogenesis, or new blood vessel growth. The disease is thought to occur as an immunological response to an as yet unidentified antigen. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognised as a key event in the formation and maintenance of the pannus in RA (Paleolog, E. M., 2002). Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis; leukocyte ingress could not occur (Koch, A. E., 2000). Disruption of the formation of new blood vessels would not only prevent delivery of nutrients to the inflammatory site, it could also reduce joint swelling due to the additional activity of VEGF, a potent pro-angiogenic factor in RA, as a vascular permeability factor.

In some embodiments, the angiogenesis-dependent disease or disorder is Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with anti-angiogenic effects, seem to prevent Alzheimer's disease and/or influence the outcome of AD patients: Therefore, it has been speculated that in AD angiogenesis in the brain vasculature may play an important role in AD. In Alzheimer's disease, the brain endothelium secretes the precursor substrate for the beta-amyloid plaque and a neurotoxic peptide that selectively kills cortical neurons. Moreover amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies can interfere with endothelial cell activation in AD (Schultheiss C., el. al., 2006; Grammas P., et al., 1999) and can be used for preventing and/or treating AD.

In some embodiments, the angiogenesis-dependent disease or disorder is obesity. It has been shown that the angiogenesis inhibitor, TNP-470 was able to prevent diet-induced and genetic obesity in mice (Ebba BrAkenhielm et al., Circulation Research, 2004, 94:1579). TNP-470 reduced vascularity in the adipose tissue, thereby inhibiting the rate of growth of the adipose tissue and obesity development.

In some embodiments, the angiogenesis-dependent disease or disorder is endometriosis. Excessive endometrial angiogenesis is proposed as an important mechanism in the pathogenesis of endometriosis (Healy, D L., et al., 1998). The endometrium of patients with endometriosis shows enhanced endothelial cell proliferation. Moreover there is an elevated expression of the cell adhesion molecule integrin vß3 in more blood vessels in the endometrium of women with endometriosis when compared with normal women. Strategies that inhibit angiogenesis can be used to treat endometriosis.

In some embodiments, the angiogenesis-dependent disease or disorder is inflammatory bowel disease (IBD). IBD is a group of inflammatory conditions of the colon and small intestine. The major types of IBD are Crohn's disease and ulcerative colitis. Accordingly, in some embodiments, the angiogenesis-dependent disease or disorder is a type of IBD, e.g., Crohn's disease. Several studies have shown alterations in vascular anatomy and physiology in inflammatory bowel disease (IBD), indicating an angiogenic aspect of the disease (see, e.g., Inflamm Bowel Dis. 2006 June; 12(6):515-23. Role of angiogenesis in inflammatory bowel disease. Koutroubakis I F, Tsiolakidou G, Karmiris K, Kouroumalis E A and World J Gastroenterol. 2011 Feb. 7; 17(5):578-93. Role of the endothelium in inflammatory bowel diseases. Cromer W E, Mathis J M, Granger D N, Chaitanya G V, Alexander J S.). Inflammation in IBD is thought to be at least partially dependent of angiogenesis (see, e.g., Gastroenterology. 2006 June; 130(7):2060-73. Angiogenesis as a novel component of inflammatory bowel disease pathogenesis. Danese S, Sans M, de la Motte C, Graziani C, West G, Phillips M H, Pola R, Rutella S, Willis J, Gasbarrini A, Fiocchi C). Patients with active Crohn's disease who were administered infliximab (an anti-TNF-α agent) were shown to have clinical remission, which was associated with a significant reduction of microvascular density (Am J Gastroenterol. 2011 April; 106(4):762-70. Infliximab therapy inhibits inflammation-induced angiogenesis in the mucosa of patients with Crohn's disease. Rutella S, Fiorino G, Vetrano S, Correale C, Spinelli A, Pagano N, Arena V, Maggiano N, Repici A, Malesci A, Danese S). The scientists who conducted the study proposed that treatment with infliximab ameliorated inflammation-driven angiogenesis in the gut mucosa and contributed to the therapeutic efficacy of blockade of TNF-α. Anti-angiogenic compounds have also been shown to be effective in treating animal models of IBD (see, e.g., U.S. Patent Publication 20090312243). Accordingly, strategies that inhibit angiogenesis can be used to treat IBD. The methods described herein can be applied to a variety of cancers (e.g., any carcinoma or sarcoma). For example, papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma, sinonasal undifferentiated carcinoma, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma, that are found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus.

In some embodiments, the method of treating cancer or inhibiting or preventing metastasis is performed promptly after the detection of cancer. As used herein, promptness refers to any time within one month of positive laboratory test results confirming presence of cancer cells. Diagnosis and detection of cancer cells are well known to one skilled in the art. Laboratory tests can be in the form of histology and/or biomarkers that are known in the art but are not limited to these examples. Some laboratory tests include testing for cancer biomarkers such as cancer antigen (CA) 15-3, carcinoembryonic antigen (CEA) and BER-2 for breast cancer, human papillomavirus (HPV) E6 and E7 oncoproteins for cervical cancer, alpha-fetoprotein (AFP), AFP fractions L3, P4/5, and the +II band, and ultrasonography for hepatocellular carcinoma (HCC), prostate-specific antigen (PSA) for prostate cancer, and serum CA-125 for ovarian and HCC. Tissue biopsy and histology are usually performed for confirmation and tissue typing of the original of cancer cell type.

In some embodiments, the disclosure provides a method of inhibiting metastasis of cancer in a subject diagnosed with cancer, the method comprising administering to a subject in need thereof, a therapeutically effective amount of a pharmaceutical composition described herein (e.g., comprising the polypeptide or chimerical polypeptide, or nucleic acid described herein). The subject can be diagnosed with a benign or malignant tumor. The pharmaceutical composition can be administered to inhibit the establishment of secondary tumor from the initially discovered benign or malignant tumor.

In some embodiments, the disclosure provides a method of inhibiting tumor growth (e.g., primary or secondary tumor) in a subject diagnosed with a tumor, the method comprising administering to a subject in need thereof, a therapeutically effective amount of a pharmaceutical composition described herein. The subject can be diagnosed with a benign or malignant tumor.

In some embodiments, the subject is a mammal, such as a dog or a cat, preferably a human, who has previously been diagnosed with cancer. The cancer can be benign or malignant, and it may or may not have metastasized. As used herein, individual and subject are used interchangeably.

In some embodiments, the disclosure provides a method of inhibiting recurrence of cancer in a subject diagnosed with cancer, the method comprises administering to a subject in need thereof, a therapeutically effective amount of pharmaceutical composition described herein. The subject can be diagnosed with a benign or malignant cancer. The pharmaceutical composition can be administered to inhibit the re-growth of the primary tumor, development of tumors not related to the primary tumor, and/or establishment of secondary tumors from the initially discovered benign or malignant tumor.

In some embodiments, the disclosure provides a method for reducing the likelihood of cancer development in a subject, the method comprising administering to a subject in need thereof, a therapeutically effective amount of pharmaceutical composition described herein. In some embodiments, the pharmaceutical composition can be administered to prevent the development of cancer, the development of metastasis, and/or the development of malignancy. For example, for a subject who is predisposed to, or at risk of developing cancer (e.g., family history of early onset colon-rectal cancer, previous exposure to hepatitis B or C, or the subject carries some gene mutations that are associated with certain cancer types, e.g., BRCA1 and BRCA2), the pharmaceutical composition described herein can be administered to the subject for inhibiting cancer development in this subject. For a subject who has been diagnosed with a benign tumor, the benign tumor can be removed by surgery. The pharmaceutical composition described herein can be administered to the subject for inhibiting any remaining existing benign tumor cells from developing into a malignant cancer as well as to inhibit the development of metastasis. For a subject who has been diagnosed with a malignant tumor, the pharmaceutical composition described herein can be administered to the subject for inhibiting the malignant tumor from further metastasis.

Accordingly, in some embodiments, the disclosure provides a method for reducing the likelihood of the tumor development in a subject at risk of development of tumor or cancer, the method comprises administering to a subject in need thereof, a therapeutically effective amount of a pharmaceutical composition described herein.

In another embodiment, the disclosure provides a method for reducing the likelihood of the development of tumor malignancy in a subject previously diagnosed with a tumor or cancer, the method comprises administering to a subject in need thereof, a therapeutically effective amount of a pharmaceutical composition described herein.

In another embodiment, the disclosure provides a method for reducing the likelihood of cancer metastasis in a subject previously diagnosed with cancer, the method comprises administering to a subject in need thereof, a therapeutically effective amount of a pharmaceutical composition described herein.

In some embodiments, the administration described herein is in conjunction with a p53 reactivation agent.

In some embodiments, the administration described herein is in conjunction with chemotherapy, radiation therapy, and/or a cytostatic agent.

In some embodiments, the administration described herein is in conjunction with an anti-VEGF agent or an anti-angiogenesis factor.

Accordingly, provided herein is a method of treating an angiogenesis-dependent disease or disorder, the method comprising administering to a subject in need thereof a therapeutically effective amount of a pharmaceutical composition described herein to thereby treat the disease or disorder.

In some embodiments, provided herein is a method of treating psoriasis, the method comprises administering to a subject in need thereof a therapeutically effective amount of a pharmaceutical composition described herein to thereby treat psoriasis.

In some embodiments, provided herein is a method of inhibiting the recurrence of an angiogenesis-dependent disease or disorder, the method comprising administering to a subject in need thereof a therapeutically effective amount of a pharmaceutical composition described herein to thereby inhibit the recurrence of the disease or disorder.

In some embodiments, provided herein is a method of inhibiting metastasis of cancer in a subject diagnosed with cancer, the method comprising administering to the subject in need thereof a therapeutically effective amount of a pharmaceutical composition described herein to thereby inhibit metastasis of cancer.

In another embodiment, the methods described herein can be used in combination with other treatment options available for the angiogenesis-dependent disease or disorder. For example, the treatment methods described herein can be administered in conjunction with chemotherapy, radiation therapy, and/or a cytostatic agent. The treatment methods described herein are administered in conjunction with anti-VEGF or anti-angiogenic factor, and/or p53 reactivation agent. Examples of cancer chemotherapeutic agents include, but are not limited to, irinotecan (CPT-11); erlotinib; gefitinib (Iressa™); imatinib mesylate (Gleevec); oxalipatin; anthracyclins-idarubicin and daunorubicin; doxorubicin; alkylating agents such as melphalan and chlorambucil; cis-platinum, methotrexate, and alkaloids such as vindesine and vinblastine. A cytostatic agent is any agent capable of inhibiting or suppressing cellular growth and multiplication. Examples of cytostatic agents used in the treatment of cancer are paclitaxel, 5-fluorouracil, 5-fluorouridine, mitomycin-C, doxorubicin, and zotarolimus. Other cancer therapeutics includes inhibitors of matrix metalloproteinases such as marimastat, growth factor antagonists, signal transduction inhibitors and protein kinase C inhibitors.

Another treatment option available for the angiogenesis-dependent disease or disorder is immunotherapy and/or cancer vaccines. The methods described herein can be used in combination with such treatment options as well.

In another embodiment, the pharmaceutical compositions described herein are administered in conjunction with an anti-VEGF agent. Some examples of anti-VEGF agents include bevacizumab (Avastin™), VEGF Trap, CP-547,632, AG13736, AG28262, SU5416, SU11248, SU6668, ZD-6474, ZD4190, CEP-7055, PKC 412, AEE788, AZD-2171, sorafenib, vatalanib, pegaptanib octasodium, IM862, DC101, angiozyme, Sima-027, caplostatin, neovastat, ranibizumab, thalidomide, and AGA-1470, a synthetic analog of fumagillin (alternate names: Amebacilin, Fugillin, Fumadil B, Fumadil) (A. G. Scientific, catalog # F1028), an angio-inhibitory compound secreted by *Aspergillus firinigates*.

As used herein the term "anti-VEGF agent" refers to any compound or agent that produces a direct effect on the signaling pathways that promote growth, proliferation and survival of a cell by inhibiting the function of the VEGF protein, including inhibiting the function of VEGF receptor proteins. The term "agent" or "compound" as used herein means any organic or inorganic molecule, including modified and unmodified nucleic acids such as antisense nucleic acids, RNAi agents such as siRNA or shRNA, peptides, peptidomimetics, receptors, ligands, and antibodies. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (Astra-Zeneca), ZD4190 which inhibits VEGF-R2 and -R1 (Astra-Zeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sima-027 (an siRNA-based VEGFR1 inhibitor, Sima Therapeutics, San Francisco, Calif.) Caplostatin, soluble ectodomains of the VEGF receptors, Neovastat (Æterna Zentaris Inc; Quebec City, Calif.) and combinations thereof.

Anti-angiogenesis factors or therapeutics include any agent that directly or indirectly inhibits, prevents, and stops angiogenesis and/or neovascularization. Anti-angiogenesis factors include anti-VEGF agent. Other anti-angiogenesis factors include, but are not limited to angiostatin, endostatin and cleaved antithrombin III, alpha-2 antiplasmin (fragment), angiostatin (plasminogen fragment), antiangiogenic antithrombin III, cartilage-derived inhibitor (CDI), CD59 complement fragment, endOstatin (collagen XVIII fragment), fibronectin fragment, gro-beta (a C—X—C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronectin (45 kD fragment), high molecular weight kininogen (domain 5), NK1, NK2, NK3 fragments of HGF, PF-4, serpin proteinase inhibitor 8, TGF-beta-1, p53, angioarrestin, metalloproteinase inhibitors (TIMPs), 2-Methoxyestradiol, placental ribonuclease inhibitor, plasminogen activator inhibitor, prolactin 16kD fragment, proliferin-related protein (PRP), retinoids, tetrahydrocortisol-S transforming growth factor-beta (TGF-β), vasculostatin, and vasostatin (calreticulin fragment), pamidronate thalidomide, TNP470, the bisphosphonate family such as amino-bisphosphonate zoledronic acid. bombesin/gastrin-releasing peptide (GRP) antagonists such as RC-3095 and RC-3940-II (Bajol A M, et al., British Journal of Cancer (2004) 90, 245-252), monoclonal antibody therapies directed against specific pro-angiogenic growth factors and/or their receptors: example: bevacizumab (AVASTIN®), cetuximab (ERBITUX®), panitumumab (VECTIBIX™), and trastuzumab (HERCEPTIN®); small molecule tyrosine kinase inhibitors (TKIs) of multiple pro-angiogenic growth factor receptors. The three TKIs that are currently approved as anti-cancer therapies are erlotinib (TARCEVA®), sorafenib (NEXAVAR®), and sunitinib (SUTENT®); and inhibitors of mTOR (mammalian target of rapamycin) such as temsirolimus (TORICEL™) bortezomib (VELCADE®), thalidomide (THALOMID®), and doxycyclin.

Methods of determining anti-VEGF activity and/or anti-angiogenesis activity are well known to one skilled in the art. For example, the human umbilical vein endothelial cell phosphorylation assay and the VEGF-induced proliferation assay as described by Holash et al., 2002, in Proc. Natl.

Acad. Sci. USA, 99:11393-98, can be used to determine the anti-VEGF inhibitory activity of an anti-VEGF agent and are hereby explicitly incorporated by reference. The human $VEGF_{165}$ can be used as the positive control in the cell phosphorylation and proliferation assays. The cell phosphorylation assay detects tyrosine phosphorylation which is an indicator of the activation of the VEGF signaling pathway. The proliferation assay detects cell proliferation induced by the activation of the VEGF signaling pathway. An anti-VEGF agent that blocks the activation of the VEGF signaling pathway will give reduced tyrosine phosphorylation and reduced cell proliferation in these assays compared to the results when the human $VEGF_{165}$ is used as a positive control.

In yet another embodiment, the pharmaceutical compositions described herein are administered in conjunction with a p53 reactivation agent. Around half of all human tumors carry p53 mutations, mostly point mutations that abrogate p53's specific DNA binding and transactivation activity. p53 mutation is associated with poor therapeutic response and prognosis. Tumors that carry wild type p53 often have other alterations in the p53 pathway that ablate the p53 tumor suppression response. Several strategies have been designed to restore p53 function in human tumors, including p53 gene therapy, reactivation of mutant p53, and activation of wild type p53 by inhibition of the p53 antagonist MDM2. In all cases, the aim is to eliminate the tumor through induction of massive apoptosis (Bykov V J and Wiman K G. 2003).

A p53 reactivation agent is any organic or inorganic chemical, compound, including protein and nucleic acid molecule that can restore the p53 response of a tumor cell. The p53 reactivation agent can be a gene therapy agent, such as a vector, carrying a wild-type p53 gene for reconstitution into tumor cells with deletions in the p53 gene, that is, introduction of an intact cDNA copy of the p53 gene using a suitable viral vector, typically one based on adenovirus (Adp53) (Wiman, 2006) or ADVEXIN (Introgen Inc.). The end result is to have functional p53 protein expression in the tumor cells. Functional p53 will perform the tumor suppression activities that are well known in the art.

Some cancer cells carry the wild-type p53 gene and should express theoretically functional p53 protein yet tumor growth is not regulated by the expressed p53 (Gurova, et al., 2004). It is speculated that p53 is somehow deactivated. A frequent observation in wild-type p53 gene carrying tumors is the overexpression of MDM2. The deactivation of p53 has been shown to be the result of MDM2-mediated p53 ubiquitination and the deregulation of HDM-2, which binds to p53 and targets it for proteasomal degradation. The deactivation of p53 has been shown to be also mediated by suppression of NF-κB activity as it was shown that p53 tumor suppressor activity was restored by ectopic expression of a super-repressor of IκB such as 9-aminoacridine (9AA), its derivatives, and the anti-malaria drug quinacrine (Gurova, et al., 2004). P53 reactivation agents that activate p53 by blocking the p53/MDM2 and the p53/HDM-2 protein-protein interactions to prevent p53 degradation are MDM-2 inhibitors and HDM-2 inhibitors. Some examples include a group of imidazoline compounds dubbed Nutlins (Vassilev L T et al., 2004) which fit neatly into the small pocket where MDM-2 contacts p53 and prevent the interaction between the two proteins.

Mutant p53 proteins have point mutations that abrogate p53's specific DNA binding and transactivation activity. These mutant p53 often fold abnormally and thus lose the ability to regulate their target genes. New small molecules that help these mutant p53 proteins fold more normally have been successful in reactivating the mutant p53 protein. Examples are the novel compounds RITA (Issaeva N., et al., 2004; Espinoza-Fonseca L M. 2005), the related PRIMA-1 and MIRA-1 (Rehman, A. 2005), and CP-31398 (Tanner S and Barberis A., 2004; Ho C K and Li G., 2005). For tumors with mutations in p53 that abolish the DNA binding activity in p53, a p53 reactivation agent can be one that facilitates DNA binding of the mutant p53 thus enabling the mutant p53 to function again as an activator of transcription. An example of such a p53 reactivation agent is described in Roth, J. et al., 2003, where a chimeric adaptor protein made of the DNA-binding and tetramerizing portions of the p53-homologue p73 (i.e., having tumor suppressive effects) fused to the oligomerization domain of p53 enables the mutant p53 to bind to its respective p53 response elements and initiate apoptosis. In addition, drugs that mimic p53's effects in activating gene transcription are also contemplated. Furthermore, agents that increase the production, expression, and/or stability of p73, the p53 homologue, can also be used in combination with the methods described herein. The increase of p73 production, expression, and/or stability in tumor cells serves to promote apoptosis.

Methods of assaying the effects of a polypeptide described herein on Tsp-1 and p53 expression are described herein. Briefly, a control Psap alongside a test polypeptide, is applied to a cell culture of prostate fibroblasts. The conditioned media from PC3M-LN4 (LN4) and PC3 cells are used as controls, with PC3 as positive/stimulating control and LN4 as negative/inhibiting controls. After a period of incubation (~16 h), the cells are harvested, rinsed, and lysed. The lysates are analyzed for the level of Tsp-1 and p53 expression by western blot analyses, with β-actin as the internal lysate protein loading control.

In yet another embodiment, the pharmaceutical compositions described herein are administered in conjunction with therapeutics, physiotherapy and/or behavioral psychotherapy used in the treatment of rheumatoid arthritis, obesity, endometriosis, and Alzheimer's disease.

For examples of treatments of rheumatoid arthritis, there are therapeutic drugs that decrease pain and local inflammation including aspirin and non-steroidal anti-inflammatory drugs or NSAIDS (such as ibuprofen or naproxen) and other immunosuppressive drugs that decrease pain and inflammation while decreasing the growth of abnormal synovial tissue (the tissue that lines the inside of the joint). These drugs include methotrexate and low doses of corticosteroids (such as prednisone or cortisone). Other medications used to treat rheumatoid arthritis include: anti-malarial medications (such as hydroxychloroquine), gold, sulfasalazine, penicillamine, cyclophosphamide, cyclosporine, minocycline, and interleukin receptor antagonist and anti-Il2 antibodies.

Treatment for Alzhemier's disease include, but are not be limited to, nonsteroidal anti-inflammatory drugs (NSAIDs), estrogen, steroids such as prednisone, vitamin E, menantine, donepezil, rivastigmine, tacrine, and galantamine. Holistic medicine include example such as gingko nuts extracts.

Treatment of endometriosis include, but should not be construed as limited to, a combination oral contraceptives (estrogen plus a progestin), progestins (such as medroxyprogesterone, danazol (a synthetic hormone related to testosterone, gonadotropin-releasing hormone agonists (GnRH agonists—such as buserelin, goserelin, leuprolide and nafarelin), and nonsteroidal anti-inflammatory drugs (NSAIDs) for pain control.

Examples of treatment options for obesity include dieting and nutritional counseling, exercise regime, gastric-bypass surgery, and drugs such as a combination of fenfluramine and phentermine (often called fen-phen), orlistat, sibutramine, phentermine, benzphetamine, diethylpropion, mazindol, and phendimetrazine.

Generation of Functional Peptides

Functional polypeptides described herein can be chemically synthesized and isolated by biochemical methods that are well known in the art such as solid phase peptide synthesis using t-Boc (tert-butyloxycarbonyl) or FMOC (9-flourenylmethloxycarbonyl) protection group described in "Peptide synthesis and applications" in Methods in molecular biology Vol. 298, Ed. by John Howl and "Chemistry of Peptide Synthesis" by N. Leo Benoiton, 2005, CRC Press, (ISBN-13: 978-1574444544) and "Chemical Approaches to the Synthesis of Peptides and Proteins" by P. Lloyd-Williams, et al., 1997, CRC-Press, (ISBN-13: 978-0849391422). Solid phase peptide synthesis, developed by R. B. Merrifield, 1963, J. Am. Chem. Soc. 85 (14): 2149-2154, was a major breakthrough allowing for the chemical synthesis of peptides and small proteins. An insoluble polymer support (resin) is used to anchor the peptide chain as each additional alpha-amino acid is attached. This polymer support is constructed of 20-50 μm diameter particles which are chemically inert to the reagents and solvents used in solid phase peptide synthesis. These particles swell extensively in solvents, which makes the linker arms more accessible.

Organic linkers attached to the polymer support activate the resin sites and strengthen the bond between the (-amino acid and the polymer support. Chloromethyl linkers, which were developed first, have been found to be unsatisfactory for longer peptides due to a decrease in step yields. The PAM (phenylacetamidomethyl) resin, because of the electron withdrawing power of the acid amide group on the phenylene ring, provides a much more stable bond than the classical resin. Another alternative resin for peptides under typical peptide synthesis conditions is the Wang resin. This resin is generally used with the FMOC labile protecting group.

A labile group protects the alpha-amino group of the amino acid. This group should be easily removed after each coupling reaction so that the next alpha-amino protected amino acid may be added. Typical labile protecting groups include t-Boc and FMOC t-Boc is a very satisfactory labile group which is stable at room temperature and easily removed with dilute solutions of trifluoroacetic acid (TFA) and dichloromethane. FMOC is a base labile protecting group which is easily removed by concentrated solutions of amines (usually 20-55% piperidine in N-methylpyrrolidone). When using FMOC alpha-amino acids, an acid labile (or base stable) resin, such as an ether resin, is desired.

The stable blocking group protects the reactive functional group of an amino acid and prevents formation of complicated secondary chains. This blocking group must remain attached throughout the synthesis and may be removed after completion of synthesis. When choosing a stable blocking group, the labile protecting group and the cleavage procedure to be used should be considered.

After generation of the resin bound synthetic peptide, the stable blocking groups are removed and the peptide is cleaved from the resin to produce a "free" peptide. In general, the stable blocking groups and organic linkers are labile to strong acids such as TFA. After the peptide is cleaved from the resin, the resin is washed away and the peptide is extracted with ether to remove unwanted materials such as the scavengers used in the cleavage reaction. The peptide is then frozen and lyophilized to produce the solid peptide. This is then characterized by HPLC and MALDI before being used. In addition, the peptide should be purified by HPLC to higher purity before use.

Commercial peptide synthesizing machines are available for solid phase peptide synthesis. For example, the Advanced Chemtech Model 396 Multiple Peptide Synthesizer and an Applied Biosystems Model 432A Peptide synthesizer. There are commercial companies that make custom synthetic peptide to order, e.g., Abbiotec, Abgent, AnaSpec Global Peptide Services, LLC., INVITROGEN™ and rPeptide, LLC.

Synthesis of Polypeptide Proteins

The polypeptides and fusion polypeptides described herein can be synthesized and isolated by molecular methods that are well known in the art. Generally, molecular biology methods and recombinant heterologous protein expression systems are used. For example, recombinant protein may be expressed in bacteria, mammal, insects, yeast, or plant cells. In some embodiments, the polypeptides described herein are isolated polypeptides. In some embodiments, the isolated polypeptides are purified polypeptides.

In some embodiments, the polypeptides and/or fusion polypeptides are produced from fragments of the full length prosaposin molecules. An example of expression, isolation, and purification of the human prosaposin is described in Gopalakrishnan, M. M., et al., 2004 and in U.S. Pat. No. 5,700,909. The purification of rat prosaposin is described in Morales, C R., 1998. These references are hereby incorporated by reference in their entirety. The approach can be applied to the purification of human Psap proteins by one skilled in the art.

Nucleic acid molecules encoding the polypeptides and/or fusion polypeptides described herein may be introduced into host cells (optionally in the form of vectors) to enable the expression of the encoded polypeptides. Alternatively, cell-free expression systems may be used. By using an appropriate expression system the polypeptides can be produced in a desired form. For example, the polypeptides can be produced by micro-organisms such as bacteria or yeast, by cultured insect cells (which may be baculovirus-infected), by mammalian cells (such as CHO cells) or by transgenic animals that, for instance, secrete the polypeptides in milk (see e.g. international patent application WO88/00239). Where glycosylation is desired, eukaryotic (e.g. mammalian or insect) expression systems are preferred.

The produced polypeptides and fusion polypeptides are to retain the TSP-1 expression stimulating activity and also may retain p53 expression stimulating activity. Verification that this activity is preserved can be performed following synthesis/purification. As used herein, the Tsp-1 and p53 expression stimulating activity refers to the ability to induce an increase in the expression levels of Tsp-1 and p53 in surrounding tumor stroma or fibroblast cells. The retained activity can also include effects on tumor and non-tumor cells observed with prosaposin and active fragments thereof. The detection of such activities is exemplified herein. Other such methods of detecting this activity can be devised by the skilled practitioner.

Encompassed in the disclosure is a vector carrying a cDNA encoding the polypeptides or fusion polypeptides described herein. Conventional polymerase chain reaction (PCR) cloning techniques can be used to generate the complete cDNA sequence, using, e.g., the PCR primers that flank the coding region of the polypeptides described herein in the corresponding full length prosaposin.

Specific primers can be designed to correspond to the desired coding region of the prosaposin cDNA. The cDNAs can be cloned into a general purpose cloning vector such as pUC19, pBR322, pBluescript vectors (Stratagene Inc.) or pCR TOPO® from Invitrogen Inc. For example, the cDNA can be subcloned into the vector pDNR-dual. The resultant recombinant vector carrying cDNA sequence can then be used for further molecular biological manipulations such as site-directed mutagenesis to generate the desired amino acid substitutions. The final nucleic acid products can be subcloned into protein expression vectors or viral vectors for protein synthesis in a variety of protein expression systems using host cells selected from the group consisting of mammalian cell lines, insect cell lines, yeast, and plant cells. In the example below, Cre recombinase to move the cDNA's into pCMVneo for expression.

Examples of other expression vectors and host cells are the pET vectors (Novagen), pGEX vectors (Amersham Pharmacia), and pMAL vectors (New England labs. Inc.) for protein expression in *E. coli* host cell such as BL21, BL21 (DE3) and AD494(DE3)pLysS, Rosetta (DE3), and Origami (DE3) (Novagen); the strong CMV promoter-based pcDNA3.1 (Invitrogen) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFastBac™ HT (Invitrogen) for the expression in *Spodopera frugiperda* 9 (Sf9) and Sf11 insect cell lines; pMT/BiP/V5-His (Invitrogen) for the expression in *Drosophila schneider* S2 cells; *Pichia* expression vectors pPICZα, pPICZ, pFLDα and pFLD (Invitrogen) for expression in *Pichia pastoris* and vectors pMETα and pMET for expression in *P. methanolica*; pYES2/GS and pYD1 (Invitrogen) vectors for expression in yeast *Saccharomyces cerevisiae*. Recent advances in the large scale expression heterologous proteins in *Chlamydomonas reinhardtii* are described by Griesbeck C. et al., 2006 Mol. Biotechnol. 34:213-33 and Fuhrmann M. 2004, Methods Mol Med. 94:191-5. Foreign heterologous coding sequences are inserted into the genome of the nucleus, chloroplast and mitochondria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduce the vector in the algae. Upon its entry into chloroplasts, the foreign DNA is released from the gene gun particles and integrates into the chloroplast genome through homologous recombination.

Specific site-directed mutagenesis of the appropriate Psap cDNA sequence in a vector can be used to create specific amino acid substitutions described herein. Site-directed mutagenesis can be carried out using the QUIKCHANGE® site-directed mutagenesis kit from Stratagene according to manufacture's instructions or any method known in the art.

In some embodiments, provided herein are expression vectors carrying the cDNA that encodes the polypeptide described herein for the expression and purification of the recombinant polypeptide produced from a eukaryotic protein expression system using host cells selected from the group consisting of mammal, insects, yeast, or plant cells.

Specifically contemplated in the methods described herein are fusion proteins. For example, the polypeptides described herein can be fused to transferrin, IgG, or albumin, to name a few, to enhance serum half life and pharmacokinetics in the individual being treated. polypeptides can also be fused to a tag protein such as tandem histidine residues (6xHis), GST, myc, thioredoxin first 105 amino acids or HA tag for the purification and/or enhance solubility of the expressed recombinant protein in heterologous system. Enzymatic digestion with serine proteases such as thrombin and enterokinase cleave and release the polypeptide from the histidine or myc tag, releasing the recombinant polypeptide from the affinity resin while the histidine-tags and myc-tags are left attached to the affinity resin.

A simplified system for generating recombinant adenoviruses is presented by He T C. et al., Proc. Natl. Acad. Sci. USA 95:2509-2514, 1998. The gene of interest is first cloned into a shuttle vector, e.g., pAdTrack-CMV. The resultant plasmid is linearized by digesting with restriction endonuclease Pme I, and subsequently co-transformed into *E. coli*. BJ5183 cells with an adenoviral backbone plasmid, e.g., pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenoviruses are generated within the HEK 293 cells.

In some embodiments, provided herein is a recombinant lentivirus for the delivery and expression of a polypeptide in either dividing or non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™ Lentiviral Expression systems from Invitrogen.

In some embodiments, the disclosure provides a recombinant adeno-associated virus (rAAV) vector for the expression of a polypeptide. In some embodiments, the rAAV vector encoding a polypeptide of the present disclosure is administered to slow, inhibit, or prevent the growth of cancer and tumors such as glioma. Using rAAV vectors, genes can be delivered into a wide range of host cells including many different human and non-human cell lines or tissues. Because AAV is non-pathogenic and does not elicit an immune response, a multitude of pre-clinical studies have reported excellent safety profiles. rAAVs are capable of transducing a broad range of cell types, and transduction is not dependent on active host cell division. High titers, >$10^8$ viral particles/ml, are easily obtained in the supernatant and $10^{11}$-$10^{12}$ viral particles/ml can be obtained with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying the Psap DNA coding sequence, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then isolated by two different methods depending on the serotype of the vector. AAV2 vector is isolated by the single-step gravity-flow column purification method based on its affinity for heparin (Auricchio, A., et al., 2001, Human Gene therapy 12:71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently isolated by three sequential CsCl gradients.

Therapeutic Compositions and Administration

In some embodiments, the disclosure provides for a pharmaceutical composition comprising a polypeptide or fusion polypeptide or nucleic acid (e.g., in an expression vector) described herein. In some embodiments, the pharmaceutical composition comprises the active ingredient in the form of a gene therapy virus (e.g., in the form of an adenovirus, adeno-associated virus or lentivirus).

As used herein, the term "pharmaceutical composition" refers to the formulation of the active agent (e.g., polypeptide, fusion polypeptide, or nucleic acid, etc. described herein) in combination with a pharmaceutically acceptable carrier. The pharmaceutical composition can further comprise additional agents (e.g. for specific delivery, increasing half-life, or other therapeutic agents). The pharmaceutical composition does not include tissue culture media, and serum.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the active agent ingredient from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the patient (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments of the methods described herein, the pharmaceutical composition comprises of a plurality of polypeptides described herein, wherein the polypeptides are not identical.

In some embodiments of the methods described herein, the pharmaceutical composition comprises a multimer of polypeptides described herein, wherein the peptides are identical. The polypeptides may be concatamerically linked.

When used in therapy, the pharmaceutical composition of the disclosure can be administered in any convenient vehicle that is physiologically acceptable. The route of administration will deliver an effective amount of the therapeutic composition to a site of potentially harmful angiogenesis. Appropriate routes of administrations are determined by the skilled practitioner.

The compounds can be formulated for a variety of modes of administration, including systemic, topical or localized administration. Techniques and formulations generally can be found in Remington's Pharmaceutical Sciences, Mack Publishing Co., Easton, Pa., latest edition. In each case, a therapeutically effective amount of the pharmaceutical composition is administered in order to inhibit the progression of, or relapse or recurrence of the disease or disorder. The polypeptide or nucleic acids are generally combined with a carrier, the form of which will depend on the nature of the mode of administration and dosage forms. Typical dosage forms include tablets, powders, liquid preparations including suspensions, emulsions and solutions, granules, capsules and suppositories, as well as liquid preparations for injections.

Administration of the pharmaceutical compositions described herein is performed to deliver the active ingredient to the desired location(s) in the body of a subject (e.g., a place where inhibition of angiogenesis is expected to be beneficial as per the specific disease or disorder. Such administration can be local or systemic, or a combination thereof, the optimal form of which is to be determined by the skilled practitioner. In some embodiments, the administration delivers the active ingredient of the pharmaceutical composition to one or more target sites in the subject such that the active ingredient contacts the cells (e.g., tumor cells or surrounding stromal cells) of the target site. In some embodiments, the administration is a method that delivers the active ingredient to a tumor of a subject. In some embodiments, delivery is to the exterior surrounding the cells of the tumor. In some embodiments, delivery is to the stroma surrounding the tumor. In some embodiments, the delivery is to a combination of sites involving a tumor (e.g., the tumor itself combined with the stroma surrounding the tumor, and/or potential sites of metastasis). Other useful target sites are sites of, or potential sites of metastasis in the subject. In some embodiments, the target site is the tissue stroma (e.g., surrounding a tumor or at a potential site of metastasis). In some embodiments, administration is such that the active ingredient contacts the fibroblast cells at the target site.

Local administration can be by any known method to locally and specifically deliver the composition to the desired region, such as topical (e.g., external) or intiatumoral, etc.). Systemic administration can be by a variety of methods known in the art.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor, oral and the like. The compounds of the disclosure can be administered parenterally by injection or by gradual infusion over time and can be delivered by peristaltic means.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the disclosure are formulated into conventional oral administration forms such as capsules, tablets and tonics.

For diseases or disorders that are accessible externally on the skin, such as dermal hemangiomas and skin cancer lesions (melanoma), pharmaceutical compositions described herein can be applied topically to the hemangioma or cancer lesion site in a therapeutically effective amount, in the form of topical pharmaceutical compositions. Such compositions include solutions, suspensions, lotions, gels, creams, ointments, emulsions, skin patches, etc. All of these dosage forms, along with methods for their preparation, are well known in the pharmaceutical and cosmetic art. HARRY'S COSMETICOLOGY (Chemical Publishing, 7th ed. 1982); REMINGTON'S PHARMACEUTICAL SCIENCES (Mack Publishing Co., 18th ed. 1990). Typically, such topical formulations contain the active ingredient in a concentration range of 0.1 to 100 mg/ml, in admixture with suitable vehicles. For gene therapy viruses, the dosage ranges from $10^6$ to $10^{14}$ particle per application. Other desirable ingredients for use in such preparations include preservatives, co-solvents, viscosity building agents, carriers, etc. The carrier itself or a component dissolved in the carrier can have palliative or therapeutic properties of its own, including moisturizing, cleansing, or anti-inflammatory/anti-itching properties. Penetration enhancers can, for example, be surface active agents; certain organic solvents, such as dimethylsulfoxide and other sulfoxides, dimethyl-acetamide and pyrrolidone; certain amides of heterocyclic amines, glycols (e.g., propylene glycol); propylene carbonate; oleic acid; alkyl amines and derivatives; various cationic, anionic, nonionic, and amphoteric surface active agents; and the like.

For topical administration, the pharmaceutical composition can be formulated into ointments, salves, gels, or creams, as is generally known in the art. Topical administration can utilize transdermal delivery systems well known in the art. An example is a dermal patch. Alternatively the biolistic gene gun method of delivery can be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The composition described herein can be coated on minute gold particles, and these coated particles are "shot" into biological tissues such as hemangiomas and melanoma under high pressure. An example of gene gun-based method is described for DNA based vaccination of cattle by Loehr B. I. et al., J. Virol. 2000, 74:6077-86.

In some embodiments, the compositions described herein can be administered directly by intratumoral injection. If the solid tumors and hemangiomas are accessible by injection, the pharmaceutical composition can be administered by injection directly to the tumor mass. The preferred formulation is also sterile saline or Lactated Ringer's solution. Lactated Ringer's solution is a solution that is isotonic with blood and intended for intravenous administration.

In the treatment and prevention of diabetic retinopathy and wet macular degeneration, pharmaceutical composition of the present disclosure can be applied to the eye by intra-vitral or intraocular injection. In some embodiments, the pharmaceutical composition is formulated as an eye drop solution for direct application on the eyes.

In addition to topical therapy, the pharmaceutical compositions described herein can also be administered systemically. Systemic routes include but are not limited to oral, parenteral, nasal inhalation, intratracheal, intrathecal, intracranial, and intrarectal. The pharmaceutical composition is a liquid, preferably in sterile saline, lactated Ringer's or Hank's solution. In addition, the pharmaceutical composition can be in solid forms and re-dissolved or suspended immediately prior to use. Lyophilized forms are also included.

For therapeutic applications, the pharmaceutical compositions described herein are administered to a mammal, preferably a human, in an acceptable dosage form, including those that can be administered to a human intravenously as a bolus or by continuous infusion over a period of time, by intramuscular, intraperitoneal, intracerebrospinal, subcutaneous, intra-arterial, intrasynovial, intrathecal, oral, topical, or inhalation routes. The pharmaceutical composition can be infused upstream from the site of the cells whose activity is to be modulated. Implantable drug pumps, as for example, INFUSAID® pumps (Infusaid, Inc.), are useful for delayed-release intraarterial administration. One preferred embodiment is the intramuscular injection of AAV viral vectors.

The pharmaceutical compositions described herein are also suitably administered by intratumoral, peritumoral, intralesional or perilesional routes, to exert local as well as systemic effects. The intraperitoneal route is expected to be particularly useful, for example, in the treatment of ovarian tumors. For these uses, additional conventional pharmaceutical preparations such as tablets, granules, powders, capsules, and sprays can be preferentially required. In such formulations further conventional additives such as binding-agents, wetting agents, propellants, lubricants, and stabilizers can also be required.

In some embodiments, the pharmaceutical composition described herein takes the form of a cationic liposome formulation such as those described for intratracheal gene therapy treatment of early lung cancer treatment (Zou Y. et al., Cancer Gene Ther. 2000, 7(5):683-96). The liposome formulations are especially suitable for aerosol use in lung cancer patients. The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. Vector DNA and/or virus can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757. Other non-toxic lipid based vehicle components can likewise be utilized to facilitate uptake of a vector by the cell. Other techniques in formulating expression vectors and virus as therapeutics are found in "DNA-Pharmaceuticals: Formulation and Delivery in Gene Therapy, DNA Vaccination and Immunotherapy" by Martin Schleef (Editor) December 2005, Wiley Publisher, and "Plasmids for Therapy and Vaccination" by Martin Schleef (Editor) Can 2001, are incorporated herein as reference. In some embodiments, the dosage for viral vectors is $10^6$ to $1 \times 10^{14}$ viral vector particles per application per patient.

Systemic administration can also be by transmucosal or transdermal means, or the pharmaceutical compositions can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents can be used to facilitate permeation. Transmucosal administration can be through use of nasal sprays, for example, as well as formulations suitable for administration by inhalation, or suppositories. For oral administration, the pharmaceutical compositions can take the form or conventional as well as delayed release oral administration forms such as capsules, tablets, and tonics.

The route of administration, dosage form, and the effective amount vary according to the potency of the pharmaceutical compositions, their physicochemical characteristics, and according to the treatment location. The selection of proper dosage is well within the skill of an ordinary skilled physician. Topical formulations can be administered up to four-times a day.

The pharmaceutical compositions of this disclosure are conventionally administered as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

The pharmaceutical compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

Examples of pharmaceutically acceptable carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of Psap proteins include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. Nos. 3,773,919 and 3,887,699, EP 58,481A and EP 158,277A, Canadian Patent No. 1176565, U. Sidman et al., Biopolymers 22:547 (1983) and R. Langer et al., Chem. Tech. 12:98 (1982). The active ingredients will usually be formulated in such vehicles at a concentration of about 0.1 mg/ml to 100 mg/ml and an expression vector should be in the range of $10^6$ to $1 \times 10^{14}$ viral vector particles per application per patient.

In some embodiments, other ingredients can be added to the pharmaceutical compositions as described herein, such as anti-oxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The active ingredients and/or the pharmaceutical compositions ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

The localized concentration or amount administered to a subject can be determined empirically and will depend upon the purpose of the administration, the area to be treated, the effectiveness of the composition, and the manner of administration. The localized concentration at the site of the targeted cells will desirably be in the range of about 0.05 to 50 µM, or more particularly 0.2 to 5 µM, although higher or lower dosages can be employed as appropriate. For administration to a subject such as a human, a dosage of from about 0.01, 0.1, or 1 mg/kg up to 50, 100, or 150 mg/kg or more can typically be employed.

Treatment Applications of the Peptides and Fusion Polypeptides and Nucleic Acids and Diagnostic, Prognostic, and Theranostic Methods Related to Psap Levels Other aspects of the disclosure relate to prognostic and theranostic methods. In one aspect, methods are provided for determining whether a subject having a cancer is likely to be responsive to treatment with a pharmaceutical composition described herein, e.g., in that treatment with the pharmaceutical composition will result in a desired clinical effect, such as tumor regression, delay of tumor progression, or inhibition of tumor formation, inhibition of angiogenesis, inhibition of metastasis, or inhibition of tumor recurrence.

In some embodiments, the methods described herein provide a method of theranostic evaluation in an individual diagnosed with cancer comprising making a prognostic evaluation based on the levels of Psap in the sample (e.g., a tumor sample and/or tumor stroma and/or blood) obtained from the individual, wherein a Psap level lower than 95%, 90%, 85%, 80%, 75%, 70%, 65%, 60%, 55%, or 50% of a reference Psap level indicates that the individual is likely to be responsive to treatment with a pharmaceutical composition described herein. In some embodiments, the method comprises determining the levels of Psap in the sample (e.g., a tumor sample and/or tumor stroma and/or blood) obtained from the individual and comparing the levels of Psap to a reference Psap level. In some embodiments, determining the levels of Psap comprises measuring the levels of Psap using an assay described herein. In some embodiments, the method further comprises determining that the individual is likely to be responsive to treatment with a pharmaceutical composition described herein.

In some embodiments, the methods described herein provide a method of treating an individual diagnosed with cancer comprising making a prognosis evaluation based on the levels of Psap in a sample (e.g., a tumor sample and/or tumor stroma and/or blood) obtained from the individual, and administering a therapeutically effective amount of a pharmaceutical composition described herein if the Psap level is lower than 95%, 90%, 85%, 80%, 75%, 70%, 65%, 60%, 55%, or 50% of a reference Psap level. In some embodiments, the method comprises determining the levels of Psap in the sample (e.g., a tumor sample and/or tumor stroma and/or blood) obtained from the individual and comparing the levels of Psap to a reference Psap level. In some embodiments, determining the levels of Psap comprises measuring the levels of Psap using an assay described herein.

A reference level of Psap is, for example, that obtained from a control sample of non-tumor, healthy cells in the same tissue type or organ type from which a tumor sample was excised. The reference Psap level is normalized to 100%.

In some embodiments, the reference Psap level is the average of the Psap levels obtained from a population of healthy individuals and the reference Psap level is normalized to 100%.

In some embodiments, the average Psap level from a population of healthy individuals is for a specific tissue type or organ type, e.g., the liver or lungs. For example, the average Psap level is from obtained from the liver Psap levels of a population of healthy individuals. The reference Psap level is normalized to 100%.

As used herein, the term "prognosis" is intended to encompass predictions and likelihood analyses of disease progression, particularly tumor recurrence, metastatic spread and disease relapse. The prognostic methods of the disclosure are intended to be used clinically in making decisions concerning treatment modalities, including therapeutic intervention, diagnostic criteria such as disease staging, and disease monitoring and surveillance for metastasis or recurrence of neoplastic disease.

In some embodiments, the method for prognosis evaluation is carried out on tissue samples removed from a subject in a surgical procedure, for example, in a biopsy. Preferably, the method is carried out using human cancer patient tumor samples, or samples from human patients suspected of having cancer or having abnormal growth or lesions. Various methods of harvesting a tissue sample are known to those skilled in the art and include, for example, fine needle aspiration, image-guided needle core aspiration, liposuction, laser capture microdissection, and ultrasound guided needle core aspiration, to name a few. Preferably, the samples are preserved, for example, in paraffin, and prepared for histological and immunohistochemical analysis. Alternatively, the samples can be prepared for other methods of determining and quantifying protein expression levels that are well known in the art. Tissues samples are often dissolved in TRIZOL™ reagent to prevent the breakdown and to preserve the integrity of the nucleic acids and proteins. Nucleic acid molecules can then be extracted and isolated from the TRIZOL™ dissolved sample using any of a number of procedures, which are well-known in the art. For example, the most common approach is the alcohol salt precipitation of nucleic acids.

In some embodiments, the individual is diagnosed with a benign or malignant tumor. Methods of determining whether a tumor or cancer is, metastatic or benign are well known to one skilled in the art, e.g., measurement of biomarkers such as metalloproteinase pump-1 (U.S. Pat. No. 5,726,015), CA125, or CEA.

In some embodiments, the sample obtained from the individual need not be a tumor sample. In some embodiments, the sample obtained from the individual is a biopsy tissue sample or a fluid sample such as a blood sample.

In some embodiments, the prognosis evaluation method described herein is not restricted to the analyses of Psap. Analysis of the levels of c-Myc and Tsp-1 are also contemplated. The levels of a variety of angiogenic growth factors and angiogenesis inhibitors are also contemplated as being relevant to prognosis, and methods for evaluating them are known to one skilled in the art.

In another embodiment, the treatment is administered in conjunction with chemotherapy, radiation therapy, a cytostatic agent, an anti-VEGF agent, an anti-angiogenesis factor, and/or a p53 reactivation agent.

In another aspect, prognostic methods are provided for determining whether a subject having a cancer is likely to have disease progression, particularly tumor recurrence, metastatic spread and/or disease relapse. In some embodiments, the methods described herein provide a method of making a prognostic evaluation based on the levels of Psap in a sample (e.g., a tumor sample and/or tumor stroma and/or blood) obtained from the individual, wherein a Psap level lower than a reference Psap level indicates a poor prognosis (i.e., the subject is likely to have disease progression, particularly tumor recurrence, metastatic spread and/or disease relapse). In some embodiments, the method comprises determining the levels of Psap in the sample (e.g., a tumor sample and/or tumor stroma and/or blood) obtained from the individual and comparing the levels of Psap to a reference Psap level. In some embodiments, determining the levels of Psap comprises measuring the levels of Psap using an assay described herein. In some embodiments, the method further comprises identifying or diagnosing a subject as having a poor prognosis (i.e., the subject is likely to have disease progression, particularly tumor recurrence, metastatic spread and/or disease relapse) based on the levels of Psap.

In some embodiments, the method for diagnosing metastasis an individual diagnosed with cancer comprises determining the level of Psap expression in a sample obtained from an individual diagnosed with cancer, wherein when the level of Psap in the sample is the same or lower than a reference Psap level, there is an increased likelihood of cancer metastasis and/or recurrence of neoplastic disease, and thus a poor prognosis. The sample can be blood, preferably platelet, serum or plasma. Methods of collecting and isolating platelets, serum or plasma are well known in the art. The reference Psap level is the average Psap level in the corresponding platelets, serum or plasma of normal healthy individuals not diagnosed with any cancer. The reference Psap levels are normalized to 100%. The Psap levels in the platelets, serum or plasma of patients having non-metastatic cancer are higher than the reference Psap levels, e.g., at least 5% higher. On the other hand, the Psap levels in platelets, serum or plasma of patients having metastatic cancer tend to be comparable, and can even be lower than the reference Psap levels. Hence, when a sample obtained from an individual recently diagnosed with cancer has a slightly lower Psap level in the plasma compared to the reference Psap level, there is an increased likelihood that individual's cancer has already metastasized.

In some embodiments, the method for prognostic evaluation of an individual diagnosed with cancer comprises determining the level of Psap expression in a sample (e.g., a tumor sample and/or tumor stroma and/or blood) obtained from the individual diagnosed with cancer, wherein when the level of Psap in the tumor sample is lower than a reference Psap level, there is an increased likelihood of cancer metastasis and/or recurrence of neoplastic disease, and thus a poor prognosis.

In some embodiments, the method for prognostic evaluation in an individual diagnosed with cancer comprises: (a) determining the level of Psap expression in a sample obtained from an individual diagnosed with cancer at a first time point; (b) determining the level of Psap expression in a sample obtained from an individual diagnosed with cancer at a second time point, the first time point being before the second time point; and (c) comparing the levels of Psap from the time points with a reference Psap level; wherein when the level of Psap at the second time point becomes lower than the reference Psap level, the cancer has likely metastasized.

In some embodiments, the sample is blood, platelets, serum or plasma.

In some embodiments, the method described herein makes a prediction on the likelihood of cancer metastasis, recurrence, and relapse of neoplastic disease in a subject diagnosed with cancer by comparing the level of Psap in the tumor to a reference level of Psap. A reference level of Psap can be that obtained from a control sample of non-tumor, healthy cells in the same tissue type or organ type from which a tumor sample was excised. The reference Psap level is normalized to 100%. A lower level of Psap determined in a sample compared to a reference Psap level is about 95% to 0% of the reference Psap level, including all percentages between 95% and 0%, i.e., about 95%, 90%, 80%, 70%, 60%, 50%, 40%, 30%, 20%, 10%, 5%, 2%, 1%, 0.5% to 0% of the reference Psap level. For example, if the prognosis is for breast cancer in a female subject, the reference Psap level is determined using healthy breast tissue from a female subject. This reference breast Psap level is compared with a level of Psap determined in a breast cancer tissue sample. If the breast cancer tissue sample has a Psap level of 65% of a reference Psap level found in a healthy breast tissue sample, the prognosis is an increased likelihood of cancer metastasis and/or recurrence of neoplastic disease, and thus a poor prognosis.

In some embodiments, the method for prognostic evaluation of an individual diagnosed with cancer further comprises: (a) determining the level of Psap expression in the tumor stroma; and (b) determining the level of Tsp-1 expression in the tumor stroma, wherein when the levels of Psap and Tsp-1 in the tumor stroma are lower than a reference Psap level and a reference Tsp-1 level respectively, there is an increased likelihood of cancer metastasis and/or recurrence of neoplastic disease, and thus a poor prognosis. The method described herein makes a prediction on the likelihood of cancer metastasis, recurrence, and relapse of neoplastic disease in a subject diagnosed with cancer by comparing the levels of Psap and Tsp-1 in the tumor stroma with reference levels of Psap and Tsp-1. Reference levels of Psap and Tsp-1 are those obtained from a control sample of non-tumor, healthy cells in the same tissue type or organ type from which a tumor sample was excised. The reference Psap and Tsp-1 levels are normalized to 100%. Lower levels of Psap and Tsp-1 in a sample compared to the reference Psap and Tsp-1 levels are about 95% to 0% of the reference Psap level, including all percentages between 95% and 0%, i.e., about 95%, 90%, 80%, 70%, 65%, 60%, 55%, 50%, 45%, 40%, 35%, 30%, 25%, 20%, 15%, 10%, 9%, 8%, 7%, 6%, 5%, 4%, 3%, 2%, 1%, 0.5%, or 0% of the reference Psap or Tsp-1 levels. For example, if the prognosis is for lung cancer in a male subject, the reference Psap and Tsp-1 levels are determined using healthy lung tissue from a male subject. These reference lung Psap and Tsp-1 levels are then compared with levels of Psap and Tsp-1 determined in a lung cancer tissue sample. If the lung cancer tissue sample has a Psap level of 25% and a Tsp-1 level of 5% compared to the respective reference Psap and Tsp-1 levels found in healthy lung tissue, the prognosis is an increased likelihood of cancer metastasis and/or recurrence of neoplastic disease, and thus a poor prognosis. Since highly metastatic tumors have virtually no detectable Tsp-1 and Psap, extremely low levels (i.e., about 30%-0% of the reference levels) or undetectable amounts of Psap and Tsp-1 in the cancer tissue sample strongly indicate definite cancer metastasis and/or recurrence of neoplastic disease, and thus a poor prognosis, and would require an aggressive treatment plan. On the basis of the prognosis and the levels of Tsp-1 and Psap in a cancer tissue sample, a clinician skilled in the art can design a customized treatment plan for an afflicted individual. The treatment plan can include administering the pharmaceutical composition described herein in conjunction with surgical removal of tumors or tissue with cancerous lesions, chemotherapy, radiation therapy, a cytostatic agent, an anti-VEGF agent, an anti-angiogenesis factor and/or a p53 reactivation agent. Administration of an effective amount of the pharmaceutical composition systemically raises the level of Psap and consequently the Tsp-1 and p53 in the cancer cells, surrounding tissue, and potential metastatic sites to which a metastatic cancer cell can target. This can prevent future metastasis and also establishment of secondary tumors. Administration is by one or more methods known in the art, determined by the skilled practitioner, e.g. injected intratumorly.

In another embodiment, the method for monitoring or surveillance for the development of metastasis in an individual diagnosed with cancer comprises determining the level of Psap expression in a sample obtained from an individual at a first time point, determining the level of Psap expression in a sample obtained from the individual at a second time point, the first time point being before the second time point; comparing the levels of Psap from the time points with a reference Psap level, wherein when the levels of Psap at the second time point are lower than the reference Psap level, e.g., 95% or less, the cancer is deemed likely to have developed into a metastatic cancer and thus evidences a poor prognosis. The sample can be blood, preferably platelets, serum or plasma. The reference Psap level is the average Psap level in the corresponding platelets, serum or plasma of normal healthy individuals not diagnosed with any cancer. The reference Psap levels are normalized to 100%. The Psap levels in the platelets, serum or plasma of patients diagnosed having non-metastatic cancer is higher than the reference Psap levels, at least 5% higher. On the other hand, the Psap levels in platelet, serum or plasma of patients having metastatic cancer can be the same, and/or lower than the reference Psap levels. The Psap level in the sample can be used as a biomarker for the progression of the disease into the metastatic form. For example, in a patient who has been newly diagnosed with breast cancer. A single tumor mass was found and excised. There was no indication that the tumor had metastasized. A sample of her plasma is collected at this initial diagnosis and the Psap level in her plasma is determined and compared to the reference Psap level. Over the next few years, periodic sampling of her plasma Psap level can be performed, e.g., every three months initially for the first two years, then every six months for the next five years thereafter if she remains cancer free in the first two years. These samplings of plasma Psap level can be compared to the reference Psap level and charted over time. When there is a drop in her plasma Psap level compared to the reference Psap level, at least 5%, this is an indication that possibly the cancer has recurred and is of the metastatic form. Her physician can then perform a thorough screening for the cancer recurrence. The method described herein provides a method of prognosis evaluation in an individual diagnosed with cancer.

Some aspects of this disclosure provide methods for determining or identifying whether a subject having a cancer is responsive to treatment with a therapeutic molecule other than a Psap polypeptide ("non-Psap treatment"), e.g., in that treatment with non-Psap treatment will result in a desired clinical effect, such as tumor regression, delay of tumor progression, or inhibition of tumor formation or tumor recurrence. Therapeutic molecules are described herein. The term "responsive to treatment with a non-Psap treatment" as used herein, accordingly, refers to a subject in which administration of the non-Psap treatment will have a desired effect. For example, a subject having a cancer and identified to be responsive to treatment with a non-Psap treatment, e.g., by a diagnostic method provided herein, is a subject that benefits clinically from administration of the non-Psap treatment. For example, the subject may benefit from administration of a non-Psap treatment in that administration of an effective amount of the non-Psap treatment may result in one or more of a reversal, an inhibition, or a delay in tumor development, tumor formation, tumor growth, tumor vascularization, tumor angiogenesis tumor survival, tumor progression, tumor recurrence, or metastasis.

In some aspects, the disclosure provides methods for evaluating whether a subject is responsive to treatment with a non-Psap treatment. In some embodiments, the method comprises determining a level of Psap in a sample obtained from the subject, and comparing the level of Psap determined in a sample obtained from the subject to a reference level. In some embodiments, if the level determined in a sample obtained from the subject is higher than the reference level, the subject is identified as responsive to a non-Psap treatment. In some embodiments, if the level determined in a sample obtained from the subject is the same as or lower than the reference level, the subject is identified as not responsive to a non-Psap treatment.

Some aspects of this disclosure provide in vitro methods for evaluating responsiveness of a subject to treatment with a non-Psap treatment. In some embodiments, the method comprises determining a level of Psap in a sample obtained from the subject; and comparing the level of Psap determined in the sample to a reference level, wherein if the level determined in the sample is higher than the reference level, the subject is identified as responsive to treatment with the non-Psap treatment; or if the level determined in the sample is the same or lower than the reference level, the subject is identified as not responsive to the non-Psap treatment.

In some embodiments the reference level is a level of Psap determined in sample (e.g., tissue or blood) obtained from the subject at a different time point. In some embodiments the reference level is a level of Psap in a sample (e.g., tissue or blood) from a healthy subject. In some embodiments the reference level is a level of Psap expected or observed in a sample obtained from a healthy subject, or an aggregate or average level of Psap expected or observed in samples from a population of healthy subjects. A healthy subject is a subject who has no signs or symptoms of disease and/or a subject when examined by a medical professional is identified as not having evidence of disease.

In some embodiments, the level of Psap is determined in a sample obtained from the subject comprising or suspected to comprise malignant cells, e.g., tumor cells. In some embodiments, the sample is a tissue sample or body fluid sample. In some embodiments, the tissue sample comprises tumor tissue or tumor cells. In some embodiments, the body fluid is blood, plasma, serum, lymph, sputum, cerebrospinal fluid, or urine.

Plasma, Serum, and Platelet Sampling

The patient's blood can be drawn directly into anticoagulants containing citrate, EDTA, PGE, and theophylline. The whole blood should be separated into the plasma portion, the cells, and platelets portion by refrigerated centrifugation at 3500 g, 2 minutes. Since platelets have a tendency to adhere to glass, it is preferred that the collection tube be siliconized. After centrifugation, the supernatant is the plasma. The plasma is filtered through a 0.2 µm filter to remove residual platelets and is kept at −20° C. before measurements are performed.

Alternately, the serum can be collected from the whole blood. Collect the blood in a hard plastic or glass tube; blood will not clot in soft plastic. Draw 15 mL of whole blood for 6 mL of serum. The whole blood is allowed to stand at room temperature for 30 minutes to 2 hours until a clot has formed. Carefully separate clot from the sides of the container using a glass rod or wooden applicator stick and leave overnight at 4° C. After which, decant serum, centrifuge, and/or using a Pasteur pipette, remove serum into a clean tube. Clarify the serum by centrifugation at 2000-3000 rpm for 10 minutes. The serum is stored at −20° or −80° C. measurement is performed. Detailed described of obtaining serum using collection tubes can be found in U.S. Pat. No. 3,837,376 and is incorporated by reference. Blood collection tubes can also be purchased from BD Diagnostic Systems, Greiner Bio-One, and Kendall Company.

Platelets can be separated from whole blood. When whole blood is centrifuged as described herein to separate the blood cells from the plasma, a pellet is formed at the end of the centrifugation, with the plasma above it. Centrifugation separates out the blood components (red blood cells, white blood cells, and platelets) by their various densities. The red blood cells (RBCs) are denser and will be the first to move to the bottom of the collection/centrifugation tube, followed by the smaller white blood cells, and finally the platelets. The plasma fraction is the least dense and is found on top of the pellet. The "buffy coat" which contains the majority of platelets will be sandwiched between the plasma and above the RBCs. Centrifugation of whole blood (with anti-coagulant, PGE and theophylline) can produce an isolated a platelet rich "buffy coat" that lies just above the buoy. The "buffy" coat contains the concentrated platelets and white blood cells.

Platelets can be separated from blood according to methods described in U.S. Pat. No. 4,656,035 using lectin to agglutinate the platelets in whole blood. Alternatively, the methods and apparatus described in U.S. Pat. No. 7,223,346 can be used involving a platelet collection device comprising a centrifugal spin-separator container with a cavity having a longitudinal inner surface in order to collect the "buffy coat" enriched with platelets after centrifugation. As another alternative, the methods and apparatus as described in WO/2001/066172 can be used. Each of these is incorporated by reference herein in their entirety.

Platelets can be isolated by the two methods described in A. L. Copley and R. B. Houlihan, Blood, 1947, 2:170-181, which is incorporated by reference herein in its entirety. Both methods are based on the principle that the platelet layer can be obtained by repeated fractional centrifugation.

The whole blood can be first separated into platelet-rich plasma and cells (white and red blood cells). Platelet rich plasma (PRP) can be isolated from the blood centrifugation of citrated whole blood at 200×G for 20 minutes. The platelet rich plasma is then transferred to a fresh polyethylene tube. This PRP is then centrifuged at 800×G to pellet the platelets and the supernatant (platelet poor plasma [PPP]) can be saved for analysis by ELIZA at a later stage. Platelets can be then gently re-suspended in a buffer such as Tyrodes buffer containing 1 U/ml PGE2 and pelleted by centrifugation again. The wash can be repeated twice in this manner before removing the membrane fraction of platelets by centrifugation with Triton X, and lysing the pellet of platelet for Psap analyses. Platelets can be lysed using 50 mM Tris HCL, 100-120 mM NaCl, 5 mM EDTA, 1% Igepal and Protease Inhibitor Tablet (complete TM mixture, Boehringer Manheim, Indianapolis, Ind.). For the analysis of Psap mRNA, the pellet of platelets can be dissolved in TRIZOL® immediately after separation from the plasma.

Determining Expression Level by Measuring mRNA

Real time PCR is an amplification technique that can be used to determine levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA is extracted from a biological sample, e.g., a tumor and normal tissue, and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes can be obtained commercially from, for example, Perkin Elmer/Applied Biosystems (Foster City, Calif.). To quantitate the amount of the specific nucleic acid of interest in a sample, a standard curve is generated using a control. Standard curves can be generated using the Ct values determined in the real-time PCR, which are related to the initial concentration of the nucleic acid of interest used in the assay. Standard dilutions ranging from $10^1$-$10^6$ copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan probes are well known in the art. Detailed protocols for real-time quantitative PCR can be found in, e.g., for RNA in Gibson et al., 1996, Genome Res., 10:995-1001 and for DNA in Heid et al., 1996, Genome Res., 10:986-994.

The TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, www2.perkin-elmer.com).

In another embodiment, detection of RNA transcripts can be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

Detection of RNA transcripts can further be accomplished using known amplification methods. For example, it is within the scope of the present disclosure to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap lipase chain reaction (RT-AGLCR) as described by R. L. Marshall, et al., PCR Methods and Applications 4: 80-84 (1994). One suitable method for detecting enzyme mRNA transcripts is described in reference Pabic et al., Hepatology, 37(5): 1056-1066, 2003, which is herein incorporated by reference in its entirety.

Other known amplification methods which can be utilized herein include but are not limited to the so-called "NASBA" or "3 SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

In situ hybridization visualization can also be employed, wherein a radioactively labeled antisense RNA probe is hybridized with a thin section of a biopsy sample, washed, cleaved with RNase and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used.

Alternatively, mRNA expression can be detected on a DNA array, chip or a microarray. Oligonucleotides corresponding to enzyme are immobilized on a chip Which is then hybridized with labeled nucleic acids of a test sample obtained from a patient. Positive hybridization signal is obtained with the sample containing enzyme transcripts. Methods of preparing DNA arrays and their use are well known in the art. (See, for example U.S. Pat. Nos. 6,618, 6796; 6,379,897; 6,664,377; 6,451,536; 548,257; U.S. Patent Application No. 20030157485 and Schena et al., 1995 Science 20:467-470; Gerhold et al., 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the tissue sample to be tested, reverse transcribed, and fluorescent-labeled cDNA probes are generated. The microarrays capable of hybridizing to enzyme cDNA are then probed with the labeled cDNA probes, the slides scanned and fluorescence intensity measured. This intensity correlates with the hybridization intensity and expression levels.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided, for example, in Innis et al., (1990) PCR Protocols, A Guide to Methods and Applications, Academic Press, Inc. N.Y.

Determining Expression Level by Measuring Protein

The levels of Psap and Tsp-1 proteins can be measured by contacting the tissue sample with an antibody-based binding moiety that specifically binds to Psap or Tsp-1, or to a fragment of Psap or Tsp-1. Formation of the antibody-protein complex is then detected by a variety of methods known in the art.

The term "antibody-based binding moiety" or "antibody" when used herein in reference to a member of the antibody-antigen specific binding pair, includes immunoglobulin molecules and immunologically active determinants of immunoglobulin molecules, e.g., molecules that contain an antigen binding site which specifically binds (immunoreacts with) to the Psap proteins. The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-based binding moiety" includes polyclonal, monoclonal, or other purified preparations of antibodies and recombinant antibodies. The term "antibody-based binding moiety" is further intended to include humanized antibodies, bispecific antibodies, and chimeric molecules having at least one antigen binding determinant derived from an antibody molecule. In a preferred embodiment, the antibody-based binding moiety detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of Psap or Tsp-1 present in the tissue samples correlate to the intensity of the signal emitted from the detectably labeled antibody.

In one preferred embodiment, the antibody-based binding moiety is detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies of the present disclosure include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audioradiography. Isotopes which are particularly useful for the purpose of the present disclosure are 3H, 1311, 35S, $^{14}$C, and preferably $^{125}$I.

It is also possible to label an antibody with a fluorescent compound. When the fluorescently labeled antibody is exposed to light of the proper wavelength, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as 152Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, levels of enzyme protein can be detected by immunoassays, such as enzyme linked immunoabsorbant assay (ELISA), radioimmunoassay (RIA), Immunoradiometric assay (IRMA), Western blotting, immunocytochemistry or immunohistochemistry, each of which are described in more detail below. Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329,209 and 6,365,418, which are herein incorporated by reference in their entirety.

Immunoassays

The most common enzyme immunoassay is the "Enzyme-Linked Immunosorbent Assay (ELISA)." ELISA is a technique for detecting and measuring the concentration of an antigen using a labeled (e.g., enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g., anti-enzyme) is linked to a solid phase (i.e., a microtiter plate) and exposed to a biological sample containing antigen (e.g., enzyme). The solid phase is then washed to remove unbound antigen. A labeled antibody (e.g., enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e., enzyme). The antigen-antibody mixture is then contacted with a solid phase (e.g., a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, most preferably by light microscopy of a sample stained with a stain that is detected in the visible spectrum, using any of a variety of such staining methods and reagents known to those skilled in the art.

Alternatively, "Radioimmunoassays" can be employed. A radioimmunoassay is a technique for detecting and measuring the concentration of an antigen using a labeled (e.g., radioactively or fluorescently labeled) form of the antigen. Examples of radioactive labels for antigens include 3H, 14C, and 125I. The concentration of antigen enzyme in a biological sample is measured by having the antigen in the biological sample compete with the labeled (e.g., radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed S. aureus. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric assay" (IRMA) is an immunoassay in which the antibody reagent is radioactively labeled. An IRMA requires the production of a multivalent antigen conjugate; by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

Other techniques can be used to detect Psap and Tsp-1 in the tissue samples obtained in a biopsy, according to a practitioner's preference, and based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Detectably labeled anti-enzyme antibodies can then be used to assess enzyme levels, where the intensity of the signal from the detectable label corresponds to the amount of enzyme present. Levels can be quantified, for example by densitometry.

In some embodiments, Psap and Tsp-1, and/or their mRNA levels in the tissue sample can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, and 20030077616, which are herein incorporated by reference.

Mass spectrometry methods are well known in the art and have been used to quantify and/or identify biomolecules, such as proteins (see, e.g., Li et al., (2000) Tibtech 18:151-160; Rowley et al., (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. Nos. 5,118,937 and 5,045,694.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of Psap or Tsp-1 mRNA or protein will typically depend on the detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Antibodies or Antisera Against Psap and Tsp-1 Proteins

Antibodies or anti-sera can be used to determine the expression levels of Psap and Tsp-1. The antibodies for use in the present disclosure can be obtained from a commercial source such as Novus Biologicals (anti-prosaposin, Clone 1D1-C12, catalog # H00005660-M01), Santa Cruz Biotechnology (Anti-saposin B (E-15), catalog # sc-27014; anti-Tsp-1, Clone CSI 002-65, catalog # sc-59888), and Labvision (anti-Tsp-1, clone Ab-2, catalog # MS-419-B). The antibodies can be polyclonal or monoclonal antibodies. Alternatively, antibodies can be raised against Psap protein (Genbank Accession No. NM_002778) or Tsp-1 (Genbank Accession No. NM_003246). Methods for the production of enzyme antibodies are disclosed in PCT publication WO 97/40072 or U.S. Application. No. 2002/0182702, which are herein incorporated by reference.

Antibodies for use in the present disclosure can be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702,892 and WO 01/18058 disclose bacteriophage display libraries and selection methods for producing antibody binding domain fragments.

Detection of Psap and Tsp-1 antibodies can be achieved by direct labeling of the antibodies themselves, with labels including a radioactive label such as $^{3}H$, $^{14}C$, $^{35}S$, $^{125}I$, or $^{131}I$, a fluorescent label, a hapten label such as biotin, or an enzyme such as horse radish peroxidase or alkaline phosphatase. Alternatively, unlabeled primary antibody is used in conjunction with labeled secondary antibody, comprising antisera, polyclonal antisera or a monoclonal antibody specific for the primary antibody. In some embodiments, the primary antibody or antisera is unlabeled, the secondary antisera or antibody is conjugated with biotin and enzyme-linked strepavidin is used to produce visible staining for histochemical analysis.

Unless otherwise stated, the present disclosure was performed using standard procedures that are well known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al., ed., John Wiley and Sons, Inc.); Current Protocols in Protein Science (CPPS) (John E. Coligan, et al., ed., John Wiley and Sons, Inc.); Current Protocols in Cell Biology (CPCB) (Juan S. Bonifacino et al., ed., John Wiley and Sons, Inc.); Culture of Animal Cells: A Manual of Basic Technique by R. Ian Freshney, Publisher: Wiley-Liss; 5th edition (2005); and Animal Cell Culture Methods (Methods in Cell Biology, Vol 57, Jennie P. Mather and David Barnes editors, Academic Press, 1st edition, 1998), which are all incorporated herein by reference in their entireties.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Definitions of common terms in molecular biology are found in Benjamin Lewin, Genes IX, published by Jones & Bartlett Publishing, 2007 (ISBN-13: 9780763740634); Kendrew et al., (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

It should be understood that this disclosure is not limited to the particular methodology, protocols, and reagents, etc., described herein and as such may vary. The terminology used herein is for the purpose of describing particular embodiments only, and is not intended to limit the scope of the present disclosure, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

This disclosure is further illustrated by the following examples which should not be construed as limiting. The contents of all references cited throughout this application, as well as the figures and tables are incorporated herein by reference in their entirety.

EXAMPLES

Example 1: Identification of Saposin a Derived Polypeptides with Saposin a Activity Experimental Procedures
Creation of Prosaposin Truncation Mutants All prosaposin coding fragments were created by PCR amplification using the common 5' primer: 5'-ggcggcgtcga-cATGTACGCCCTCTTCCTCC-3' (SEQ ID NO: 30). The saposin A region was created using the 3' primer: ggcgcctctagaAGAGACTCGCAGAGGTTGAG (SEQ ID NO: 31). The saposin AB region was created using the 3' primer: ggcgcctctagaACCTCATCACAGAACCC (SEQ ID NO: 32). The saposin ABC region was created using the 3' primer: ggcgcctctagaGCCAGAGCAGAGGTGCAGC (SEQ ID NO: 33). The PCR products were digested with Sal1 and Xba1 and cloned into pDNR-Dual (Clontech). The saposin regions were then cloned into pLP-CMVNeo using the Creator cloning system (Clontech). Prosaposin truncation constructs were used to transiently transfect PC3M-LN4 cells.

Saposin a Peptide Scanning

Seven overlapping 20(21)-amino acid peptides spanning the length of saposin A were synthesized (Anaspec, Fremont, Calif.). The sequences were: 1-20-SLPCDICKDV-VTAAGDMLKD (SEQ ID NO: 34), 11-30-VTAAGDM-LKDNATEEEILVY (SEQ ID NO: 35), 21-40-NATEEEILVYLEKTCDWLPK (SEQ ID NO: 36), 31-50-LEKTCDWLPKPNMSASCKEI (SEQ ID NO: 37), 41-60-PNMSASCKEIVDSYLPVILD (SEQ ID NO: 38), 51-70-VDSYLPVILDIIKGEMSRPG (SEQ ID NO: 39), 61-81-IIKGEMSRPGEVCSALNLCES (SEQ ID NO: 40). Five subsequently tested peptides consisted of residues 35-47: CDWLPKPNMSASC (SEQ ID NO: 41), 35-40: CDWLPK (SEQ ID NO: 3), 38-43: LPKPNM (SEQ ID NO: 42), 42-47: NMSASC (SEQ ID NO: 43), 35-39: CDWLP (SEQ ID NO: 29), 35-38: CDWL (SEQ ID NO: 44)., 35-37: CDW, 36-39: DWLPK (SEQ ID NO: 4), 37-39: DWLP (SEQ ID NO: 5), 37-40: WLPK (SEQ ID NO: 45), 38-40: LPK. Pegylated 35-40 amino acid peptides were also tested as were peptides with a d-amino acid substituted at positions 36 and 38 in a peptide corresponding to residues 36-39 and at positions 37 and 39 in the same peptide.

These peptides were used to treat prostate and lung fibroblasts in vitro at a concentration of 10 ug/mL for 16 hours in ATCC-specified media supplemented with 0.1% FBS. Tsp-1 and p53 expression was analyzed by western blot as described previously (Kang, Y., et al., (2003) Cancer Cell 3:537-549.)

Peptide Analysis In Vivo

For tumor-free analysis C57B16 mice were treated with 200 uL of PC3M-LN4 media alone or in combination with peptides described above at dose of 30 mg/kg/day for 5 days. After treatment the animals were sacrificed and the lungs were harvested, lysed and analyzed for Tsp-1 and p53 protein levels as described previously (Kang et al).

Tumor Treatment
Prostate Tumors

C57B16 SCID mice were injected with $1 \times 10^6$ PC3M-LN4 prostate cancer cells in the prostate gland as described previously (Kang et al). After 26 days the animals were treated with either PBS or peptides corresponding to residues 36-40 or 36-39 of saposin A at a dose of 30 mg/kg/day via intraperitoneal (i.p.) injection. After 16 days of treatment all animals were sacrificed, prostate tumors were weighed and harvested, along with the lungs of animals. Tissues were either fixed in NBF, or lysed and analyzed for Tsp-1 and p53 expression by western blot analysis.

Melanomas

C57B16 mice were injected with $0.5 \times 10^6$ B16-B6 melanoma cells subcutaneously. After 10 days the animals were treated with either PBS or a peptide corresponding to residues 36-39 of saposin A at a dose of 30 mg/kg/day via i.p. injection. After 16 days of treatment all animals were sacrificed, prostate tumors were weighed and harvested, along with the lungs of animals. Tissues were either fixed in NBF, or lysed and analyzed for Tsp-1 and p53 expression by western blot analysis.

Lung Metastasis

C57B16 mice were injected with $1 \times 10^6$ Lewis Lung Carcinoma cells via tail vein. After 10 days the animals were treated with either PBS or a peptide corresponding to residues 36-40 of saposin A at a dose of 30 mg/kg/day via i.p. injection. After 16 days of treatment all animals were sacrificed, lungs were weighed and harvested. Tissues were either fixed in NBF, or lysed and analyzed for Tsp-1 and p53 expression by western blot analysis.

Results

It was sought to determine whether there was a smaller domain within saposin A that contained the p53/Tsp-1 stimulating activity. Thus, the activity of a 13-amino acid cyclized peptide spanning residues 35-47 was tested and it was observed that it was also able to stimulate the expression of p53 and Tsp-1 in prostate fibroblasts. C57B16 mice (5-6 wks old) were injected daily with 300 uL of serum free DMEM, conditioned media (CM) from non-metastatic PC3 cells, CM from metastatic PC3M-LN4 cells and PC3M-LN4

CM plus 30 mg/kg of the pegylated 6 amino acid polypeptide (PEG2000-CDWLPK (SEQ ID NO: 46)) or 30 mg/kg of the pegylated 18 amino acid polypeptide (PEG2000-EKTCDWLPKPNMSASCKE (SEQ ID NO: 47)). After 9 days the mice were euthanized and the lungs and livers harvested and either fixed in formalin or lysed for Western blot analysis. Western blot analysis, shown in FIG. 1, revealed that both the pegylated 6- and 18-amino acid polypeptides were as, or more, effective than PC3 conditioned media at stimulating the expression of Tsp-1 in the lung and liver of the mice.

Figure 2:
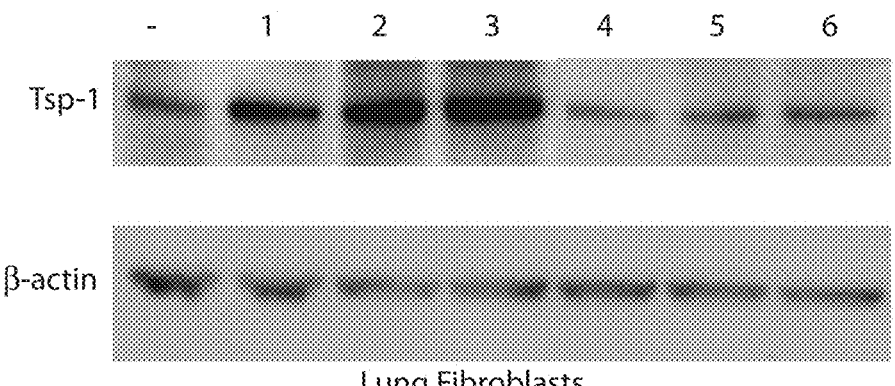
FIG. 2 provides photographs of experimental results that indicate the 5- and 4-amino acid peptides shown therein exhibit activity in vitro.

Three overlapping 6-amino acid peptides from the 13-amino acid region were then tested. Finally, peptides of various lengths within the 35-40 region were tested. It was observed that removing the cysteine at residue 35 actually increased the ability of the resulting 5-amino acid peptide to stimulate Tsp-1 in prostate fibroblasts (FIG. 2). It was also observed that removing the lysine at the last position did not affect the activity of the peptide to stimulate Tsp-1 (FIG. 2). Finally, the activity of the 4-amino acid peptide (DWLP (SEQ ID NO: 5)) and the 5-amino acid peptide (DWLPK (SEQ ID NO: 4)) to stimulate Tsp-1 and p53 in the lungs of mice treated with CM from PC3M-LN4 was tested to simulate a systemic tumor environment.

Figure 3:
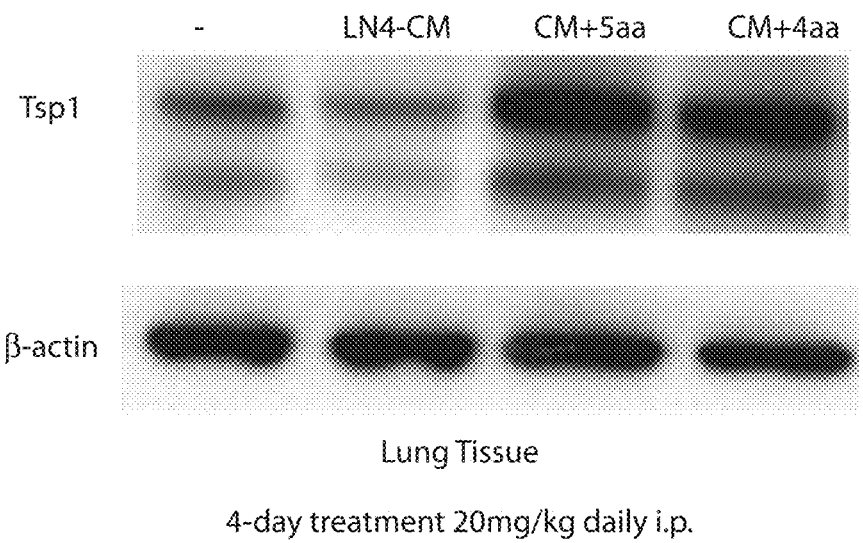
FIG. 3 provides photographs of experimental results that indicate the 5- and 4-amino acid peptides shown therein exhibit Tsp-1 stimulatory Psap activity in vivo.
Figure 4:
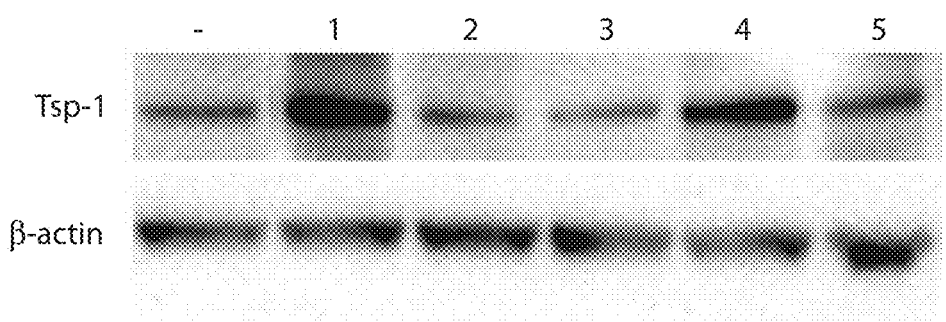
FIG. 4 provides photographs of experimental results that indicate through alanine substitution analysis that only the Leucine residue is not required for activity of the indicated peptides.

Having determined that the 4- and 5-amino acid peptides retain the activity of the full-length prosaposin protein it was sought to determine whether they also had activity in vivo. As such, mice with CM from PC3M-LN4 cells were treated alone or in combination with the 4- and 5-amino acid peptides. Western blot analysis revealed that treatment of mice with both peptides not only abrogated the ability of PC3M-LN4 media to repress Tsp-1 but stimulated Tsp-1 and p53 expression in the lungs of these mice 6-fold above basal levels (FIG. 3). Each of the 4 amino acids were then substituted with alanine and it was observed that all substitutions except the leucine at residue 3 rendered the peptide inactive at stimulating Tsp-1 in lung fibroblasts in vitro (FIG. 4). Conservative amino acid substitutions were then made and it was observed that substituting the tryptophan at residue 2 with tyrosine, or the leucine at position 3 with valine, slightly increased the activity of the peptide at stimulating Tsp-1 expression in lung fibroblasts in vitro (FIG. 5). These results indicate that substituting tyrosine for tryptophan or valine for leucine slightly improve activity.

The peptides were then tested for their ability to inhibit tumor growth and metastasis in three models, the PC3M-LN4 prostate cancer model, the B16-B6 melanoma model and the Lewis Lung Carcinoma (LLC) model. $1\times10^6$ PC3M-LN4 cells were first injected into the prostate gland of SCID mice. After 26 days these mice were treated with either PBS alone or the 4- or 5-amino acid peptide at a dose of 30 mg/kg/day via i.p. injection. The mice were treated for 16 days after which the mice were examined the size of the tumors and the expression of Tsp-1 and p53 in the primary tumors and lungs of the animals. The tumors in animals treated with the 4- and 5-amino acid peptides were, on average, 45% and 40% the size of control animals, respectively (FIG. 6).

Figure 7:
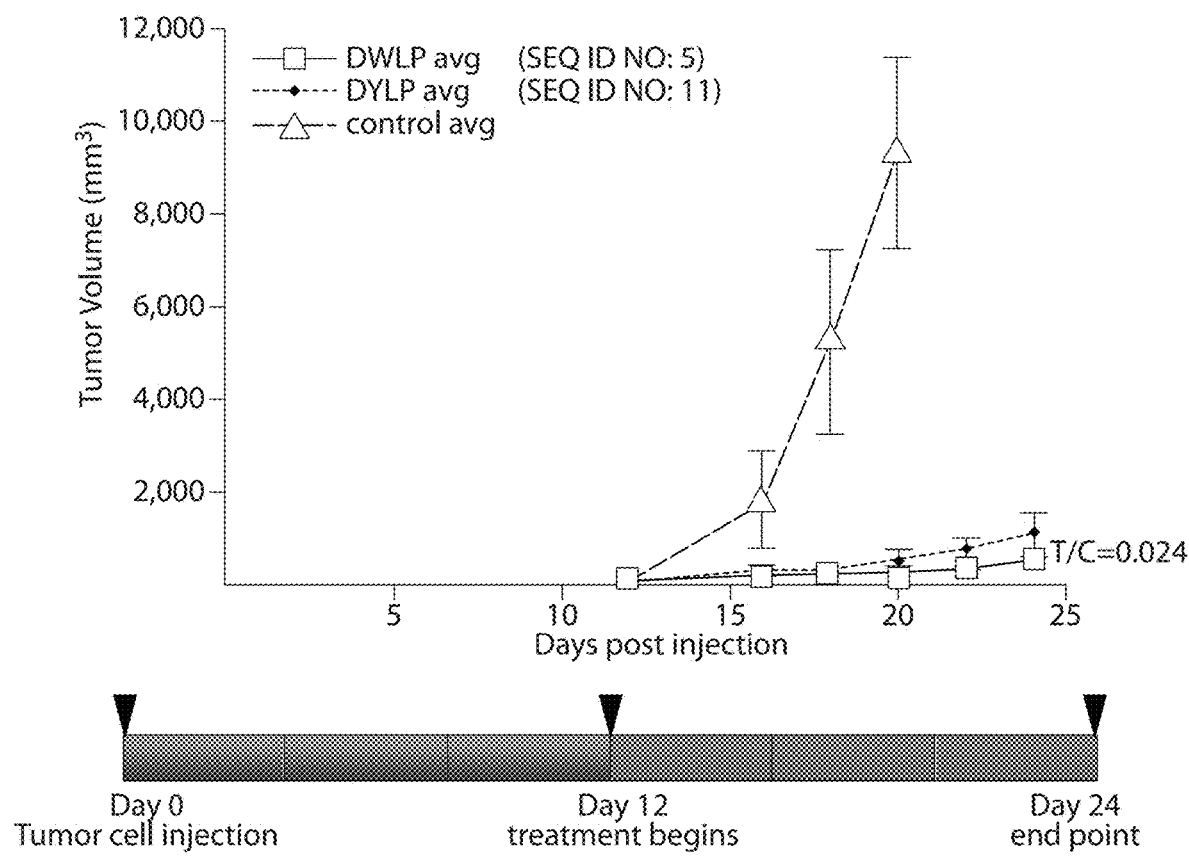
FIG. 7 is a line graph of experimental results that indicate the Psap fragments tested significantly inhibit melanoma growth.

C57B16 mice were injected with the $0.5\times10^6$ cells of the syngeneic melanoma cell line B16-B6. After 10 days the mice were treated with either PBS or the 4-amino acid peptide at a dose of 45 mg/kg/day. Mice were treated for 14 days after which the animals were sacrificed and the primary tumors and lungs analyzed for Tsp-1 and p53 expression. The tumors in the treated group were 2.4% the size of the tumors in the control, PBS treated, animals (FIG. 7).

Figure 8:
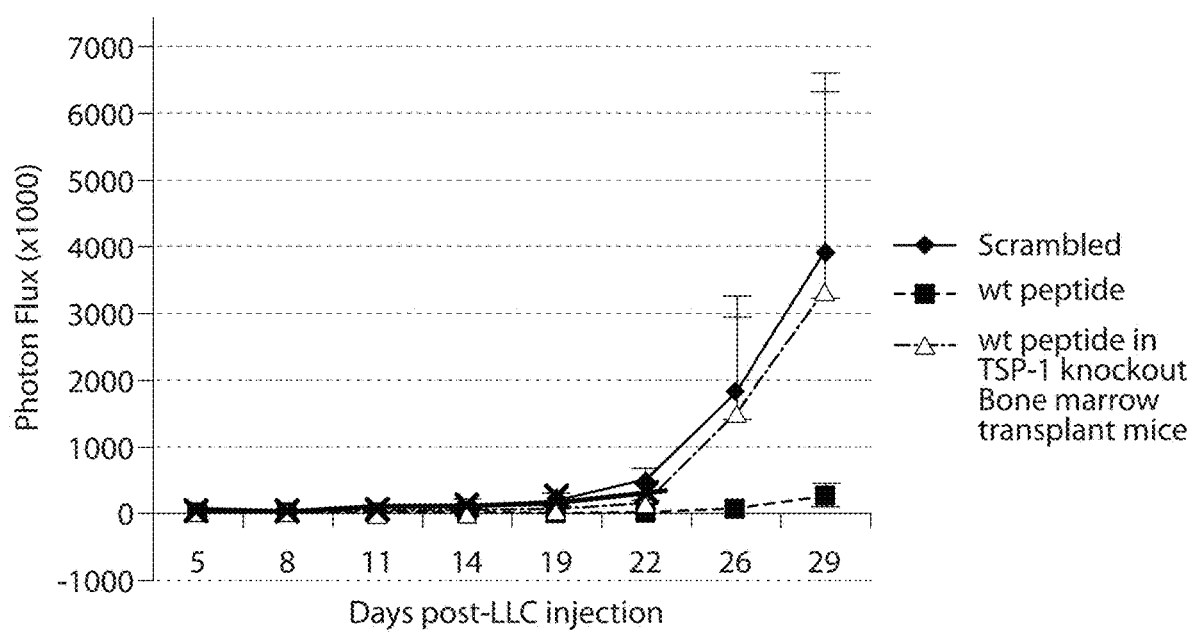
FIG. 8 is a line graph of experimental results that indicate the Psap fragment tested significantly inhibits metastasis.

$1\times10^6$ luciferase-expressing LLC cells were then injected via tail vein into C57B16 mice. After 5 days the mice were treated with the 5-amino acid peptide at a dose of 30 mg/kg/day via i.p. injection. After 29 days the animals were sacrificed, at which point the average luciferase activity in the peptide treated mice, as measured by a Xeongoen IVIS system, was 2% that of the luciferase activity in mice treated with a scrambled peptide (FIG. 8).

Figure 9:
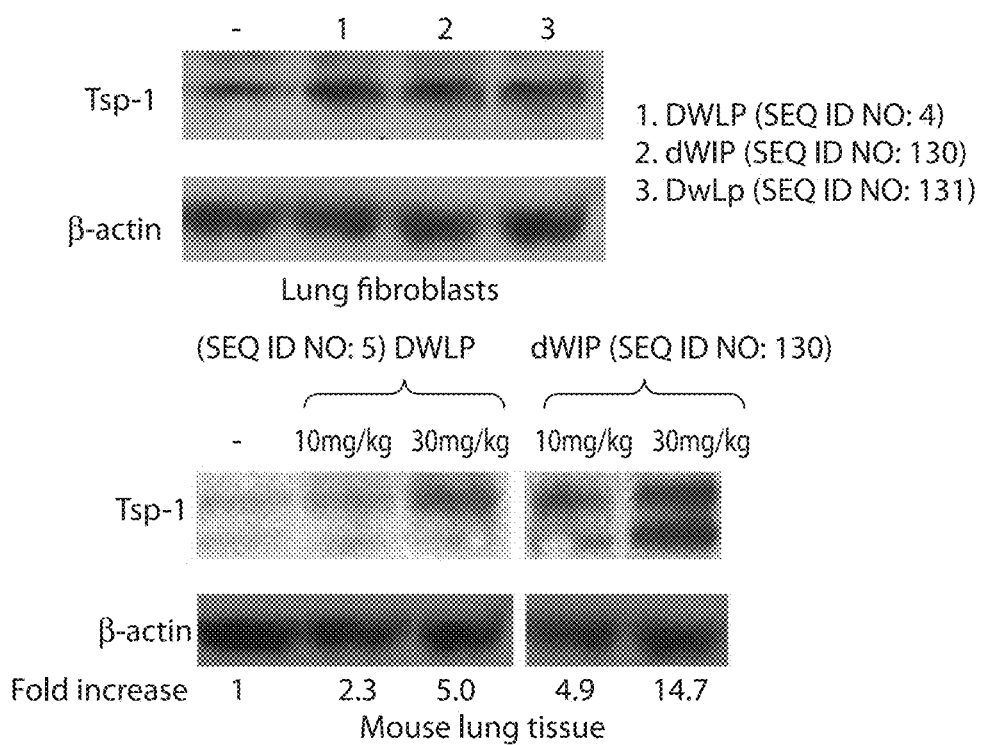
FIG. 9 is a photograph of experimental results obtained from Western blot analysis. Lower case letters indicate D-amino acids. Fold increase is Tsp-1/actin normalized relative to untreated. The experimental results indicate that D-amino acid substituted peptides further increased Tsp-1 expression in vivo but not in vitro.

Finally, the effect of substituting D-amino acids at different residues of the 4-amino acid peptide was analyzed. By Western blot analysis it was observed that substituting the first and third or second and fourth residues, in combination, had no effect on the Tsp-1 stimulating activity in vitro. These peptides were then tested in the tumor-free animal model described above. The normal 4-amino acid peptide and the D-amino acid substituted peptides were injected in combination with conditioned media from PC3M-LN4 cells in adult C57BI6 mice for 4 days at a dose of 10 or 30 mg/kg/day via i.p. injection. Mice were sacrificed 24 hours after the treatment on day 4. The lungs of these mice were harvested and analyzed the Tsp-1 expression by Western blot analysis. The D-amino acid peptide administered at a dose of 10 mg/kg/day was equivalent to the wild-type peptide administered at a dose of 30 mg/kg/day at stimulating Tsp-1. The D-amino acid substituted peptide stimulated Tsp-1 ~3-fold greater at the equivalent dose of 30 mg/kg/day compared to the wild-type peptide (FIG. 9).

Example 2: Further Peptide Data

Methods

Human and Mouse Plasma and Mouse Blood

Male human plasma (Lot # BCE012312PM1, K3 EDTA) was obtained from BioChemed Services (Winchester, Va.) and was stored at −80° C. Young adult male Swiss-Webster mice were obtained from Taconic Farms, and were anesthetized with carbon dioxide, and exsanguinated by cardiac puncture. Blood was collected in to tubes containing K2 EDTA and cooled in ice. Plasma was prepared by centrifugation for 10 min at 3000 g and 4° C. Mouse plasma and blood was used on the day of harvest.

Preparation of Standard Curves

Quenched matrix (human and mouse plasma) samples were prepared from one volume of plasma precipitated with three volumes of 9:1 acetonitrile:water at 4° C. and centrifuged for 10 min at 3000 g and 4° C., and the supernatant was used to prepare standard curve samples. A stock solution of 20 mg/mL Ac-DWLP-amide (SEQ ID NO: 133, Ac=acetyl group, amide=amide group) and 20 mg/mL Ac-dWlP-amide (SEQ ID NO: 132, DWLP with D-amino acids D and L indicated by lower case) was prepared in distilled water. Each peptide stock (20 mg/mL) was used to prepare a dilution in phosphate buffered saline (PBS) at 1 mg/mL and those samples were further diluted in PBS to prepare 100 and 50 μg/mL solutions. The 100 and 50 μg/mL solutions were added to the quenched matrix supernatant at concentrations equivalent to 0, 300, 1000, 3000, and 10000 ng/mL pre-quench plasma concentrations to prepare standard curve samples. Triplicate aliquots (100 μL) of each standard curve sample were diluted in 100 μL, water prior to analysis by LC/MS.

Incubation with Plasma and Blood

Plasma

The two peptides were formulated in PBS (40 μg/mL), and incubated with human and mouse plasma at 37° C. in polypropylene tubes at a concentration of 800 ng/mL in duplicate. Incubation aliquots (100 μL) were removed at 0, 15, 30, and 60 min and immediately quenched by the addition of 300 µL 9:1 acetonitrile:water, vortexed and centrifuged for 10 min at 3000 g and 4° C. Then 100 µL, of each supernatant was diluted with 100 µL PBS prior to analysis by LC/MS.

Blood

The two peptides were formulated as for plasma and introduced into mouse blood chilled in an ice bath at a concentration of 800 ng/mL in duplicate. Five minutes after adding to blood, plasma was prepared and duplicate aliquots were extracted (as above) and analyzed by LC/MS.

Analysis by LC/MS

Processed standard curve and incubation samples were analyzed using the method described in Table 1. The concentration of peptide in plasma was determined by extrapolation from the standard curve.

TABLE 1

LC/MS/MS Conditions

| Instrument: | API 4000 Triple Quadrupole Mass Spectrometer with Turboion Spray source (MS-900) Agilent 1100 Diode Array Detector Agilent 1100 Autosampler Agilent 1100 Binary Pumps Agilent 1100 Column Compartment Valco VICI EHMA Switching valve with Agilent 1100 Isocratic Bump | | |
|---|---|---|---|
| Chromatography Conditions: | Column: | Phenomenex Luna C18 (50 × 2 mm, 5 µm) with C18 guard cartridge | |
| | Injection vol.: | 10 µL | |
| | Mobile Phase: | A: 0.1% Formic acid in Water + 10 mM Ammonium Formate B: 0.1% Formic acid in Methanol + 10 mM Ammonium Formate | |
| | Flow: | 0.5 mL/min | |
| | | Time | % A |
| | Gradient: | 0 | 95 |
| | | 1 | 95 |
| | | 6 | 5 |
| | | 8 | 5 |
| | | 8.1 | 95 |
| | | 10 | 95 |
| | Valve: | 0-1 min - to waste 1-10 min - to MS | |
| | Make-up Solvent: MEOH:H$_2$O (50:50) at 100 µL/min | | |
| | Peptide Detection | 571.3→ 457.3 (DP = 101; CE = 17; CXP = 28) | |
| CAD: | 10 | | |
| CUR: | 10 | | |
| GS1: | 50 | | |
| GS2: | 50 | | |
| IS: | 4000 | | |
| TEM: | 550 | | |
| EP: | 10 | | |
| Dwell: | 75 msec | | |

Results

The standard curve parameters for each peptide are presented in Table 2. A simple linear regression model with 1/x weighting was employed for curve fitting. The standard curves met the requirements of the method. Note that the standard curve samples were inadvertently prepared 10-fold higher than specified in the protocol. The curves were linear over this range and the concentrations of all samples analyzed fell within the standard curve.

TABLE 2

Standard Curve Parameters

| Peptide/Species | Slope | Intercept | R$^2$ |
|---|---|---|---|
| Ac-dWlP-amide - Mouse (SEQ ID NO: 132) | 1.78 | −183 | 1.00 |
| Ac-dWlP-amide - Human (SEQ ID NO: 132) | 1.93 | −344 | 0.98 |
| Ac-DWLP-amide - Mouse (SEQ ID NO: 133) | 1.76 | −174 | 0.99 |
| Ac-DWLP-amide - Human (SEQ ID NO: 133) | 2.03 | −105 | 0.99 |

Figure 10:
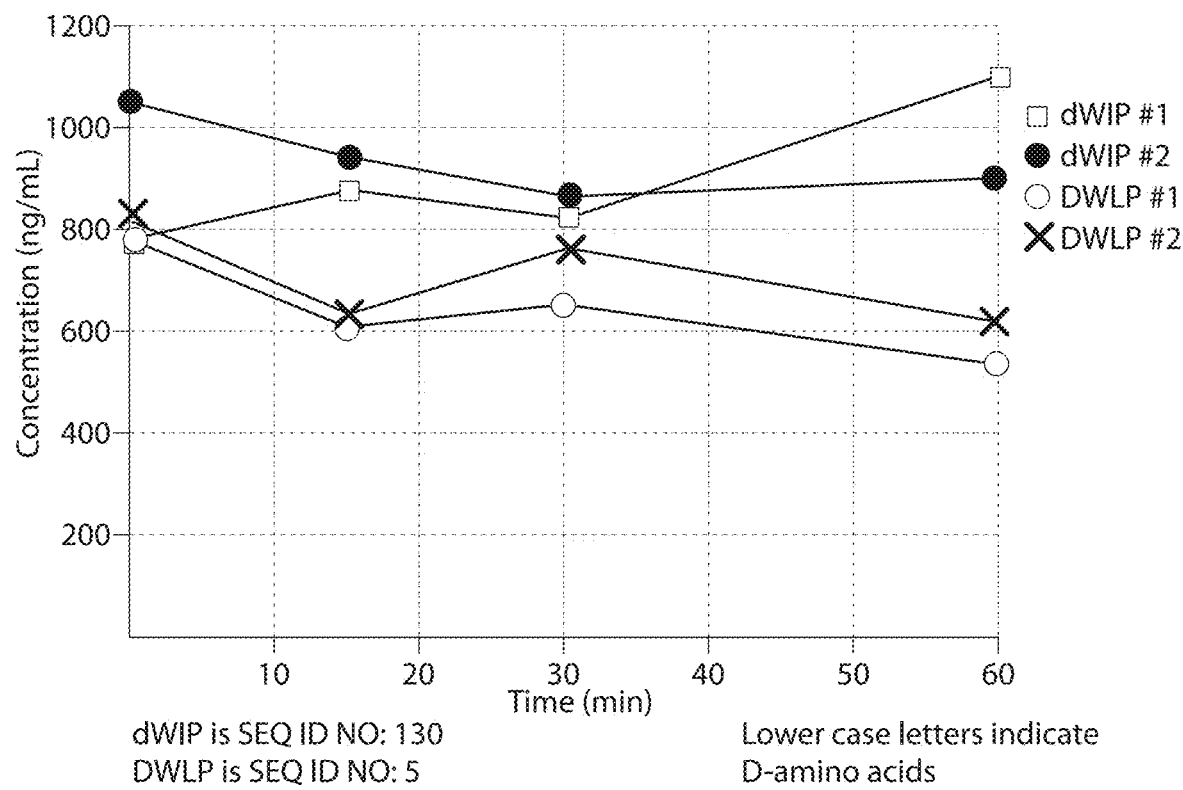
FIG. 10 is a graph of experimental results that indicate that the D-amino acid substitution peptides were more stable in human plasma.

The concentrations of Ac-dWlP-amide (SEQ ID NO: 132) measured in mouse and human plasma through 1 h of incubation at a concentration of 800 ng/mL are shown in Table 3 and FIG. 10. The data indicate that the peptide is stable in human plasma for 1 h at 37° C. The peptide is less stable in mouse plasma over this time period, with concentrations at 1 h about 56-59% of nominal. Most of the drop in Ac-dWlP-amide (SEQ ID NO: 132) concentration occurred in the first 15 min of incubation, with no significant decrease over the next 45 min.

TABLE 3

Concentration and Percent of Nominal Concentration of Ac-dWlP-amide (SEQ ID NO: 132) in Human and Mouse Plasma

| Species | Replicate | Time Point (min) | Concentration (ng/mL) | Percent of Nominal |
|---|---|---|---|---|
| Human | 1 | 0 | 779 | 97.4 |
| Human | 1 | 15 | 875 | 109.4 |
| Human | 1 | 30 | 818 | 102.3 |
| Human | 1 | 60 | 1100 | 137.5 |
| Human | 2 | 0 | 1050 | 131.3 |
| Human | 2 | 15 | 941 | 117.6 |
| Human | 2 | 30 | 863 | 107.9 |
| Human | 2 | 60 | 901 | 112.6 |
| Mouse | 1 | 0 | 858 | 107.3 |
| Mouse | 1 | 15 | 520 | 65.0 |
| Mouse | 1 | 30 | 541 | 67.6 |
| Mouse | 1 | 60 | 446 | 55.8 |
| Mouse | 2 | 0 | 859 | 107.4 |
| Mouse | 2 | 15 | 462 | 57.8 |
| Mouse | 2 | 30 | 496 | 62.0 |
| Mouse | 2 | 60 | 469 | 58.6 |

The concentrations of Ac-DWLP-amide (SEQ ID NO: 133) measured in mouse and human plasma through 1 h of incubation at a concentration of 800 ng/mL are shown in Table 4 and FIG. 10. The data indicate that the peptide has good stability (77-79% of nominal) through 1 h in incubation in human plasma and that the stability is lower in mouse plasma, with only 50-58% remaining after a 1-h incubation. Most of the drop in Ac-DWLP-amide (SEQ ID NO: 133) concentration occurred in the first 30 min of incubation, with no significant decrease over the next 30 min.

TABLE 4

Concentration and Percent of Nominal Concentration of Ac-DWLP-amide (SEQ ID NO: 133) in Human and Mouse Plasma

| Species | Replicate | Time Point (min) | Concentration (ng/mL) | Percent of Nominal |
|---|---|---|---|---|
| Human | 1 | 0 | 784 | 98.0 |
| Human | 1 | 15 | 817 | 102.1 |
| Human | 1 | 30 | 607 | 75.9 |
| Human | 1 | 60 | 634 | 79.3 |

TABLE 4-continued

Concentration and Percent of Nominal Concentration of Ac-DWLP-amide (SEQ ID NO: 133) in Human and Mouse Plasma

| Species | Replicate | Time Point (min) | Concentration (ng/mL) | Percent of Nominal |
|---------|-----------|------------------|-----------------------|--------------------|
| Human   | 2         | 0                | 649                   | 81.1               |
| Human   | 2         | 15               | 760                   | 95.0               |
| Human   | 2         | 30               | 538                   | 67.3               |
| Human   | 2         | 60               | 616                   | 77.0               |
| Mouse   | 1         | 0                | 869                   | 108.6              |
| Mouse   | 1         | 15               | 669                   | 83.6               |
| Mouse   | 1         | 30               | 428                   | 53.5               |
| Mouse   | 1         | 60               | 398                   | 49.8               |
| Mouse   | 2         | 0                | 955                   | 119.4              |
| Mouse   | 2         | 15               | 605                   | 75.6               |
| Mouse   | 2         | 30               | 400                   | 50.0               |
| Mouse   | 2         | 60               | 463                   | 57.9               |

The concentrations of Ac-dWlP-amide (SEQ ID NO: 132) and Ac-DWLP-amide (SEQ ID NO: 133) found in mouse plasma prepared from mouse blood that was incubated with 800 ng/mL of peptide are shown in Table 5. Typical hematocrit for a mouse is 0.4-0.5, corresponding to a plasma contribution of 50-60% of the blood volume. If the peptides remain in the plasma fraction, measured concentrations would be expected to range from 1333 to 1600 ng/mL. The measured concentrations range from 1010 to 1610 ng/mL, indicating that both peptides remain primarily in the plasma fraction and do not partition into red blood cells.

TABLE 5

Concentration of Ac-dWlP-amide (SEQ ID NO: 132) and Ac-DWLP-amide (SEQ ID NO: 133) in Mouse Plasma Prepared From Mouse Blood Incubated with Each Peptide.

| Peptide | Replicate | Concentration (ng/mL) |
|---------|-----------|-----------------------|
| Ac-dWlP-amide (SEQ ID NO: 132) | 1 | 1060 |
| Ac-dWlP-amide (SEQ ID NO: 132) | 1 | 1010 |
| Ac-dWlP-amide (SEQ ID NO: 132) | 2 | 1420 |
| Ac-dWlP-amide (SEQ ID NO: 132) | 2 | 1380 |
| Ac-DWLP-amide (SEQ ID NO: 133) | 1 | 1580 |
| Ac-DWLP-amide (SEQ ID NO: 133) | 1 | 1510 |
| Ac-DWLP-amide (SEQ ID NO: 133) | 2 | 1530 |
| Ac-DWLP-amide (SEQ ID NO: 133) | 2 | 1610 |

Example 3: Further Peptide Data

Methods: 18 C57B16 mice were injected with Ac-dWlP-amide (SEQ ID NO: 132) at a dose of 30 mg/kg in a volume of 100 µL via intraperitoneal (i.p) injections in serum starved conditioned media from PC3M-LN4 prostate cancer cells. The mice were separated into 6 groups of 3 mice, which were euthanized 4, 8, 16, 24, 48 and 72 hours after peptide injection. Subsequent to euthanasia the lungs were harvested from the mice, minced in a dounce homogenizer and lysed using REPA buffer on ice for 30 minutes. The tissue lysates were then centrifuged at 13,000 rpm in a table top minicentrifuge for 20 minutes at 4° C. The supernatants were then removed and mixed with 4x loading buffer and 100 µg of total protein (based on Bio-Rad assay) was loaded and electrophoresed on a 4-12% gradient bis-tris gel. Following electrophoresis the proteins were transferred to an Immobilon-P membrane (Millipore) for 2 hours at 200V. The membranes were then blocked in 5% non-fat milk in PBS-T for 40 minutes and then incubated with Tsp-1 ab-11 antibody (Labvision) and β-Actin antibody from AbCam overnight at 4° C. with rocking. The membranes were then washed 3 times for 10 minutes with PBS-T at room temperature with rocking and then incubated with goat anti-mouse antibody secondary antibody for one hour at room temperature with rocking. Following secondary antibody incubation the membranes were washed 3 times for 10 minutes in PBS-T at room temperature with rocking and then Pierce Super Signal developer was added for 1 minute. The membranes were then exposed to film to visualize the Tsp-1 and β-Actin bands. The relative intensity of the Tsp-1 (normalized to β-Actin) bands were determined using a Bio-Rad Chemi-Doc XRS system.

Figure 11:
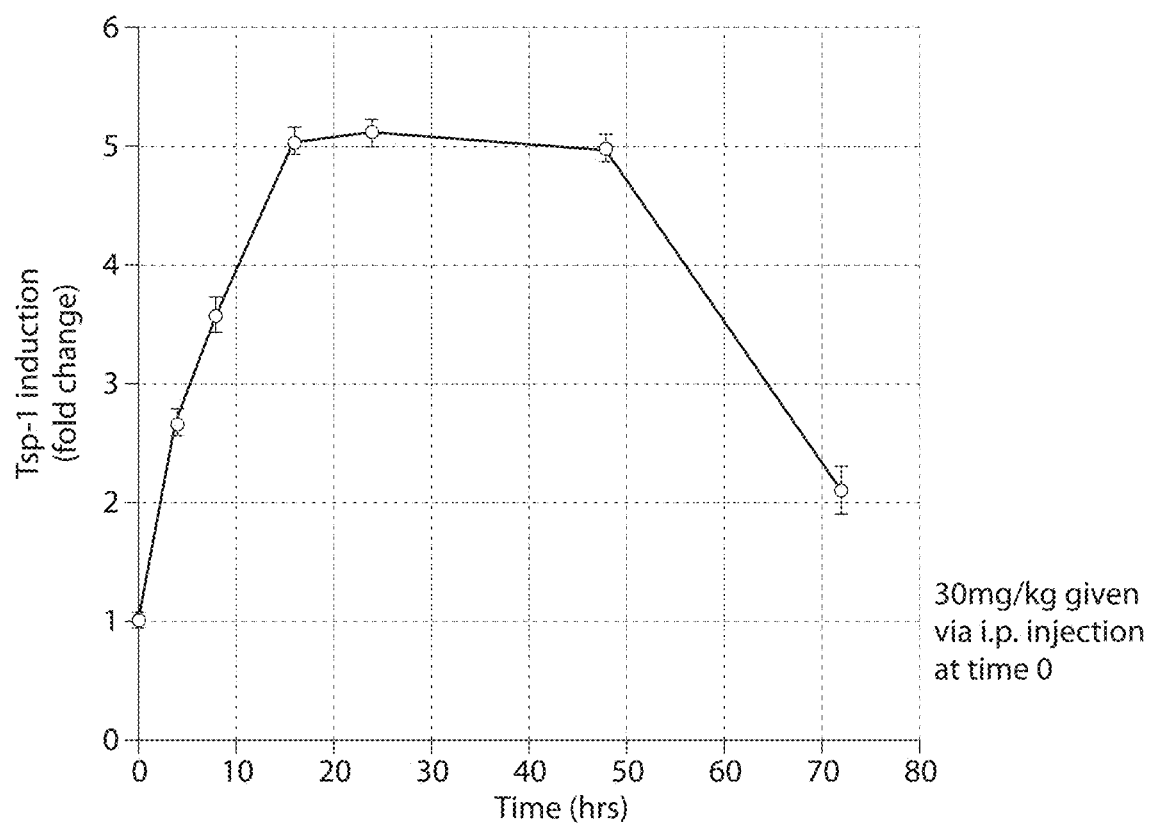
FIG. 11 is a graph of experimental results that indicate that the Psap peptide Ac-dWlP-amide (SEQ ID NO: 132, DWLP with D-amino acids D and L) induces Tsp-1 expression.

Results:

In order to determine the kinetics of Tsp-1 induction by Ac-dWlP-amide (SEQ ID NO: 132, DWLP with D-amino acids D and L indicated in lower case) in vivo C57B16 mice were treated with Ac-dWlP-amide (SEQ ID NO: 132) at a dose of 30 mg/kg in combination with PC3M-LN4 CM via i.p injection. Mice were euthanized at 4, 8, 16, 24, 48 and 72 hours post-injection and Tsp-1 induction was measured in the lungs of mice by western blot analysis. Tsp-1 induction reached a peak of 5-fold by 16 hours and remained at that level until 48 hours post-injection (FIG. 11). By 72 hours post-induction the Tsp-1 levels had dropped to 2-fold greater than baseline.

Example 4: Further Peptide Data

Methods:

PC3 or PC3M-LN4 cells were cultured in RPMI with 10% FBS. $5 \times 10^6$ cells were then subcultured in serum-free medium for 24 hours in order to generate conditioned media. Harvested media was centrifuged and filtered through 0.22₁.11V1 pore-size filters to remove any cells or cell debris. Wild-type BMT and Tsp-1–/– BMT C57BL/6J mice were pretreated with 200 µL serum-free conditioned media from PC3 or LN4 cells or serum-free RPMI media daily for 6 days via intraperitoneal (i.p.) injection.

Animals were euthanized at the end of experiments and lungs were quickly perfused by injecting 5 ml of cold PBS through the right ventricle of the heart. One part of the lung from each animal was fixed in 3.7% formalin and the other part was sorted by flow cytometry for either protein or RNA extraction.

For microscopy, following formalin fixation, tissues were cryoembedded in Tissue-Tek O.C.T. embedding compound (Electron Microscopy Sciences). Sections (30 µm) were washed 3 times in PBS and incubated in blocking/permeabilization buffer (PBS+2 mM EDTA, 1% BSA, 1% Goat Serum, 0.05% Triton X-100). Sections were then incubated with labeled primary antibodies against GR1 (Clone RB6-8C5, BD Pharmingen), CD11b (Clone M1/70, BD Pharmingen), Tsp-1 (Ab-4 Neomarkers), for 1 hour at room temperature. Primary antibodies were diluted in blocking/permeabilization buffer at a dilution of 1:100. After primary antibody incubation, sections were rinsed 5 times with PBS, counter-stained with DAPI and mounted in Prolong Gold-antifade reagent for epifluorescence microscopy analysis.

Results:

Immunostaining analysis was performed to determine the source of Tsp-1 in the lung stroma, and Tsp-1 expression was observed to be largely confined to the BM-derived CD11b+ hematopoietic cells recruited in the lungs of mice treated with PC3 CM. Strikingly this expression pattern was not observed in the lungs of mice treated with LN4 CM (FIG. 12). Analysis of flow sorted cells showed that Tsp-1 was expressed by Gr1+ myeloid progenitor cells and not the Gr1− stromal cells (FIG. 12), consistent with immunostaining analysis showing that Tsp-1 expression was confined to a subset of Gr1+ cells (FIG. 12).

Example 5: Psap and Prostate Cancer

Methods:

Archival specimens (radical prostatectomy specimens, or biopsies of metastases) were retrieved from files of Department of Pathology, The Gade Institute, Haukeland University Hospital. Formalin fixed prostatectomy specimens were paraffin embedded and studied by whole mount step sections at 5 mm intervals. Tissue microarrays (TMAs) were constructed selecting three tissue cores (0.6 mm in diameter) from the area of highest tumor grade in each case.

Thin paraffin sections (5 μm) from the TMA paraffin block were dewaxed with xylene/ethanol before heat induced microwave epitope retrieval in citrate buffer (pH 6.0) for 20 minutes, and incubated with a polyclonal Prosaposin antibody (H-81) (sc-32875, Santa Cruz Biotechnology, Calif.), diluted 1:2000 for 60 minutes at room temperature. Immunostaining was performed on the DAKO Autostainer with the EnVision chain polymer method (Dako Cytomation, Copenhagen, Denmark) as detection system. Antigen localization was achieved using the DAB diaminobenzidine peroxidase reaction, counterstained with hematoxylin.

Immunostaining was estimated semiquantitatively, and a staining index (SI) obtained as a product of staining intensity (0-3) and proportion of immunopositive tumor cells (<10%=1, 10-50%=2, >50%=3), was calculated. The staining index (range 0-9) is a categorical scale, where some variation within each category is expected. Cases with a staining index <3 were defined as low expressors.

Correlations between variables were assessed by Pearson's chi-square test, Kruskal-Wallis test, or Mann-Whitney U test (SPSS statistical package; SPSS, Inc., Chicago, Ill.).

The study population consisted of 219 patients with primary localized carcinomas (n=104, median age 62.0 years), castration resistant primary carcinomas (n=33), metastases from prostate cancers (n=41), or benign prostate hyperplasia (n=41), all treated at Haukeland University Hospital, Bergen, Norway (1988-1994), with complete follow-up included. Clinical stage T1/T2 disease, negative bone scan and general good health with 10 to 15 years life expectancy were the prerequisites for surgery of primary localized carcinomas. During follow-up, patients received anti-androgen treatment after biochemical failure, and external beam radiotherapy after local recurrence. Information on disease course was compiled from institutional examinations, and hospital records or correspondence with general practitioners. Time from surgery until biochemical failure, defined as s-PSA elevation >0.5 ng/ml in two consecutive blood samples, was recorded, as was time to clinical locoregional recurrences, metastases or death from prostate cancer. A palpable tumor in the prostate fossa or evidence of distant metastases on bone scan, X-ray or MRI was recorded as clinical recurrence. The study was approved by The Regional Ethical Committee for Medical Research.

Results:

To determine psap expression in cancer patients, prosaposin levels were evaluated in tissue samples from 219 prostate cancer patients with disease stages ranging from prostate hyperplasia to metastases by IHC on tissue microarray (TMA) slides. It was observed that patients with localized prostate cancer had a psap expression level, as estimated by the categorical staining index (range 0-9), which was significantly lower than patients with prostate hyperplasia. These results were highly statistically significant with a p-value of <0.0005 by Kruskal-Wallis analysis (FIG. 13). Additionally, a consecutive series of 104 men treated by radical prostatectomy for prostate cancer (Haukeland University Hospital, Bergen, Norway) and with long and complete follow-up, was included in this study (Suppl. info.). Immunohistochemical analysis of prosaposin protein expression in a tissue microarray revealed an association between low prosaposin expression and adverse features such as high pre-operative serum-PSA (P=0.025), extraprostatic tumor extension (trend; P=0.077), and time to biochemical failure (P=0.027) and cancer specific survival (P=0.036) (FIG. 13).

Example 6: Further Peptide Data

Methods:
See Example 5 methods
Results:

Next, it was determined whether psap expression in primary prostate carcinomas correlated with other clinicopathologic features of prostate cancer. Specifically, based on immunohistochemical analysis of prosaposin protein expression in tumor cells, it was found that there was an association between low prosaposin expression and more aggressive tumor features such as increased preoperative serum-PSA levels, a tendency for higher Gleason score, and more extra-prostatic extension. Regarding multivariate survival analysis, PSAP had an independent influence on time to clinical recurrence (p=0.074) in addition to Gleason score, whereas pT and PSA dropped out of this model (FIG. 14). Moreover, and significantly, regarding overall patient survival, PSAP was indeed independently significant (p=0.020), as the only factor in this model, thus being stronger than Gleason score, pT and PSA (FIG. 14). These findings suggest that analysis of psap expression could potentially be useful for predicting disease recurrence or outcome.

Figures 1, 15:
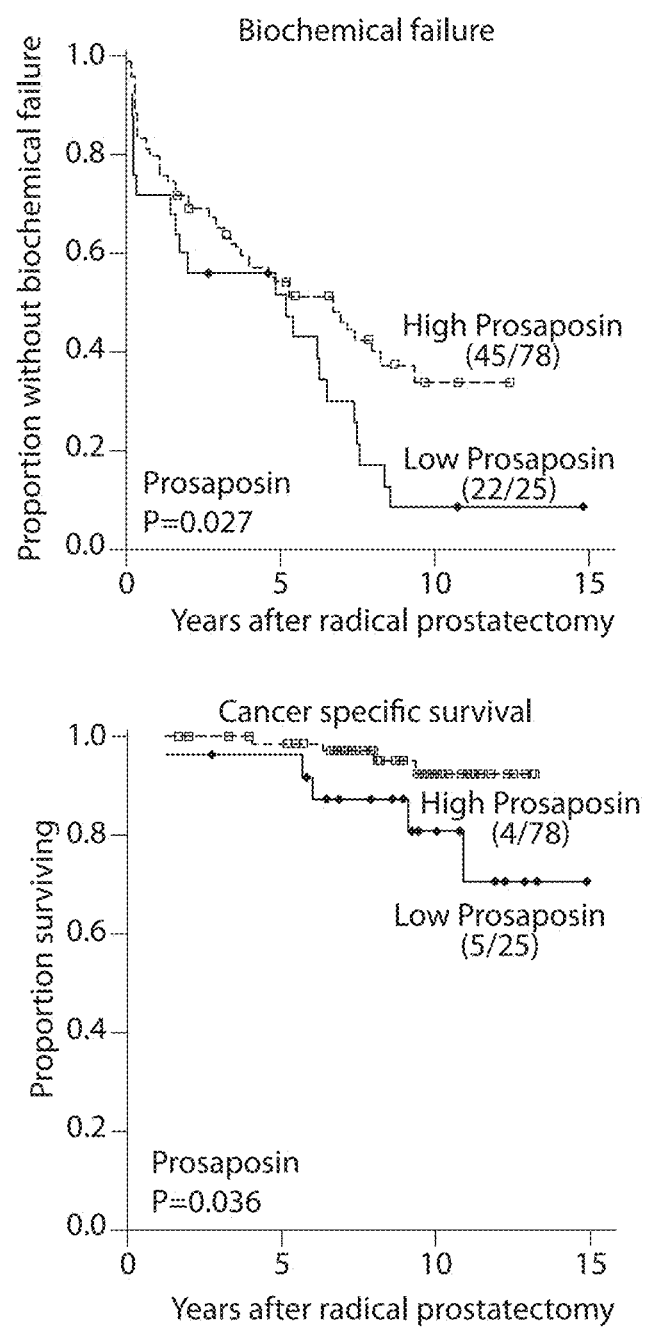
FIG. 15 is three graphs and two photographs of experimental results indicating that Psap correlates with patient survival and biochemical failure.
Figure 15:
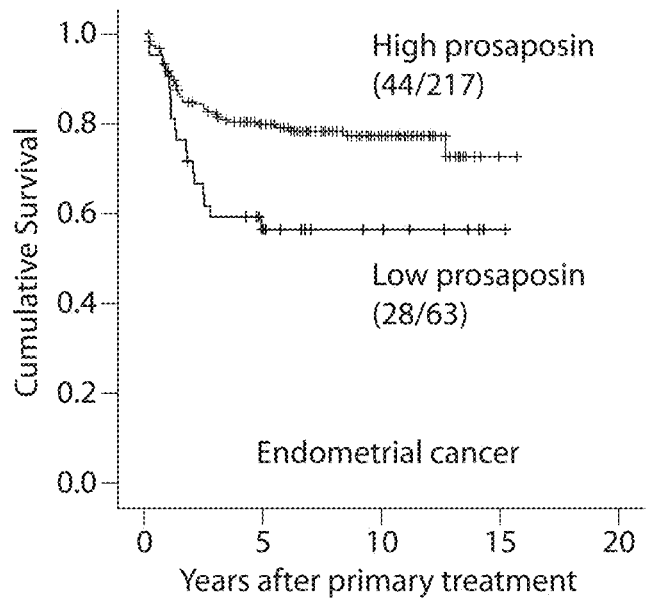
Figure 2:
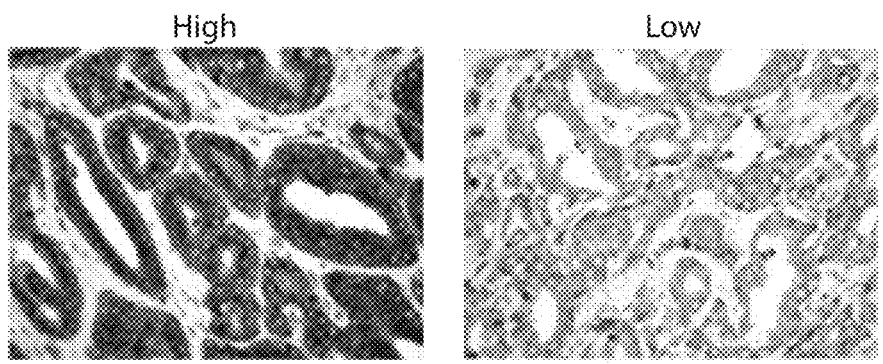

Example 7: Psap Associated with Time to Biochemical Failure and Cancer Specific Survival Methods:
See Example 5 methods.
Results:

Prosaposin (psap) is a tumor-secreted protein that inhibits metastasis to distant organs in syngeneic and xenograft models. In this study, the correlation was examined between prosaposin expression and patient survival. As such, psap expression was analyzed in a consecutive series of 104 men treated by radical prostatectomy for prostate cancer (Haukeland University Hospital, Bergen, Norway) for whom there was long and complete follow-up. Immunohistochemical analysis of psap protein expression revealed that weak psap staining was associated with reduced time to biochemical failure (P=0.027) as well as cancer specific survival (P=0.036) (FIG. 15). Additionally, patients with endometrial cancer also had an association between cancer specific survival and levels of Psap (FIG. 15). Thus, it appears that patients with high levels of Psap establish a barrier to tumor progression. Additionally, it appears that Psap expression levels identify patients who are likely to respond or are responsive to treatment.

Example 8: Further Peptide Data

Methods:

C57Bl6 mice were injected with 5×10^5 B16-B16 melanoma cells subcutaneously. After 8 days the mice were treated with either Ac-dWlP-amide (SEQ ID NO: 132, DWLP with D-amino acids D and L indicated as lowercase letters) at a dose of 40 mg/kg QD, DTIC (dacarbazine)' at a dose of 80 mg/kg QOD, Ac-dWlP-amide (SEQ ID NO: 132)+DTIC at the same doses, or PBS QD. Tumor diameter was measured every other day using calipers. After 24 days all mice were euthanized and the tumors harvested for immunohistochemistry or western blot analysis.

Figure 16:
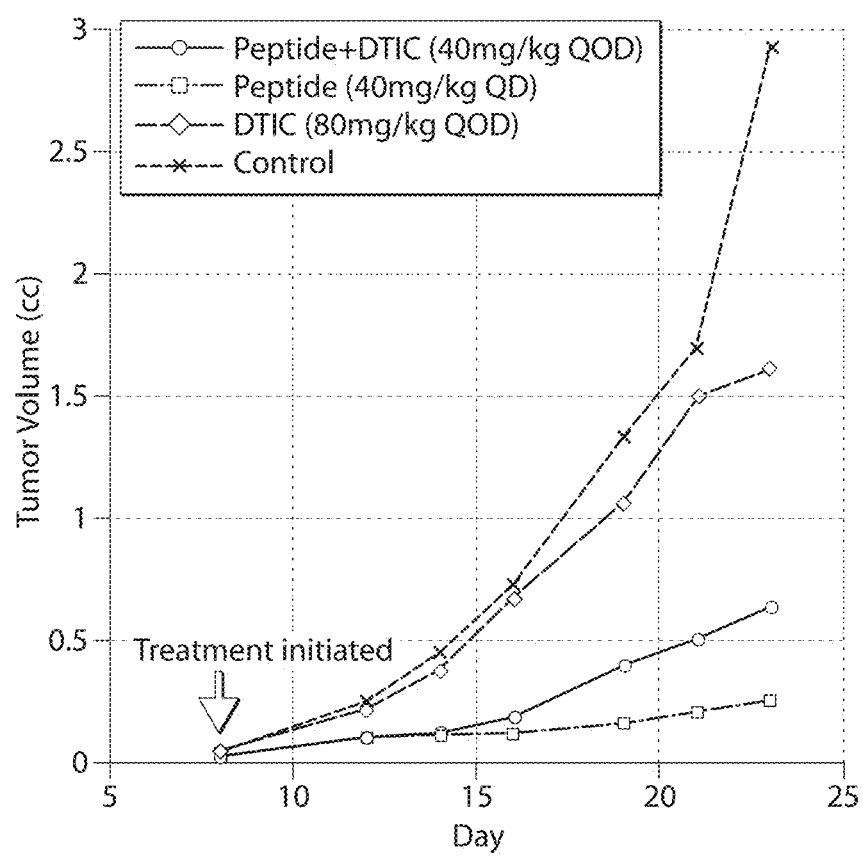
FIG. 16 is a graph of experimental results indicating that B16-B16 melanoma growth is inhibited by a prosaposin-derived dWlP (SEQ ID NO: 130) peptide.

Results:

The Inventors sought to determine whether Ac-dWlP-amide (SEQ ID NO: 132) could inhibit the growth of aggressive primary tumors and thus chose the murine melanoma cell line B16-B16. 5×10^5 cells were injected subcutaneously into syngeneic C57Bl6 mice. Treatment was initiated with Ac-dWlP-amide (SEQ ID NO: 132), DTIC, Ac-dWlP-amide (SEQ ID NO: 132)+DTIC, or PBS (control) 8 days after injection and tumor diameter was measured every other day for 24 days. Treatment with Ac-dWlP-amide (SEQ ID NO: 132) alone was able to virtually block all tumor growth with a t/c of 98% compared to PBS treated, control mice (FIG. 16). The Ac-dWlP-amide (SEQ ID NO: 132) was also significantly more effective than DTIC alone or in combination with the Ac-dWlP-amide (SEQ ID NO: 132).

Example 9: Further Peptide Data

Methods:

See Example 6 and 8 methods

Figure 17:
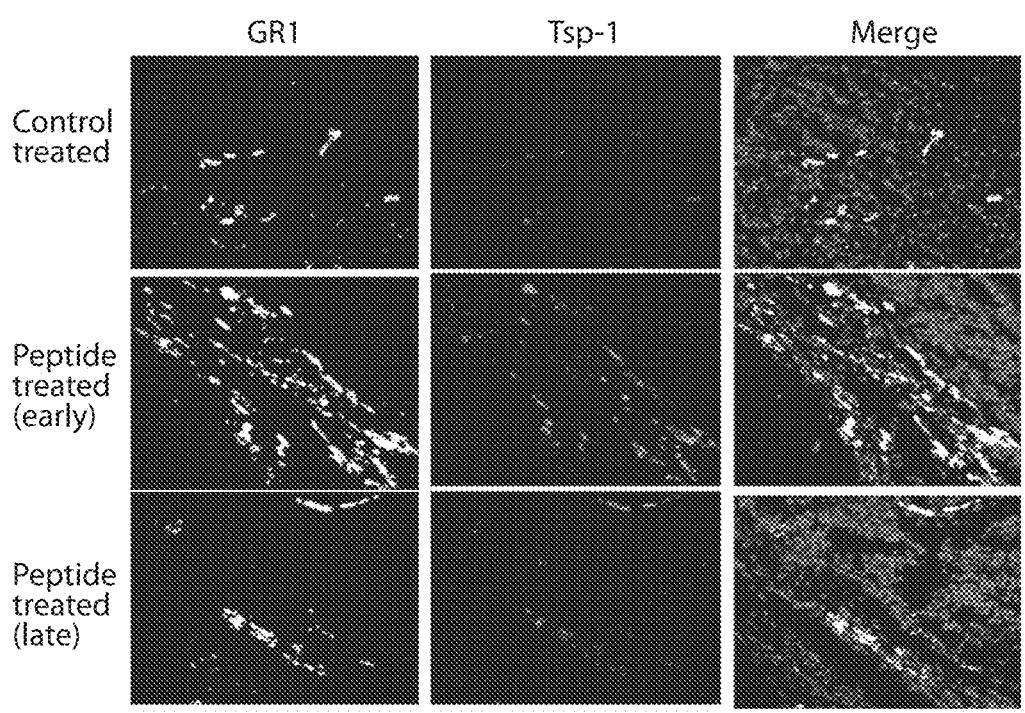
FIG. 17 is a series of photographs of tissue staining indicating that Psap peptide treatment stimulates Tsp-1 in GR1 cells in primary melanomas.

Results:

Frozen sections of B16-B16 tumors were stained with antibodies against Gr1 and Tsp-1 to determine whether these tumors recruited bone-marrow derived monocytes and whether Ac-dWlP-amide (SEQ ID NO: 132) could induce Tsp-1 in these cells. It was observed that control treated tumors recruited Gr1 cells but these cells did not express Tsp-1 (FIG. 17). Significantly, it was observed that Ac-dWlP-amide (SEQ ID NO: 132) treated tumors not only recruited Gr1 cells but that these cells were induced to express Tsp-1. These results demonstrate that the mechanism of Ac-dWlP-amide (SEQ ID NO: 132) activity is not confined to metastases but also holds for primary tumors.

Example 10: Further Peptide Data

Methods:

For orthotopic breast cancer cell injections, 5×10^6 viable MDA-MB-231 or its metastatic variant MDA-MB-LM2 cells, were injected into CB-17 SCID mice fat pads in a volume of 0.1 ml. Tumor growth and pulmonary metastases (following resection of primary tumor) were monitored by live animal bioluminescence imaging (Xenogen) once per week. For orthotopic prostate cancer cell injections, 2×10^6 viable LN4 or LN4-psap cells were injected into the prostate gland of mice. For in vivo determination of the metastatic burden, mice were anaesthetized and injected intraperitoneally with 75 mg/kg of D-luciferin (100 uL of 30 mg/mL in PBS). Metastatic growth was monitored over time using bioluminescence imaging performed with mice in a supine position 5 min after D-luciferin injection with a Xenogen IVIS system coupled to Living Image acquisition and analysis software (Xenogen). For BLI plots, photon flux was calculated for each mouse by using the same circular region of interest encompassing the thorax of the mouse.

Figure 18:
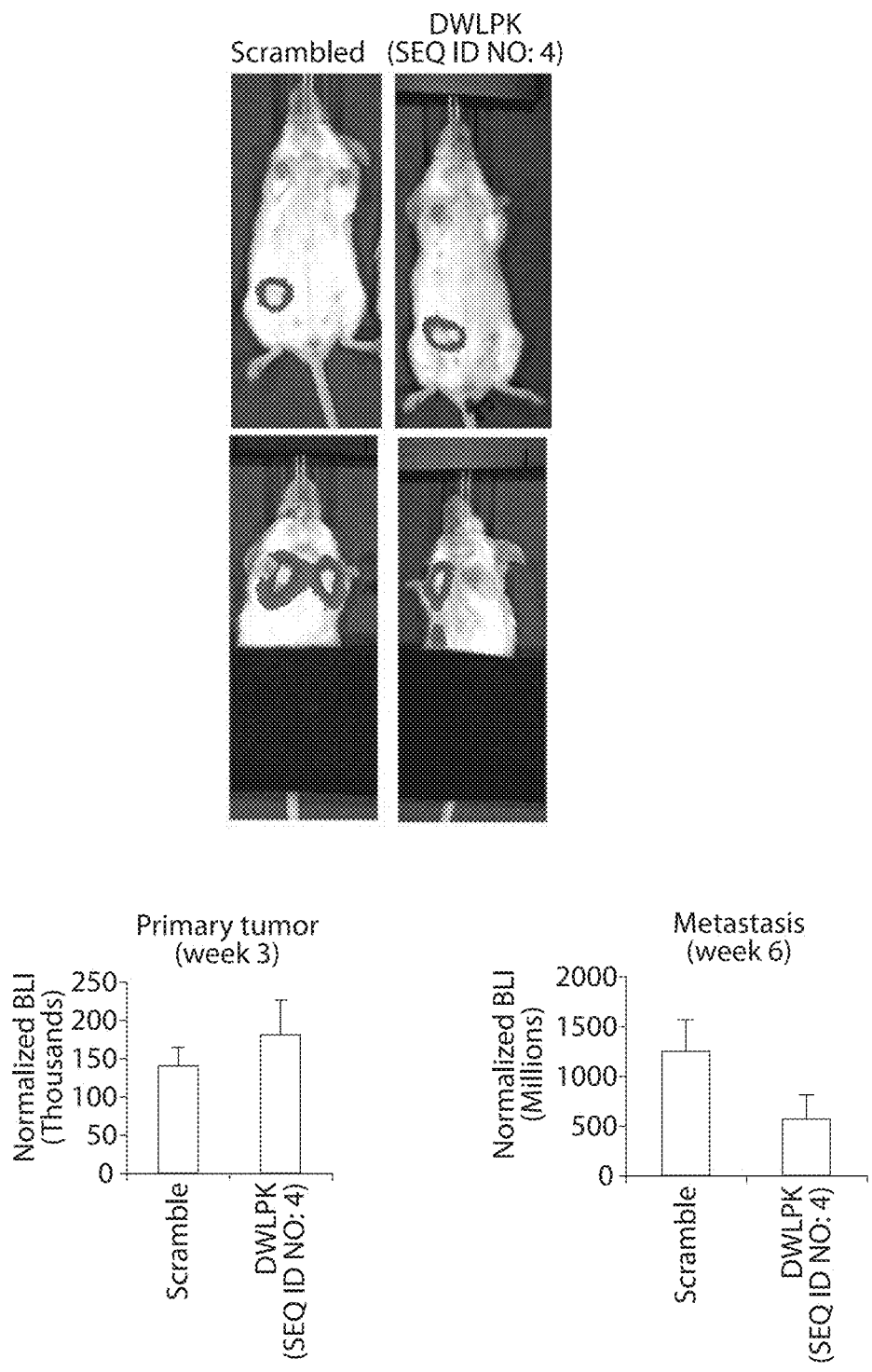
FIG. 18 is a photograph and graphs of experimental data indicating that Psap peptide treatment inhibits breast cancer metastasis.
Figure 19:
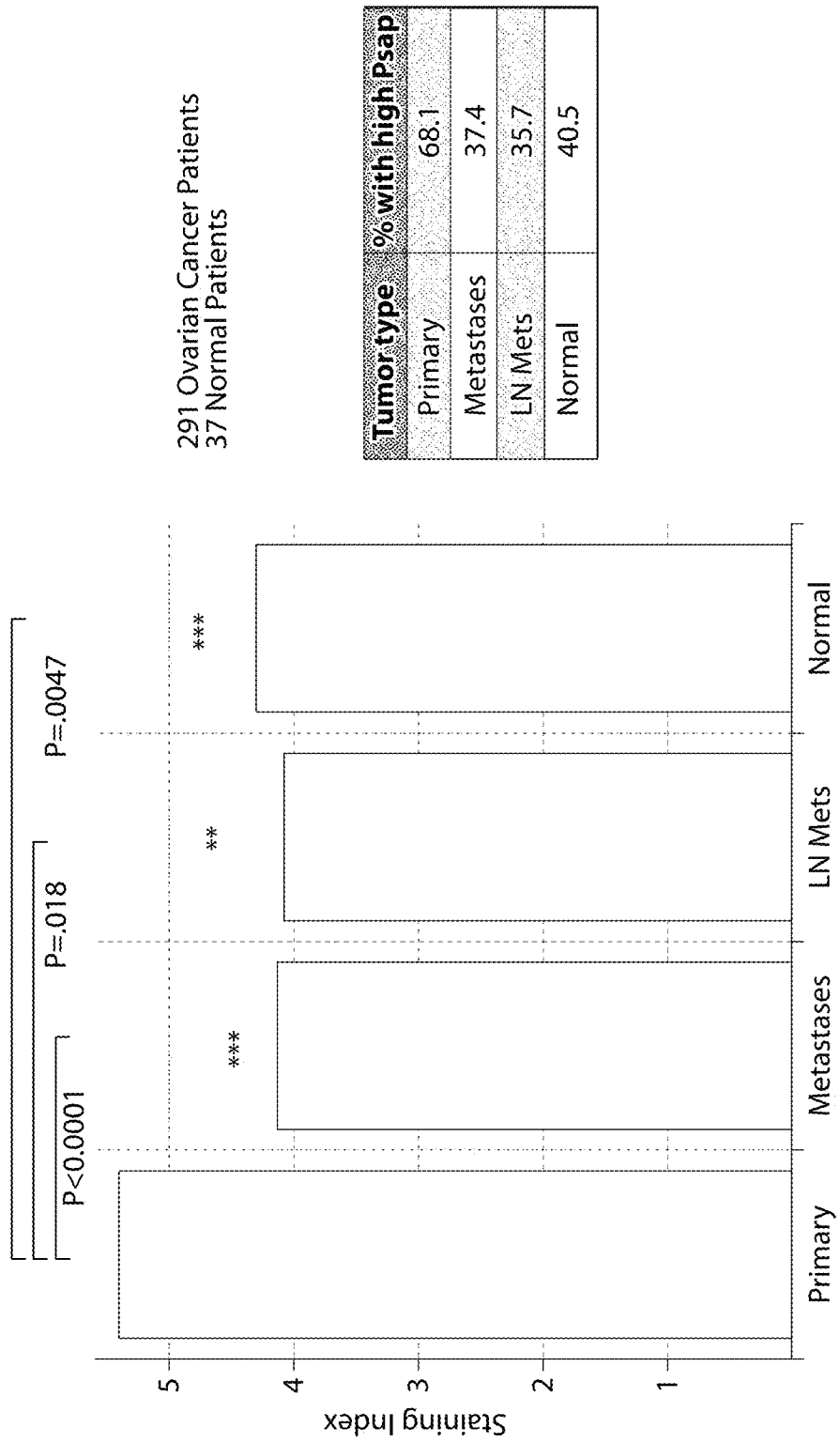
FIG. 19 is a graph and table of experimental results that indicate that Psap levels correlate with disease progression for ovarian cancer patients

Results:

The ability of the DWLPK (SEQ ID NO: 4) peptide to inhibit metastasis was tested in an orthotopic, clinically relevant, model of breast cancer metastatic to the lung. Metastatic MDA-MB-231-LM2 breast cancer cells expressing the luc reporter were injected orthotopically in the mammary glands of SCID mice. After three weeks of growth (FIG. 19) primary tumors were surgically resected, and one cohort of mice was treated daily with DWLPK (SEQ ID NO: 4) peptide and another cohort with a scramble peptide. Lung metastases were assessed 3 weeks after the primary tumor removal (week 6 after primary tumor injection). In DWLPK (SEQ ID NO: 4)-treated mice, the metastatic burden in the lungs was significantly reduced by 50% (FIG. 19). Consistent with previous observations, DWLPK (SEQ ID NO: 4) treated lungs showed persistent Tsp-1 upregulation in the Gr1+ myeloid compartment compared to treatment with scrambled peptide (FIG. 18). Taken together, these results indicate that the 5-amino acid DWLPK (SEQ ID NO: 4) peptide, via induction of Tsp-1 in Gr1+ BM-derived cells in the lung microenvironment, could have significant efficacy in treating metastatic cancer.

Example 11: Further Correlations Between Psap and Cancer

Methods:

Archival specimens were retrieved from biopsies of ovarian cancer patients of the Department of Pathology, Dana Farber Cancer Institute (Boston, Mass.). Formalin fixed specimens were paraffin embedded and studied by whole mount step sections at 5 mm intervals. Tissue microarrays (TMAs) were constructed selecting three tissue cores (0.6 mm in diameter) from the area of highest tumor grade in each case. Thin paraffin sections (5 µm) from the TMA paraffin block were dewaxed with xylene/ethanol before heat induced microwave epitope retrieval in citrate buffer (pH 6.0) for 20 minutes, and incubated with a polyclonal Prosaposin antibody (H-81) (sc-32875, Santa Cruz Biotechnology, Calif.), diluted 1:2000 for 60 minutes at room temperature. Immunostaining was performed on the DAKO Autostainer with the EnVision chain polymer method (Dako Cytomation, Copenhagen, Denmark) as detection system. Antigen localization was achieved using the DAB diaminobenzidine peroxidase reaction, counterstained with hematoxylin.

Immunostaining was estimated semiquantitatively, and a staining index (SI) obtained as a product of staining intensity (0-3) and proportion of immunopositive tumor cells (<10%=1, 10-50%=2, >50%=3), was calculated. The staining index (range 0-9) is a categorical scale, where some variation within each category is expected. Cases with a staining index <3 were defined as low expressors.

Correlations between variables were assessed by Pearson's chi-square test, Kruskal-Wallis test, or Mann-Whitney U test (SPSS statistical package; SPSS, Inc., Chicago, Ill.).

Results:

The Inventors sought to determine whether there was any correlation between prosaposin expression and ovarian cancer metastasis. As such, a tissue microarray (TMA) compiled from 165 ovarian cancer patients and 37 normal patients was stained. It was determined that metastatic ovarian tumors expressed ~20% lower levels of prosaposin which was statistically significant to a p-value of <0.0001 as assessed by Mann-Whitney U test (FIG. 19). It was also determined that 68.1% of all primary ovarian tumors had a high prosaposin staining intensity (>6), while only 37.4% of metastases had a high prosaposin staining (>6).

Example 12: Further Peptide Data

Methods:

For metastatic ovarian cancer cell injections, $5 \times 10^6$ viable primary ovarian cancer cells were injected into CB-17 SCID mice intraperitoneally in a volume of 0.1 ml. Tumor growth was monitored by live animal bioluminescence imaging (Xenogen) once per week. For in vivo determination of the metastatic burden, mice were anaesthetized and injected intraperitoneally with 75 mg/kg of D-luciferin (100 uL of 30 mg/mL in PBS). Metastatic growth was monitored over time using bioluminescence imaging performed with mice in a supine position 5 min after D-luciferin injection with a Xenogen IVIS system coupled to Living Image acquisition and analysis software (Xenogen). For BLI plots, photon flux was calculated for each mouse by using the same circular region of interest encompassing the abdomen of the mouse.

Figure 20:
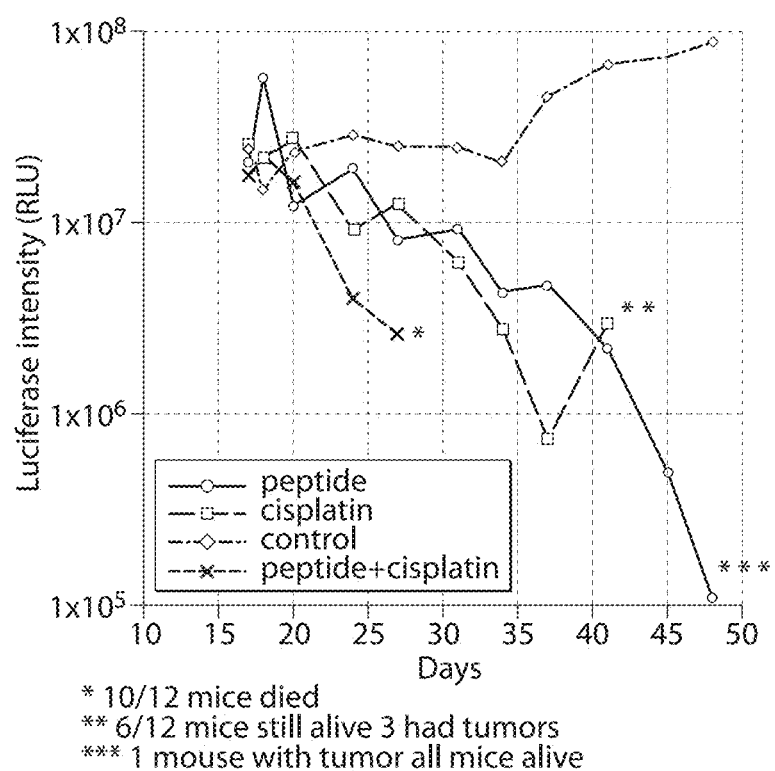
FIG. 20 is a graph of experimental results indicating that Psap peptide regresses metastatic ovarian cancer.

Results:

To determine whether DWLPK (SEQ ID NO: 4) could inhibit or regress existing ovarian metastases $5 \times 10^6$ primary ovarian cancer cells were injected intraperitoneally into SCID mice. After 17 days treatment was initiated with DWLPK (SEQ ID NO: 4) at a dose of 40 mg/kg QD, cisplatin at a dose of 2 mg/kg QOD, a combination of DWLPK (SEQ ID NO: 4) and cisplatin at the same doses, or PBS (control). It was observed that DWLPK (SEQ ID NO: 4) treatment completely regressed the metastases in 11/12 after 30 days and the regressed the metastases in the remaining mice by 99% (FIG. 20). Strikingly the tumors developed resistance to cisplatin treatment after 20 days and began growing again.

Example 13: Further Peptide Data

Methods:

Ascites fluid was collected from mice following euthanasia by injecting the peritoneal cavity with 5 mL of PBS and then draining the cavity and collecting the fluid.

Cells were washed; strained and resuspended in FACS staining buffer (PBS+2 mM EDTA, 1% BSA). For analysis of peripheral blood, blood was collected from the tails of mice in anti-coagulant buffer 22 (PBS with 5 mM EDTA). Red blood cells were eliminated by incubation in Lysis Buffer (BD Bioscience) for 10 min at RT. Cell suspensions were pre-blocked with 2% FBS plus Fc block (CD16/CD32, 1:30, BD Biosciences Pharmingen) and then incubated with the following primary antibodies: rat IgG2αк and IgG2αβ isotype control (BD Pharmingen), Gr1 (Clone RB6-8C5, Biolegend), CD11b (clone M1/70, BD Pharmingen), SYTOX blue (Invitrogen) was added and incubated for 30 minutes at room temperature in each cell staining tube to facilitate the elimination of dead cells in flow cytometry. Labeled cell populations were measured by LSRII flow cytometer coupled with FACSDiva software (BD Bioscience). Flow cytometry analysis was performed using a variety of controls including isotype antibodies, fluorescence minus one (FMO) samples (31), and unstained samples for determining appropriate gates, voltages, and compensations required in multivariate flow cytometry. For sorting, targeted cell populations were gated within FACSDiva software and sorted by Aria H sorter (BD Bioscience).

Figure 21:
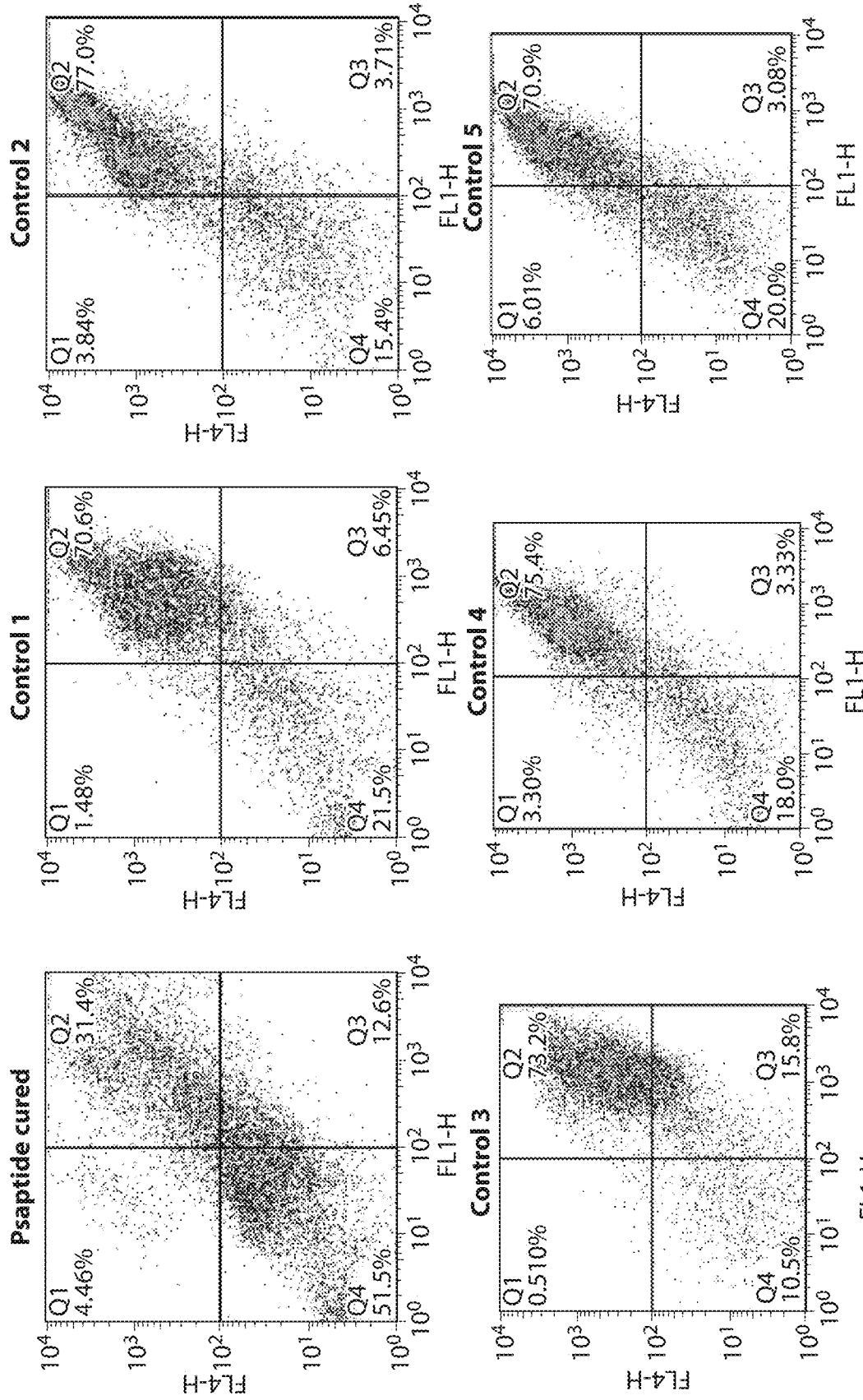
FIG. 21 is a series of graphs of FACS data indicating that Ovarian Cancer Ascites recruit Cd11b+/Gr1+ BM-derived cells.

Results:

The Inventors sought to determine whether ovarian cancer intraperitoneal metastases and ascites recruited GR1+/Cd11b+bone marrow-derived monocytes. As such ascites fluid was collected from control (PBS) and Ac-dWlP-amide (SEQ ID NO: 132) treated mice and assessed the GR1+/Cd11b+content by FACS. It was observed that >70% of the cells in the ascites fluid of control treated mice were GR1+/Cd11b+, compared to less than 30% in mice that had been "cured" by Ac-dWlP-amide (SEQ ID NO: 132) (FIG. 21).

Example 14: Further Peptide Data

Methods:

For experimental metastasis, 7-week old C57BL/6 mice were injected via tail vein with 1×105 luciferase-labeled LLC cells. Metastatic growth was monitored over time using bioluminescence imaging performed with mice in a supine position 5 min after D-luciferin injection with a Xenogen IVIS system coupled to Living Image acquisition and analysis software (Xenogen). For BLI plots, photon flux was calculated for each mouse by using the same circular region of interest encompassing the thorax of the mouse.

Results:

To determine if DWLPK (SEQ ID NO: 4) stimulation of Tsp-1 by BM Gr1+ cells in the lung parenchyma confers a metastasis-resistant niche, LLC-luc cells were administered via tail vein into wild-type mice treated with either DWLPK (SEQ ID NO: 4) peptide or scrambled control. Strikingly, administration of the DWLPK (SEQ ID NO: 4) peptide dramatically reduced lung metastases compared to the scrambled peptide, as measured by bioluminescence imaging (BLI) (FIG. 22).

Example 15: Further Peptide Data

Methods:

CM from PC3M-LN4 cells cultured in serum-free medium for 24 hours was harvested, centrifuged and filtered through 0.22 µM pore-size filters to remove any cells or cell debris. Wild-type C57BL/6J mice were treated with 200 µL serum-free conditioned media from PC3M-LN4 cells daily for 6 days via intraperitoneal (i.p.) injection in combination with DWLPK (SEQ ID NO: 4) peptide or scrambled peptide.

Animals were euthanized at the end of experiments and lungs were quickly perfused by injecting 5 ml of cold PBS through the right ventricle of the heart. One part of the lung from each animal was fixed in 3.7% formalin and the other part was sorted by flow cytometry for either protein or RNA extraction.

For microscopy, following formalin fixation, tissues were cryoembedded in Tissue-Tek O.C.T. embedding compound (Electron Microscopy Sciences). Sections (30 µm) were washed 3 times in PBS and incubated in blocking/permeabilization buffer (PBS+2 mM EDTA, 1% BSA, 1% Goat Serum, 0.05% Triton X-100). Sections were then incubated with labeled primary antibodies against GR1 (Clone RB6-8C5, BD Pharmingen) and Tsp-1 (Ab-4 Neomarkers/Labvision), for 1 hour at room temperature. Primary antibodies were diluted in blocking/permeabilization buffer at a dilution of 1:100. After primary antibody incubation, sections were rinsed 5 times with PBS, counter-stained with DAPI and mounted in Prolong Gold-antifade reagent for epifluorescence microscopy analysis.

Total RNA from flow cytometry sorted cells was extracted using the PicoPure RNA extraction kit (Arcturus) following the manufacturer's protocol. RNA was converted to cDNA using qScript™ cDNA supermix (Quanta biosciences). Q-PCR was performed with primers and iQ™ SYBER Green master mix (Biorad, Hercule, Calif.). Each sample was duplicated to minimize pipetting error. A standard protocol of initial denaturing at 95° C. for 10 min, 40 cycles of 95° C. for 10 sec, 60° C. for 30 sec, and 72° C. for 30 sec, followed by final extension at 72° C. for 5 min and melt curve analysis was applied on a BioRad CFX96 Real Time System (BioRad) coupled with Bio-Rad-CFX Manager software. The relative abundance of each transcript compared with the control was calculated utilizing the delta-Ct method.

The primer sequences used for RT-PCR were:

```
                                       (SEQ ID NO: 134)
    Mus-GAPDH-for: CATGGCCTTCCGTGTTCCTA (SEQ ID NO: 135)
    Mus-GAPDH-rev: GCGGCACGTCAGATCCA (SEQ ID NO: 136)
    Mus-Tsp1-for: CTTGAGGCAGATGAAGAAGACC (SEQ ID NO: 137)
    Mus-Tsp1-rev: ACTGACACCACTTGTTGCTTCC
```

Results:

Having determined that the 5-amino acid DWLPK (SEQ ID NO: 4) peptide derived from psap retains the Tsp-1 stimulating activity of the full-length psap both in vitro and in vivo, the Inventors sought to determine whether it also targeted BM-derived cells. As such, mice were treated with CM from LN4 cells alone, to simulate a systemic tumor-induced recruitment of BM-derived stromal cells in the lungs, or CM in combination with DWLPK peptide (SEQ ID NO: 4, psap peptide, FIG. 23). As expected, the recruitment of Gr1+ cells was identical regardless of the treatment. However, administration of the DWLPK (SEQ ID NO: 4) peptide stimulated Tsp-1 expression in the Gr1+ cells by more than two fold, while a peptide comprised of the same amino acids in a scrambled sequence failed to stimulate Tsp-1. Cells from the lung were then isolated and FACS sorted into three populations: CD45−, F4/80+, and Gr1+. RT-PCR analysis was performed on these populations to determine the level of Tsp-1 expression and it was found that Tsp-1 was expressed almost exclusively in the Gr1+ cell population.

Example 16: Weakly Metastatic Cell Conditioned-Medium can Upregulate Tsp-1 In Vivo Methods:

MDA-MB-231 and MDA-MB-LM2 cells were cultured in RPMI with 10% FBS. 5×106 cells were then subcultured in serum-free medium for 24 hours in order to generate conditioned media. Harvested media was centrifuged and filtered through 0.22 μM pore-size filters to remove any cells or cell debris.

Animals were euthanized at the end of experiments and lungs were quickly perfused by injecting 5 ml of cold PBS through the right ventricle of the heart. One part of the lung from each animal was fixed in 3.7% formalin and the other part was sorted by flow cytometry for either protein or RNA extraction.

For microscopy, following formalin fixation, tissues were cryoembedded in Tissue-Tek O.C.T. embedding compound (Electron Microscopy Sciences). Sections (30 μm) were washed 3 times in PBS and incubated in blocking/permeabilization buffer (PBS+2 mM EDTA, 1% BSA, 1% Goat Serum, 0.05% Triton X-100). Sections were then incubated with labeled primary antibodies against GR1 (Clone RB6-8C5, BD Pharmingen), CD11b (Clone M1/70, BD Pharmingen), Tsp-1 (Ab-4 Neomarkers), for 1 hour at room temperature. Primary antibodies were diluted in blocking/permeabilization buffer at a dilution of 1:100. After primary antibody incubation, sections were rinsed 5 times with PBS, counter-stained with DAPI and mounted in Prolong Gold-antifade reagent for epifluorescence microscopy analysis.

Figure 24:
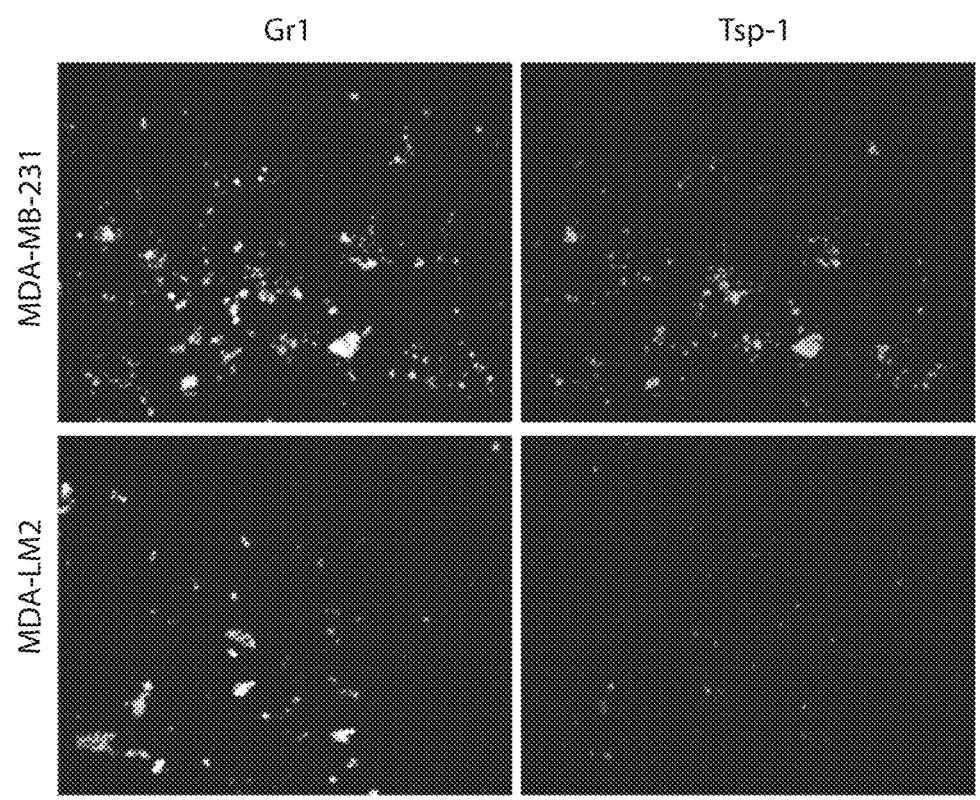
FIG. 24 is a series of photographs showing that mice injected with conditioned media from weakly metastatic MDA-MB-231 cells had increased Tsp-1 in lung tissue compared to mice injected with conditioned media from highly metastatic LM2 cells.

Results:

CM from weakly metastatic MDA breast cancer cells caused upregulation of Tsp-1 expression in BM recruited Gr1+ cells as compared with CM from highly metastatic LM2 breast cancer cells (FIG. 24).

Example 17: Further Peptide Data

Methods:

Mice were injected with DWLPK (SEQ ID NO: 4) or a scramble peptide using 5 day I.P. injections with 30 mg/kg peptide. White blood cells were isolated, protein was extracted, and a Western blot was performed measuring Tsp-1 protein.

Figure 25:
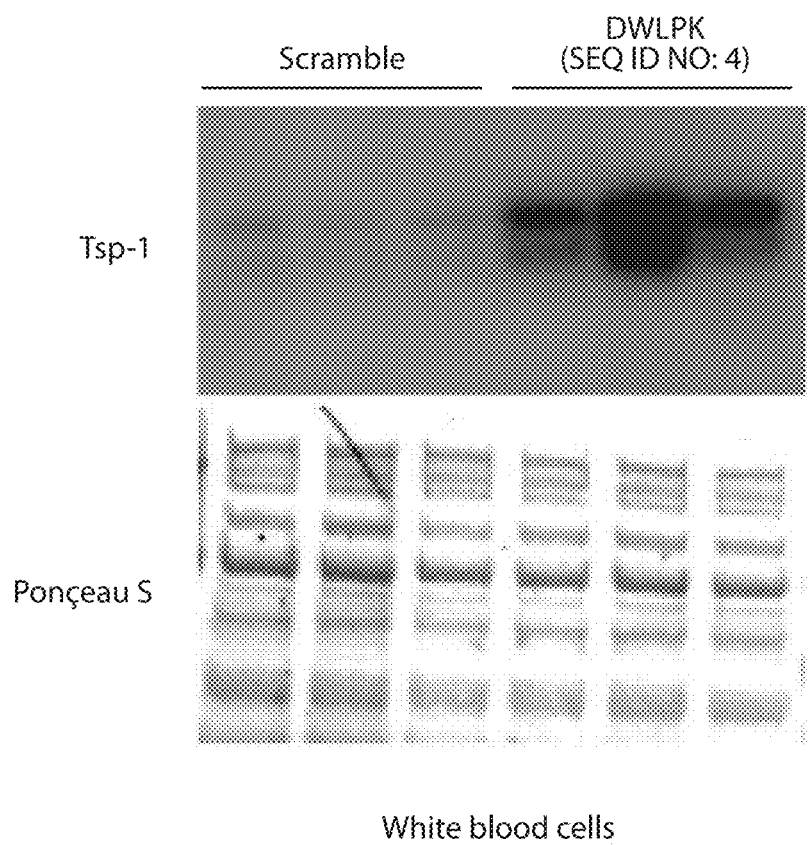
FIG. 25 shows a photograph of a Western blot and Ponceau S stain that demonstrates that DWLPK (SEQ ID NO: 4) increased Tsp-1 expression in white blood cells.

Results:

Tsp-1 was found to be upregulated in white blood cells isolated from mice injected with DWLPK (SEQ ID NO: 4) but not the scramble peptide (FIG. 25).

Example 18: Treatment of Other Angiogenesis-Dependent Diseases or Disorders

AMD: Lesions are created on a mouse's retina with a laser. The mice are then treated with a polypeptide as described herein, e.g., DWLPK (SEQ ID NO: 4) or Ac-dWIP-amide (SEQ ID NO: 132), or a scrambled peptide control. Treatment is either systemically (e.g., by intravenous or intraperitoneal injection) or by intravitreous injection. The rate of healing of the lesion is measured over time. It is expected that the lesion will heal faster in mice treated with the polypeptide than with the control.

Obesity: Ob/Ob mice are obtained (Jackson laboratory, Maine, #000632) and the heterozygous littermates are used as control mice. The mice are then treated with a polypeptide as described herein, e.g., DWLPK (SEQ ID NO: 4) or Ac-dWIP-amide (SEQ ID NO: 132), or a scrambled peptide control. Treatment is either by intravenous or intraperitoneal injection. Both polypeptide and control mice are fed the same diet. The weight of the animals is measured over time. It is expected that the Ob/Ob mice treated with the polypeptide will either lose weight or not gain weight as fast as Ob/Ob mice treated with the control peptide.

Crohn's Disease: An experimental model of Crohn's Disease (CD) is generated in mice by administering 0.1 mL of 2.5% TNBS (w/v) in 50% ethanol into the colon under light anesthesia. Control mice are given 0.1 mL of 50% ethanol. Beginning one day after TNBS administration, the mice are treated with Ac-dWIP-Amide (SEQ ID NO: 132) or control scramble peptide via intraperitoneal (i.p.) injection. A DSS-induced experimental model of CD is also generated by adding 3% dextran sodium sulfate (DSS) to the drinking water of mice. 7-8 days after the addition to the drinking water, the mice are treated with Ac-dWlP-Amide (SEQ ID NO: 132) or control scramble peptide via i.p. injection (Laroui, H., et al., Dextran sodium sulfate (DSS) induces colitis in mice by forming nano-lipocomplexes with medium-chain-length fatty acids in the colon. PLoS One, 2012. 7(3): p. e32084). Inflammation in a group of DSS and TNBS mice at the onset of treatment will be monitored macroscopically, histologically as known in the art (see, e.g., Laroui, H., et al., Dextran sodium sulfate (DSS) induces colitis in mice by forming nano-lipocomplexes with medium-chain-length fatty acids in the colon. PLoS One, 2012. 7(3): p. e32084 and Hollenbach, E., et al., Inhibition of RICK/nuclear factor-kappaB and p38 signaling attenuates the inflammatory response in a murine model of Crohn's disease. The Journal of biological chemistry, 2005. 280(15): p. 14981-8). It is expected that Crohn's disease mice treated with Ac-dWlP-Amide (SEQ ID NO: 132) will have reduced inflammation compared to Crohn's disease mice treated with a control scramble.

For all AMD, obesity, and Crohn's disease studies, a dose finding study is performed beginning with 100 µg/kg/day and increasing to 100 mg/kg/day in 10-fold increments. Previous experience indicates that 10 mg/kg/day is sufficient to induce Tsp-1 in the lungs of mice. Mice are treated for 5-7 days, or longer, depending on the disease. Tsp-1 expression is used as a read-out as well as disease-specific conditions (e.g., weight loss or inflammation). Urine and serum levels of Tsp-1 are also monitored as a readout for polypeptide activity.

For all AMD, obesity, and Crohn's disease studies, 20 animals/group are used, as determined by a statistical power analysis using an $1'2$ of 0.35 and a desired p-value of 0.05. All bivariate analyses, such as inflammation response, are conducted using Fisher's exact test. For analysis of other data sets ANOVA is used to determine significance.

The references cited herein and throughout the specification are incorporated herein by reference.

REFERENCES

1. Bendre, M. S., et al., (2002) Cancer Res 62, 5571-5579.
2. Brown, L. F., et al., (1999) Clinical Cancer Research 5:1041-1056.
3. Brummelkamp, T. R., et al., (2002) Science 296:550-553.
4. Bykov V J, and Wiman K G. (2003) Ann Med. 35(7): 458-65.
5. Campana W M, et al., (1996) Biochem Biophys Res Commun; 229(3): 706-712.
6. Campana W M, et al., (1998) FASEB J; 12(3): 307-314.
7. Campana W M, et al., (1999) Biochim Biophys Acta; 1427(3): 392-400.
8. Dameron, K. M., et al., (1994) Science 265:1582-1584.
9. Dong, J., et al., (2004) EMBO J; 23:2800-2810.
10. Ebba Brakenhielm, et al., (2004) Circulation Research; 94:1579
11. Elenbaas, B., et al., (2001) Genes Dev 15, 50-65.
12. Escot, C., et al., (1986) Proc Natl Acad Sci USA; 83:4834-4838.
13. Espinoza-Fonseca L M. (2005) Theor Biol Med Model. September 20; 2:38.
14. Gurova, K. V., et al., (2004) Cancer Res. 64:1951-1958.
15. Fidler, I. J. (2003). Nat Rev Cancer 3:453-458.
16. Folkman, J. (1971). N Engl J Med 285:1182-1186.
17. Fukumura, D., et al., (1998) Cell 94:715-725.
18. Grammas P, et al., (1999) Am. J. Path., 154(2):337-42
19. Gopalakrishnan, M. M., et al., (2004) Biochem J. November 1; 383(Pt 3): 507-515.
20. Hawighorst, T., et al., (2002). Oncogene 21, 7945-7956.
21. Healy D L, et al., (1998) Human Reproduction Update, 4:736-740.
22. Hiraiwa M, et al., (1997) Biochem Biophys Res Commun; 240(2): 415-418.
23. Hiraiwa M, et al., (1997) Proc Natl Acad Sci USA; 94(9): 4778-4781.
24. Ho C K and Li G. (2005) Br J Dermatol. November; 153(5):900-10.
25. Issaeva N, et al., (2004) Nat Med. 10(12):1321-8.
26. Janz, A., et al., (2000) Nucleic Acids Res 28:2268-2275.
27. Kalas, W., et al., (2005) Cancer Res 65:8878-8886.
28. Kang, Y., et al., (2003) Cancer Cell 3:537-549.
29. Kishimoto Y, et al., (1992) J Lipid Res; 33(9): 1255-1267.
30. Koch, A. E., (2000) Ann. Rheum. Dis.; 59(Suppl 1):i65-i71
31. Koochekpour S. Atlas Genet Cytogenet Oncol Haematol. March 2006.
32. Koochekpour S. Atlas Genet Cytogenet Oncol Haematol. September 2006
33. Kotani Y, et al., (1996) J Neurochem; 66(5): 2197-2200.
34. Littlewood, T. D., et al., (1995) Nucleic Acids Res 23, 1686-1690.
35. MacDougall, J. R., and Matrisian, L. M. (1995). Cancer Metastasis Rev 14:351-362.
36. Martins, C. P., et al., (2006). Cell 127:1323-1334.
37. Minn, A. J., et al., (2005) Nature 436:518-524.
38. Misasi R, et al., (2001) FASEB J; 15(2): 467-474.
39. Morales, C R. (1998), 51:156-166.
40. Morales, C R, (2003) Asian J Androl; 5(1): 57-63.
41. Muller, A., et al., (2001). Nature 410:50-56.
42. Nag, A., and Smith, R. G. (1989) Prostate 15:115-122.
43. Naumov, G. N., et al., (2002) Cancer Res 62:2162-2168.
44. Ngo, C. V., et al., (2000) Cell Growth Differ 11.
45. O'Brien J S, et al., (1994) Proc Natl Acad Sci USA; 91(20): 9593-9596.
46. O'Brien J S, et al., (1995) FASEB J; 9(8): 681-685.
47. Paget, S. (1889) Lancet 1:571-573.
48. Paleolog, E. M., (2002) Arthritis Res, 4(Suppl 3):581-590)
49. Pettaway, C. A., et al., (1996) Clinical Cancer Research 2:1627-1636.
50. Rehman Abdur, et al., Breast Cancer Research 2005, 7:R765-R774.
51. Roth, J., et al., (2003) Can. Res. 63: 3904-3908.
52. Schultheiss C, et al., (2006) Angiogenesis. 9(2):59-65.
53. Shing, Y. (1988). J Biol Chem 263:9059-9062.
54. Tanner S, Barberis A. (2004). J Negat Results Biomed. 3:5.
55. Tikhonenko, et al., (1996) J Biol. Chem. 271:30741-30747.
56. Vassilev, et al., (2004) Science 303:844-848.
57. Ventura, A., et al., (2007) Nature 445:661-665.
58. Vagnucci A H, Li W W, (2003) Lancet, 361(9357):605-8.
59. Watnick, R., et al., (2003) Cancer Cell 3.
60. Wiman, K. G., (2006) Cell Death and Differentiation 13:921-926.
61. Xue, W., et al., (2007) Nature 445:656-660.
62. Savagner, P., et al., (2004) Cell 117:927-939.

What is claimed:

1. An isolated peptide consisting of the amino acid sequence DWLP (SEQ ID NO: 5), wherein the peptide is acylated, carboxyamidated, pegylated, or conjugated to a polymer that enhances serum half-life of the peptide.

2. A chimeric peptide comprising at least a first portion and at least a second portion, wherein the first portion is the peptide of claim 1 and wherein the second portion is a non-Psap polypeptide.

3. The chimeric peptide of claim 2, wherein the second portion comprises an amino acid sequence or a polymer that enhances the serum half-life of said first portion.

4. The chimeric peptide of claim 3, wherein the second portion comprises an antibody Fc domain.

5. The chimeric peptide of claim 2, wherein the second portion comprises an antibody.

6. A composition comprising the peptide of claim 1 or a chimeric peptide of any one of claims 2-5, and a pharmaceutically acceptable carrier.

7. A method of inhibiting angiogenesis in a subject in need thereof, the method comprising administering to a subject in need thereof a therapeutically effective amount of a composition of claim 6.

8. The method of claim 7, wherein the subject in need thereof has an angiogenesis dependent disease or disorder.

9. The method of claim 7, wherein the subject has cancer.

10. A method of stimulating expression of Tsp-1 in a subject in need thereof, the method comprising administering to a subject in need thereof a therapeutically effective amount of a composition of claim 1.

11. The method of claim 10, wherein the subject in need thereof has an angiogenesis dependent disease or disorder.

12. The method of claim 10, wherein the subject has cancer.

13. A method of inhibiting growth and/or metastasis of cancer in a subject diagnosed with cancer, the method comprising administering to the subject a therapeutically effective amount of a composition of claim 1.

14. The method of claim 8, wherein the angiogenesis dependent disease or disorder is selected from a group consisting of cancer, psoriasis, age-related macular degeneration, thyroid hyperplasia, preeclampsia, rheumatoid arthritis and osteoarthritis, inflammatory bowel disease (IBD), Alzheimer's disease, obesity, pleural effusion, atherosclerosis, endometriosis, diabetic/other retinopathies, neovascular glaucoma, age-related macular degeneration, hemangiomas, and corneal neovascularization.

* * * * *

UNITED STATES PATENT AND TRADEMARK OFFICE
CERTIFICATE OF CORRECTION

PATENT NO. : 10,736,935 B2
APPLICATION NO. : 14/367577
DATED : August 11, 2020
INVENTOR(S) : Randolph S. Watnick Page 1 of 1

It is certified that error appears in the above-identified patent and that said Letters Patent is hereby corrected as shown below:

In the Claims

At Column 166, Line 38, Claim 10, delete "A method of stimulating expression of Tsp-1 in a subject in need thereof, the method comprising administering to a subject in need thereof a therapeutically effective amount of a composition of claim 1." and insert --A method of stimulating expression of Tsp-1 in a subject in need thereof, the method comprising administering to a subject in need thereof a therapeutically effective amount of a composition of claim 6.--

At Column 166, Line 47, Claim 13, delete "A method of inhibiting growth and/or metastasis of cancer in a subject diagnosed with cancer, the method comprising administering to the subject a therapeutically effective amount of a composition of claim 1" and insert --A method of inhibiting growth and/or metastasis of cancer in a subject diagnosed with cancer, the method comprising administering to the subject a therapeutically effective amount of a composition of claim 6.--

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 137

<210> SEQ ID NO 1
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1

Leu Gly Gly Gly Gly Ser Gly Gly Gly Gly Ser Ala
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 2

Ala Glu Ala Ala Ala Lys Glu Ala Ala Ala Lys Glu Ala
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 3

Cys Asp Trp Leu Pro Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Asp Trp Leu Pro Lys
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 5

Asp Trp Leu Pro
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 6

Asp Trp Ala Pro
1

```
<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Asp Tyr Leu Pro Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 8

Asp Trp Val Pro Lys
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 9

Asp Trp Leu Pro Arg
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 10

Asp Trp Ala Pro Lys
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 11

Asp Tyr Leu Pro
1

<210> SEQ ID NO 12
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 12

Asp Trp Leu Pro Lys Pro Asn Met Ser
1               5
```

```
<210> SEQ ID NO 13
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 13

Cys Asp Trp Leu Pro Lys Pro Asn Met
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 14

Thr Cys Asp Trp Leu Pro Lys Pro Asn
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 15

Lys Thr Cys Asp Trp Leu Pro Lys Pro
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 16

Glu Lys Thr Cys Asp Trp Leu Pro Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 17

Leu Glu Lys Thr Cys Asp Trp Leu Pro
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 18

Asp Trp Leu Pro Lys Pro Asn Met
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 19

Cys Asp Trp Leu Pro Lys Pro Asn
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 20

Thr Cys Asp Trp Leu Pro Lys Pro
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 21

Lys Thr Cys Asp Trp Leu Pro Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 22

Glu Lys Thr Cys Asp Trp Leu Pro
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 23

Asp Trp Leu Pro Lys Pro Asn
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 24

Cys Asp Trp Leu Pro Lys Pro
1               5

<210> SEQ ID NO 25
```

```
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 25

Thr Cys Asp Trp Leu Pro Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 26

Lys Thr Cys Asp Trp Leu Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 27

Asp Trp Leu Pro Lys Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 28

Thr Cys Asp Trp Leu Pro
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 29

Cys Asp Trp Leu Pro
1               5

<210> SEQ ID NO 30
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 30
ggcggcgtcg acatgtacgc cctcttcctc c                           31

<210> SEQ ID NO 31
<211> LENGTH: 32
<212> TYPE: DNA
```

```
<213> ORGANISM: Artificial Sequence
<220> FEATURE:
<223> OTHER INFORMATION: Synthetic Polynucleotide

<400> SEQUENCE: 31
ggcgcctcta gaagagactc gcagaggttg ag                                      32

<210> SEQ ID NO 32
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 32
ggcgcctcta gaacctcatc acagaaccc                                          29

<210> SEQ ID NO 33
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 33
ggcgcctcta gagccagagc agaggtgcag c                                       31

<210> SEQ ID NO 34
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 34

Ser Leu Pro Cys Asp Ile Cys Lys Asp Val Val Thr Ala Ala Gly Asp
1               5                   10                  15

Met Leu Lys Asp
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 35

Val Thr Ala Ala Gly Asp Met Leu Lys Asp Asn Ala Thr Glu Glu Glu
1               5                   10                  15

Ile Leu Val Tyr
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 36

Asn Ala Thr Glu Glu Glu Ile Leu Val Tyr Leu Glu Lys Thr Cys Asp
1               5                   10                  15

Trp Leu Pro Lys
            20
```

```
<210> SEQ ID NO 37
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 37

Leu Glu Lys Thr Cys Asp Trp Leu Pro Lys Pro Asn Met Ser Ala Ser
1               5                   10                  15

Cys Lys Glu Ile
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 38

Pro Asn Met Ser Ala Ser Cys Lys Glu Ile Val Asp Ser Tyr Leu Pro
1               5                   10                  15

Val Ile Leu Asp
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 39

Val Asp Ser Tyr Leu Pro Val Ile Leu Asp Ile Ile Lys Gly Glu Met
1               5                   10                  15

Ser Arg Pro Gly
            20

<210> SEQ ID NO 40
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 40

Ile Ile Lys Gly Glu Met Ser Arg Pro Gly Glu Val Cys Ser Ala Leu
1               5                   10                  15

Asn Leu Cys Glu Ser
            20

<210> SEQ ID NO 41
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 41

Cys Asp Trp Leu Pro Lys Pro Asn Met Ser Ala Ser Cys
1               5                   10
```

```
<210> SEQ ID NO 42
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 42

Leu Pro Lys Pro Asn Met
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 43

Asn Met Ser Ala Ser Cys
1               5

<210> SEQ ID NO 44
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 44

Cys Asp Trp Leu
1

<210> SEQ ID NO 45
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 45

Trp Leu Pro Lys
1

<210> SEQ ID NO 46
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: PEG2000

<400> SEQUENCE: 46

Xaa Cys Asp Trp Leu Pro Lys
1               5

<210> SEQ ID NO 47
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: PEG2000
```

<400> SEQUENCE: 47

Xaa Glu Lys Thr Cys Asp Trp Leu Pro Lys Pro Asn Met Ser Ala Ser
1               5                   10                  15

Cys Lys Glu

<210> SEQ ID NO 48
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 48

Asp Trp Ala Pro Ile Lys
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 49

Asp Trp Ala Pro Ile Pro Lys
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 50

Asp Trp Ala Pro Ile Pro Cys Lys
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 51

Asp Trp Ala Pro Ile Pro Cys Ser Lys
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 52

Asp Trp Ala Pro Ile Pro Cys Ala Lys
1               5

<210> SEQ ID NO 53
<211> LENGTH: 10
<212> TYPE: PRT
<213> ORGANISM: Artificial Sequence
<220> FEATURE:

```
<223> OTHER INFORMATION: Synthetic Polypeptide

<400> SEQUENCE: 53

Asp Trp Ala Pro Ile Pro Cys Ser Met Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 54

Asp Trp Ala Pro Ile Pro Cys Ser Leu Lys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 55

Asp Trp Ala Pro Ile Pro Cys Ala Ser Lys
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 56

Gln Pro Leu Arg His His Gln Asp Trp Ala Pro Asp
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 57

Arg Phe Asp Tyr Leu Pro Thr Glu Arg
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 58

Phe Val Phe Arg Phe Asp Tyr Leu Pro
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Polypeptide
```

```
<400> SEQUENCE: 59

Val Phe Arg Phe Asp Tyr Leu Pro Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 60

Asp Tyr Leu Pro Thr Glu Arg Glu Val
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 61

Phe Arg Phe Asp Tyr Leu Pro Thr Glu
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 62

Gln Gln Ser Asp Tyr Leu Pro Leu Thr
1               5

<210> SEQ ID NO 63
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 63

Phe Val Phe Arg Phe Asp Tyr Leu Pro Thr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 64

Phe Asp Tyr Leu Pro Thr Glu Arg Glu Val
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Polypeptide
```

```
<400> SEQUENCE: 65

Phe Arg Phe Asp Tyr Leu Pro Thr Glu Arg
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 66

Asp Tyr Leu Pro Thr Glu Arg Glu Val Ser
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 67

Arg Asp Tyr Leu Pro Tyr Tyr Pro Leu Asp
1               5                   10

<210> SEQ ID NO 68
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 68

Val Phe Arg Phe Asp Tyr Leu Pro Thr Glu Arg Glu Val Ser Val
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 69

Asn Trp Arg Phe Val Phe Arg Phe Asp Tyr Leu Pro Thr Glu Arg
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 70

Asn Phe Asn Trp Arg Phe Val Phe Arg Phe Asp Tyr Leu Pro Thr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 71
```

Arg Phe Asp Tyr Leu Pro Thr Glu Arg Glu Val Ser Val Trp Arg
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 72

Phe Asp Tyr Leu Pro Thr Glu Arg Glu Val Ser Val Trp Arg Arg
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 73

Arg Phe Val Phe Arg Phe Asp Tyr Leu Pro Thr Glu Arg Glu Val
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 74

Asn Phe Asn Trp Arg Phe Val Phe Arg Phe Asp Tyr Leu Pro Thr
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 75

Val Phe Arg Phe Asp Tyr Leu Pro Thr Glu Arg Glu Val Ser Val
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 76

Arg Phe Asp Tyr Leu Pro Thr Glu Arg Glu Val Ser Val Trp Arg
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 77

```
Trp Arg Phe Val Phe Arg Phe Asp Tyr Leu Pro Thr Glu Arg Glu
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 78

Phe Asp Tyr Leu Pro Thr Glu Arg Glu Val Ser Val Trp Arg Arg
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 79

Arg Phe Val Phe Arg Phe Asp Tyr Leu Pro Thr Glu Arg Glu Val
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 80

Arg Phe Asp Tyr Leu Pro Thr Glu Arg Glu Val Ser Val Trp Arg
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 81

Asn Phe Asn Trp Arg Phe Val Phe Arg Phe Asp Tyr Leu Pro Thr
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 82

Val Phe Arg Phe Asp Tyr Leu Pro Thr Glu Arg Glu Val Ser Val
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 83

Asn Trp Arg Phe Val Phe Arg Phe Asp Tyr Leu Pro Thr Glu Arg
```

```
1               5                   10                  15
```

<210> SEQ ID NO 84
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 84

```
Arg Phe Asp Tyr Leu Pro Thr Glu Arg Glu Val Ser Val Arg Arg
1               5                   10                  15
```

<210> SEQ ID NO 85
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 85

```
Phe Asp Tyr Leu Pro Thr Glu Arg Glu Val Ser Val Arg Arg Arg
1               5                   10                  15
```

<210> SEQ ID NO 86
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 86

```
Arg Phe Asp Tyr Leu Pro Thr Glu Arg Glu Val Ser Val Arg Arg
1               5                   10                  15
```

<210> SEQ ID NO 87
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 87

```
Phe Asp Tyr Leu Pro Thr Glu Arg Glu Val Ser Val Arg Arg Arg
1               5                   10                  15
```

<210> SEQ ID NO 88
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 88

```
Arg Phe Asp Tyr Leu Pro Thr Glu Arg Glu Val Ser Val Arg Arg
1               5                   10                  15
```

<210> SEQ ID NO 89
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 89

```
Val Phe Arg Phe Asp Tyr Leu Pro Thr Glu Arg Glu Val Ser Ile
1               5                   10                  15
```

<210> SEQ ID NO 90
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 90

Arg Phe Asp Tyr Leu Pro Thr Glu Arg Glu Val Ser Ile Trp Arg
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 91

Phe Asp Tyr Leu Pro Thr Glu Arg Glu Val Ser Ile Trp Arg Arg
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 92

Phe Asp Tyr Leu Pro Thr Glu Arg Glu Val Ser Ile Trp Arg Arg
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 93

Arg Phe Asp Tyr Leu Pro Thr Glu Arg Glu Val Ser Ile Trp Arg
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 94

Val Phe Arg Phe Asp Tyr Leu Pro Thr Glu Arg Glu Val Ser Ile
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 95

Arg Phe Asp Tyr Leu Pro Thr Glu Arg Glu Val Ser Ile Trp Arg
1               5                   10                  15

```
<210> SEQ ID NO 96
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 96

Phe Asp Tyr Leu Pro Thr Glu Arg Glu Val Ser Ile Trp Arg Arg
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 97

Arg Phe Asp Tyr Leu Pro Thr Glu Arg Glu Val Ser Ile Trp Arg
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 98

Val Phe Arg Phe Asp Tyr Leu Pro Thr Glu Arg Glu Val Ser Ile
1               5                   10                  15

<210> SEQ ID NO 99
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 99

Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Ile
                20                  25                  30

Trp Asn Thr Glu Asp Val Val Leu Asp Asp Glu Asn Pro Leu Thr Gly
            35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
                100                 105                 110

Glu Ala Glu Phe Arg Gln Pro Ala Val Leu Val Leu Gln Val Trp Asp
            115                 120                 125

Tyr Asp Arg Ile Ser Ala Asn Asp Phe Leu Gly Ser Leu Glu Leu Gln
    130                 135                 140

Leu Pro Asp Met Val Arg Gly Ala Arg Gly Pro Glu Leu Cys Ser Val
145                 150                 155                 160
```

-continued

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Ile Trp
        275                 280                 285

Arg Arg Tyr Trp Arg Thr Leu Val Leu Leu Leu Val Leu Leu Thr
    290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 100
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 100

Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Val Ile
                20                  25                  30

Trp Asn Thr Glu Asp Val Val Leu Asp Asp Glu Asn Pro Leu Thr Gly
            35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Arg Arg Ser Gly Pro Phe Ala Leu Glu
            100                 105                 110

Glu Ala Glu Phe Arg Gln Pro Ala Val Leu Val Leu Gln Val Trp Asp
    115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
            195                 200                 205

Lys Gln Arg Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Ile Trp
    275                 280                 285

Arg Arg Tyr Trp Arg Thr Leu Val Leu Leu Leu Val Leu Leu Thr
290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 101
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 101

Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Val Ile
            20                  25                  30

Trp Asn Thr Glu Asp Val Val Leu Asp Asp Glu Asn Pro Leu Thr Gly
        35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Ile Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
    130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
    210                 215                 220

```
Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
                260                 265                 270

Phe Asn Trp Phe Val Asn Pro Leu Lys Thr Phe Val Phe Ile Trp
                275                 280                 285

Arg Arg Tyr Trp Arg Thr Leu Val Leu Leu Leu Val Leu Leu Thr
                290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325
```

```
<210> SEQ ID NO 102
<211> LENGTH: 178
<212> TYPE: PRT
<213> ORGANISM: Artificial Sequence
<220> FEATURE:
<223> OTHER INFORMATION: Synthetic Polypeptide

<400> SEQUENCE: 102

Met Trp Ile Asp Ile Phe Pro Gln Asp Val Pro Ala Pro Pro Pro Val
1               5                   10                  15

Asp Ile Lys Pro Arg Gln Pro Ile Ser Tyr Glu Leu Arg Val Val Ile
                20                  25                  30

Trp Asn Thr Glu Asp Leu Val Leu Asp Asp Glu Asn Pro Leu Thr Gly
                35                  40                  45

Glu Met Ser Ser Asp Ile Tyr Val Lys Ser Trp Val Lys Gly Leu Glu
50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
                100                 105                 110

Glu Ala Glu Phe Arg Gln Pro Ala Val Leu Val Leu Gln Val Trp Asp
                115                 120                 125

Tyr Thr Ala Ser Leu Pro Met Thr Ser Leu Asp Pro Trp Ser Cys Ser
130                 135                 140

Tyr Gln Thr Trp Cys Val Gly Pro Gly Ala Pro Ser Ser Ala Leu Cys
145                 150                 155                 160

Ser Trp Pro Ala Met Gly Pro Gly Arg Gly Ala Ile Cys Phe Ala Ala
                165                 170                 175

Ala Ala
```

```
<210> SEQ ID NO 103
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 103

Met Trp Ile Asp Ile Phe Pro Gln Asp Val Pro Ala Pro Pro Pro Val
1               5                   10                  15
```

Asp Ile Lys Pro Arg Gln Pro Ile Ser Tyr Glu Leu Arg Val Val Ile
            20                  25                  30

Trp Asn Thr Glu Asp Val Val Leu Asp Asp Glu Asn Pro Leu Thr Gly
            35                  40                  45

Glu Met Ser Ser Asp Ile Tyr Val Lys Ser Trp Val Lys Gly Leu Glu
 50                  55                  60

His Asp Lys Gln Glu Thr Asp Val His Phe Asn Ser Leu Thr Gly Glu
 65                  70                  75                  80

Gly Asn Phe Asn Trp Arg Phe Val Phe Arg Phe Asp Tyr Leu Pro Thr
                 85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
            115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
            195                 200                 205

Lys Gln Arg Arg Arg Lys Gly Arg Pro Glu Asp Leu Glu Phe Thr Asp
210                 215                 220

Met Gly Gly Asn Val Tyr Ile Leu Thr Gly Lys Val Glu Ala Glu Phe
225                 230                 235                 240

Glu Leu Leu Thr Val Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Phe Ile Trp
            275                 280                 285

Arg Arg Tyr Trp Arg Thr Leu Val Leu Leu Leu Val Leu Leu Thr
            290                 295                 300

Val Phe Leu Leu Leu Val Phe Tyr Thr Ile Pro Gly Gln Ile Ser Gln
305                 310                 315                 320

Val Ile Phe Arg Pro Leu His Lys
            325

<210> SEQ ID NO 104
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 104

Met Trp Ile Asp Ile Phe Pro Gln Asp Val Pro Ala Pro Pro Val
 1               5                  10                  15

Asp Ile Lys Pro Arg Gln Pro Ile Ser Tyr Glu Leu Arg Val Val Ile
            20                  25                  30

Trp Asn Thr Glu Asp Val Val Leu Asp Asp Glu Asn Pro Leu Thr Gly
            35                  40                  45

```
Glu Met Ser Ser Asp Ile Tyr Val Lys Ser Trp Val Lys Gly Leu Glu
 50                  55                  60

His Asp Lys Gln Glu Thr Asp Val His Phe Asn Ser Leu Thr Gly Glu
 65                      70                  75                  80

Gly Asn Phe Asn Trp Arg Phe Val Phe Arg Phe Asp Tyr Leu Pro Thr
                     85                  90                  95

Glu Arg Glu Val Ser Val Trp Arg Arg Ser Gly Pro Phe Ala Leu Glu
                100                 105                 110

Glu Ala Glu Phe Arg Gln Pro Ala Val Leu Val Leu Gln Val Trp Asp
            115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Ile Trp
        275                 280                 285

Arg Arg Tyr Trp Arg Thr Leu Val Leu Leu Leu Val Leu Leu Thr
    290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 105
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 105

Met Trp Ile Asp Ile Phe Pro Gln Asp Val Pro Ala Pro Pro Pro Val
1               5                   10                  15

Asp Ile Lys Pro Arg Gln Pro Ile Ser Tyr Glu Leu Arg Val Val Ile
                20                  25                  30

Trp Asn Thr Glu Asp Val Val Leu Asp Glu Asn Pro Leu Thr Gly
            35                  40                  45

Glu Met Ser Ser Asp Ile Tyr Val Lys Ser Trp Val Lys Gly Leu Glu
        50                  55                  60

His Asp Lys Gln Glu Thr Asp Val His Phe Asn Ser Leu Thr Gly Glu
 65                 70                  75                  80
```

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
            115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
            195                 200                 205

Lys Gln Arg Arg Arg Lys Gly Arg Pro Glu Asp Leu Glu Phe Thr Asp
210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Gly Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Phe Ile Trp
            275                 280                 285

Arg Arg Tyr Trp Arg Thr Leu Val Leu Leu Leu Val Leu Leu Thr
290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 106
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 106

Met Trp Ile Asp Ile Phe Pro Gln Asp Val Pro Ala Pro Pro Pro Val
1               5                   10                  15

Asp Ile Lys Pro Arg Gln Pro Ile Ser Tyr Glu Leu Arg Val Val Ile
                20                  25                  30

Trp Asn Thr Glu Asp Val Val Leu Asp Asp Glu Asn Pro Leu Thr Gly
            35                  40                  45

Glu Met Ser Ser Asp Ile Tyr Val Lys Ser Trp Val Lys Gly Leu Glu
        50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
            100                 105                 110

```
Glu Ala Glu Phe Arg Gln Pro Ala Val Leu Val Leu Gln Val Trp Asp
            115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
            165                 170                 175

Arg Arg Leu Arg Gly Trp Trp Pro Val Lys Leu Lys Glu Ala Glu
            180                 185                 190

Asp Val Glu Arg Glu Ala Gln Glu Ala Gln Ala Gly Lys Lys Lys Arg
            195                 200                 205

Lys Gln Arg Arg Arg Lys Gly Arg Pro Glu Asp Leu Glu Phe Thr Asp
            210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
            245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Ile Trp
            275                 280                 285

Arg Arg Tyr Trp Arg Thr Leu Val Leu Leu Leu Val Leu Leu Thr
            290                 295                 300

Val Phe Leu Leu Leu Val Phe Tyr Thr Ile Pro Gly Gln Ile Ser Gln
305                 310                 315                 320

Val Ile Phe Arg Pro Leu His Lys
            325

<210> SEQ ID NO 107
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 107

Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Val Ile
            20                  25                  30

Trp Asn Thr Glu Asp Val Val Leu Asp Asp Glu Asn Pro Leu Thr Gly
            35                  40                  45

Glu Met Ser Ser Asp Ile Tyr Val Lys Ser Trp Val Lys Gly Leu Glu
50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Asp Tyr Leu Pro Thr
            85                  90                  95

Glu Arg Glu Val Ser Val Arg Arg Ser Gly Pro Phe Ala Leu Glu
            100                 105                 110

Glu Ala Glu Phe Arg Gln Pro Ala Val Leu Val Leu Gln Val Trp Asp
            115                 120                 125

Tyr Asp Arg Ile Ser Ala Asn Asp Phe Leu Gly Ser Leu Glu Leu Gln
130                 135                 140
```

```
Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Lys Gly Arg Pro Glu Asp Leu Glu Phe Thr Asp
        210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Phe Ile Trp
        275                 280                 285

Arg Arg Tyr Trp Arg Thr Leu Val Leu Leu Leu Val Leu Leu Thr
        290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 108
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 108

Met Trp Ile Asp Ile Phe Pro Gln Asp Val Pro Ala Pro Pro Pro Val
1               5                   10                  15

Asp Ile Lys Pro Arg Gln Pro Ile Ser Tyr Glu Leu Arg Val Val Ile
                20                  25                  30

Trp Asn Thr Glu Asp Val Val Leu Asp Glu Asn Pro Leu Thr Gly
            35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Ile Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175
```

```
Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Ile Trp
        275                 280                 285

Arg Arg Tyr Trp Arg Thr Leu Val Leu Leu Leu Val Leu Leu Thr
        290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 109
<211> LENGTH: 178
<212> TYPE: PRT
<213> ORGANISM: Artificial Sequence
<220> FEATURE:
<223> OTHER INFORMATION: Synthetic Polypeptide

<400> SEQUENCE: 109

Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Val Ile
            20                  25                  30

Trp Asn Thr Glu Asp Leu Val Leu Asp Asp Glu Asn Pro Leu Thr Gly
        35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Thr Ala Ser Leu Pro Met Thr Ser Leu Asp Pro Trp Ser Cys Ser
130                 135                 140

Tyr Gln Thr Trp Cys Val Gly Pro Gly Ala Pro Ser Ser Ala Leu Cys
                150                 155                 160
145

Ser Trp Pro Ala Met Gly Pro Gly Arg Gly Ala Ile Cys Phe Ala Ala
            165                 170                 175

Ala Ala

<210> SEQ ID NO 110
<211> LENGTH: 328
<212> TYPE: PRT
```

<213> ORGANISM: Artificial Sequence
<220> FEATURE:
<223> OTHER INFORMATION: Synthetic Polypeptide

<400> SEQUENCE: 110

```
Met Trp Ile Asp Ile Phe Pro Gln Asp Val Pro Ala Pro Pro Pro Val
1               5                  10                  15

Asp Ile Lys Pro Arg Gln Pro Ile Ser Tyr Glu Leu Arg Val Val Ile
            20                  25                  30

Trp Asn Thr Glu Asp Val Val Leu Asp Asp Glu Asn Pro Leu Thr Gly
        35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
    130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Phe Ile Trp
        275                 280                 285

Arg Arg Tyr Trp Arg Thr Leu Val Leu Leu Leu Val Leu Leu Thr
    290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325
```

<210> SEQ ID NO 111
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 111

```
Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Val Ile
            20                  25                  30

Trp Asn Thr Glu Asp Val Val Leu Asp Asp Glu Asn Pro Leu Thr Gly
            35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
    130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Phe Ile Trp
        275                 280                 285

Arg Arg Tyr Trp Arg Thr Leu Val Leu Leu Leu Val Leu Leu Thr
    290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 112
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 112

Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Val Ile
            20                  25                  30
```

```
Trp Asn Thr Glu Asp Val Val Leu Asp Asp Glu Asn Pro Leu Thr Gly
         35                  40                  45

Glu Met Ser Ser Asp Ile Tyr Val Lys Ser Trp Val Lys Gly Leu Glu
 50                  55                  60

His Asp Lys Gln Glu Thr Asp Val His Phe Asn Ser Leu Thr Gly Glu
 65                  70                  75                  80

Gly Asn Phe Asn Trp Arg Phe Val Phe Arg Phe Asp Tyr Leu Pro Thr
                 85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Phe Ile Trp
        275                 280                 285

Arg Arg Tyr Trp Arg Thr Leu Val Leu Leu Leu Val Leu Leu Thr
290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 113
<211> LENGTH: 322
<212> TYPE: PRT
<213> ORGANISM: Artificial Sequence
<220> FEATURE:
<223> OTHER INFORMATION: Synthetic Polypeptide

<400> SEQUENCE: 113

Met Trp Ile Asp Ile Phe Pro Gln Asp Val Pro Ala Pro Pro Pro Val
 1               5                  10                  15

Asp Ile Lys Pro Arg Gln Pro Ile Ser Tyr Glu Leu Arg Val Val Ile
             20                  25                  30

Trp Asn Thr Glu Asp Val Val Leu Asp Asp Glu Asn Pro Leu Thr Gly
         35                  40                  45

Glu Met Ser Ser Asp Ile Tyr Val Lys Ser Trp Val Lys Gly Leu Glu
 50                  55                  60
```

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
            85                  90                  95

Glu Arg Glu Val Ser Val Trp Arg Arg Ser Gly Pro Phe Ala Leu Glu
        100                 105                 110

Glu Ala Glu Phe Arg Gln Pro Ala Val Leu Val Leu Gln Val Trp Asp
    115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Ile Trp
275                 280                 285

Arg Arg Tyr Trp Arg Thr Leu Val Leu Leu Leu Val Leu Leu Thr
        290                 295                 300

Val Phe Leu Leu Leu Val Phe Tyr Thr Ile Pro Gly Gln Ile Ser Gln
305                 310                 315                 320

Val Ile

<210> SEQ ID NO 114
<211> LENGTH: 178
<212> TYPE: PRT
<213> ORGANISM: Artificial Sequence
<220> FEATURE:
<223> OTHER INFORMATION: Synthetic Polypeptide

<400> SEQUENCE: 114

Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Val Ile
            20                  25                  30

Trp Asn Thr Glu Asp Leu Val Leu Asp Glu Asn Pro Leu Thr Gly
        35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
            85                  90                  95

Glu Arg Glu Val Ser Val Trp Arg Arg Ser Gly Pro Phe Ala Leu Glu

```
                    100                 105                 110
Glu Ala Glu Phe Arg Gln Pro Ala Val Leu Val Leu Gln Val Trp Asp
                115                 120                 125

Tyr Thr Ala Ser Leu Pro Met Thr Ser Leu Asp Pro Trp Ser Cys Ser
            130                 135                 140

Tyr Gln Thr Trp Cys Val Gly Pro Gly Ala Pro Ser Ser Ala Leu Cys
145                 150                 155                 160

Ser Trp Pro Ala Met Gly Pro Gly Arg Gly Ala Ile Cys Phe Ala Ala
                165                 170                 175

Ala Ala

<210> SEQ ID NO 115
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 115

Met Trp Ile Asp Ile Phe Pro Gln Asp Val Pro Ala Pro Pro Pro Val
1               5                   10                  15

Asp Ile Lys Pro Arg Gln Pro Ile Ser Tyr Glu Leu Arg Val Val Ile
                20                  25                  30

Trp Asn Thr Glu Asp Val Val Leu Asp Asp Glu Asn Pro Leu Thr Gly
            35                  40                  45

Glu Met Ser Ser Asp Ile Tyr Val Lys Ser Trp Val Lys Gly Leu Glu
        50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Ile Trp
        275                 280                 285
```

```
Arg Arg Tyr Trp Arg Thr Leu Val Leu Leu Leu Val Leu Leu Thr
    290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 116
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 116

Met Trp Ile Asp Ile Phe Pro Gln Asp Val Pro Ala Pro Pro Val
1               5                   10                  15

Asp Ile Lys Pro Arg Gln Pro Ile Ser Tyr Glu Leu Arg Val Ile
            20                  25                  30

Trp Asn Thr Glu Asp Val Val Leu Asp Asp Glu Asn Pro Leu Thr Gly
        35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Ile Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Phe Ile Trp
        275                 280                 285

Arg Arg Tyr Trp Arg Thr Leu Val Leu Leu Leu Val Leu Leu Thr
    290                 295                 300

Val Phe Leu Leu Leu Val Phe Tyr Thr Ile Pro Gly Gln Ile Ser Gln
305                 310                 315                 320
```

Val Ile Phe Arg Pro Leu His Lys
                325

<210> SEQ ID NO 117
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 117

Met Trp Ile Asp Ile Phe Pro Gln Asp Val Pro Ala Pro Pro Pro Val
1               5                   10                  15

Asp Ile Lys Pro Arg Gln Pro Ile Ser Tyr Glu Leu Arg Val Val Ile
                20                  25                  30

Trp Asn Thr Glu Asp Val Val Leu Asp Glu Asn Pro Leu Thr Gly
            35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Ile Trp
        275                 280                 285

Arg Arg Tyr Trp Arg Thr Leu Val Leu Leu Leu Val Leu Leu Thr
    290                 295                 300

Val Phe Leu Leu Val Phe Tyr Thr Ile Pro Gly Gln Ile Ser Gln
305                 310                 315                 320

Val Ile Phe Arg Pro Leu His Lys
                325

<210> SEQ ID NO 118

<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 118

Met Trp Ile Asp Ile Phe Pro Gln Asp Val Pro Ala Pro Pro Pro Val
1               5                   10                  15

Asp Ile Lys Pro Arg Gln Pro Ile Ser Tyr Glu Leu Arg Val Val Ile
            20                  25                  30

Trp Asn Thr Glu Asp Val Val Leu Asp Asp Glu Asn Pro Leu Thr Gly
        35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Asp Arg Ile Ser Ala Asn Asp Phe Leu Gly Ser Leu Glu Leu Gln
    130                 135                 140

Leu Pro Asp Met Val Arg Gly Ala Arg Gly Pro Glu Leu Cys Ser Val
145                 150                 155                 160

Gln Leu Ala Arg Asn Gly Ala Gly Pro Arg Cys Asn Leu Phe Arg Cys
                165                 170                 175

Arg Arg Leu Arg Gly Trp Trp Pro Val Val Lys Leu Lys Glu Ala Glu
            180                 185                 190

Asp Val Glu Arg Glu Ala Gln Glu Ala Gln Ala Gly Lys Lys Lys Arg
        195                 200                 205

Lys Gln Arg Arg Arg Lys Gly Arg Pro Glu Asp Leu Glu Phe Thr Asp
    210                 215                 220

Met Gly Gly Asn Val Tyr Ile Leu Thr Gly Lys Val Glu Ala Glu Phe
225                 230                 235                 240

Glu Leu Leu Thr Val Glu Glu Ala Glu Lys Arg Pro Val Gly Lys Gly
                245                 250                 255

Arg Lys Gln Pro Glu Pro Leu Glu Lys Pro Ser Arg Pro Lys Thr Ser
            260                 265                 270

Phe Asn Trp Phe Val Asn Pro Leu Lys Thr Phe Val Phe Phe Ile Trp
        275                 280                 285

Arg Arg Tyr Trp Arg Thr Leu Val Leu Leu Leu Val Leu Leu Thr
    290                 295                 300

Val Phe Leu Leu Leu Val Phe Tyr Thr Ile Pro Gly Gln Ile Ser Gln
305                 310                 315                 320

Val Ile Phe Arg Pro Leu His Lys
                325

<210> SEQ ID NO 119
<211> LENGTH: 178
<212> TYPE: PRT
<213> ORGANISM: Artificial Sequence
<220> FEATURE:
<223> OTHER INFORMATION: Synthetic Polypeptide

<400> SEQUENCE: 119

```
Met Trp Ile Asp Ile Phe Pro Gln Asp Val Pro Ala Pro Pro Pro Val
1               5                   10                  15

Asp Ile Lys Pro Arg Gln Pro Ile Ser Tyr Glu Leu Arg Val Val Ile
            20                  25                  30

Trp Asn Thr Glu Asp Leu Val Leu Asp Asp Glu Asn Pro Leu Thr Gly
        35                  40                  45

Glu Met Ser Ser Asp Ile Tyr Val Lys Ser Trp Val Lys Gly Leu Glu
    50                  55                  60

His Asp Lys Gln Glu Thr Asp Val His Phe Asn Ser Leu Thr Gly Glu
65                  70                  75                  80

Gly Asn Phe Asn Trp Arg Phe Val Phe Arg Phe Asp Tyr Leu Pro Thr
                85                  90                  95

Glu Arg Glu Val Ser Val Trp Arg Arg Ser Gly Pro Phe Ala Leu Glu
            100                 105                 110

Glu Ala Glu Phe Arg Gln Pro Ala Val Leu Val Leu Gln Val Trp Asp
        115                 120                 125

Tyr Thr Ala Ser Leu Pro Met Thr Ser Leu Asp Pro Trp Ser Cys Ser
    130                 135                 140

Tyr Gln Thr Trp Cys Val Gly Pro Gly Ala Pro Ser Ser Ala Leu Cys
145                 150                 155                 160

Ser Trp Pro Ala Met Gly Pro Gly Arg Gly Ala Ile Cys Phe Ala Ala
                165                 170                 175

Ala Ala

<210> SEQ ID NO 120
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 120

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Arg Thr Thr
            20                  25                  30

Gly Glu Gly Val Gly Trp Val Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Lys Gln Val
65                  70                  75                  80

Val Leu Thr Met Thr Asn Val Asp Pro Ala Asp Thr Ala Thr Tyr Tyr
                85                  90                  95

Cys Thr His Glu Gln Tyr Tyr Tyr Asp Thr Ser Gly Gln Pro Tyr Tyr
            100                 105                 110

Phe Asp Phe Trp Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asn Ile Gln Val Thr Gln Ser Pro Ser Ser Leu Ser Ala Ser
145                 150                 155                 160

Val Gly Asp Arg Val Thr Met Thr Cys Arg Ala Ser Gln Asp Ile Arg
                165                 170                 175
```

```
Lys Asn Leu Asn Trp Tyr Gln Gln Lys Pro Gly Lys Ala Pro Lys Val
            180                 185                 190

Leu Ile Tyr Asp Ala Ser Asp Leu Glu Thr Gly Ile Pro Ser Arg Phe
        195                 200                 205

Ser Gly Ser Gly Ser Gly Thr Asp Phe Ile Leu Thr Ile Ser Ser Leu
210                 215                 220

Gln Pro Glu Asp Ile Ala Thr Tyr Tyr Cys Gln Gln Ser Asp Tyr Leu
225                 230                 235                 240

Pro Leu Thr Phe Gly Gly Gly Thr Lys Val Asp Ile Lys
                245                 250

<210> SEQ ID NO 121
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 121

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Arg Thr Thr
            20                  25                  30

Gly Glu Gly Val Gly Trp Val Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Lys Gln Val
65                  70                  75                  80

Val Leu Thr Met Thr Asn Val Asp Pro Ala Asp Thr Ala Thr Tyr Tyr
                85                  90                  95

Cys Thr His Glu Gln Tyr Tyr Asp Thr Ser Gly Gln Pro Tyr Tyr
            100                 105                 110

Phe Asp Phe Trp Gly Gln Gly Thr Leu Val Thr Val Ser Ser Gly Gly
        115                 120                 125

Gly Gly Ser Gly Gly Gly Gly Ser Gly Gly Gly Ser Gly Gly Gly
        130                 135                 140

Gly Ser Asn Ile Gln Val Thr Gln Ser Pro Ser Ser Leu Ser Ala Ser
145                 150                 155                 160

Val Gly Asp Arg Val Thr Met Thr Cys Arg Ala Ser Gln Asp Ile Arg
                165                 170                 175

Lys Asn Leu Asn Trp Tyr Gln Gln Lys Pro Gly Lys Ala Pro Lys Val
            180                 185                 190

Leu Ile Tyr Asp Ala Ser Asp Leu Glu Thr Gly Ile Pro Ser Arg Phe
        195                 200                 205

Ser Gly Ser Gly Ser Gly Thr Asp Phe Ile Leu Thr Ile Ser Ser Leu
210                 215                 220

Gln Pro Glu Asp Ile Ala Thr Tyr Tyr Cys Gln Gln Ser Asp Tyr Leu
225                 230                 235                 240

Pro Leu Thr Phe Gly Gly Gly Thr Lys Val Asp Ile Lys
                245                 250

<210> SEQ ID NO 122
<211> LENGTH: 107
<212> TYPE: PRT
<213> ORGANISM: Artificial Sequence
```

<220> FEATURE:
<223> OTHER INFORMATION: Synthetic Polypeptide

<400> SEQUENCE: 122

Asn Ile Gln Val Thr Gln Ser Pro Ser Ser Leu Ser Ala Ser Val Gly
1               5                   10                  15

Asp Arg Val Thr Met Thr Cys Arg Ala Ser Gln Asp Ile Arg Lys Asn
            20                  25                  30

Leu Asn Trp Tyr Gln Gln Lys Pro Gly Lys Ala Pro Lys Val Leu Ile
        35                  40                  45

Tyr Asp Ala Ser Asp Leu Glu Thr Gly Ile Pro Ser Arg Phe Ser Gly
50                  55                  60

Ser Gly Ser Gly Thr Asp Phe Ile Leu Thr Ile Ser Ser Leu Gln Pro
65                  70                  75                  80

Glu Asp Ile Ala Thr Tyr Tyr Cys Gln Gln Ser Asp Tyr Leu Pro Leu
                85                  90                  95

Thr Phe Gly Gly Gly Thr Lys Val Asp Ile Lys
            100                 105

<210> SEQ ID NO 123
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 123

Asn Ile Gln Val Thr Gln Ser Pro Ser Ser Leu Ser Ala Ser Val Gly
1               5                   10                  15

Asp Arg Val Thr Met Thr Cys Arg Ala Ser Gln Asp Ile Arg Lys Asn
            20                  25                  30

Leu Asn Trp Tyr Gln Gln Lys Pro Gly Lys Ala Pro Lys Val Leu Ile
        35                  40                  45

Tyr Asp Ala Ser Asp Leu Glu Thr Gly Ile Pro Ser Arg Phe Ser Gly
50                  55                  60

Ser Gly Ser Gly Thr Asp Phe Ile Leu Thr Ile Ser Ser Leu Gln Pro
65                  70                  75                  80

Glu Asp Ile Ala Thr Tyr Tyr Cys Gln Gln Ser Asp Tyr Leu Pro Leu
                85                  90                  95

Thr Phe Gly Gly Gly Thr Lys Val Asp Ile Lys
            100                 105

<210> SEQ ID NO 124
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 124

Ala Trp Leu Pro
1

<210> SEQ ID NO 125
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 125

```
Asp Ala Leu Pro
1

<210> SEQ ID NO 126
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 126

Asp Trp Leu Ala
1

<210> SEQ ID NO 127
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 127

Glu Trp Leu Pro Lys
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 128

Asp Trp Ile Pro Lys
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 129

Asp Trp Met Pro Lys
1               5

<210> SEQ ID NO 130
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (3)..(3)
<223> OTHER INFORMATION: D amino acid

<400> SEQUENCE: 130

Asp Trp Leu Pro
1

<210> SEQ ID NO 131
```

```
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (4)..(4)
<223> OTHER INFORMATION: D amino acid

<400> SEQUENCE: 131

Asp Trp Leu Pro
1

<210> SEQ ID NO 132
<211> LENGTH: 6
<212> TYPE: PRT
<213> ORGANISM: Artificial Sequence
<220> FEATURE:
<223> OTHER INFORMATION: Synthetic polynucleotide DWLP, with D amino
      acid substitued D and L, with N-terminal acetylation and C
      terminal amidation
<220> FEATURE:
<221> NAME/KEY: MISC_FEATURE
<222> LOCATION: (1)..(1)
<223> OTHER INFORMATION: N-terminal Acetyl group
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (6)..(6)
<223> OTHER INFORMATION: C-terminal Amide group

<400> SEQUENCE: 132

Xaa Asp Trp Leu Pro Xaa
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic polynucleotide with N-terminal acetyl
      group and C-terminal amide group
<220> FEATURE:
<221> NAME/KEY: MISC_FEATURE
<222> LOCATION: (1)..(1)
<223> OTHER INFORMATION: Acetyl group
<220> FEATURE:
<221> NAME/KEY: MISC_FEATURE
<222> LOCATION: (6)..(6)
<223> OTHER INFORMATION: Amide group

<400> SEQUENCE: 133

Xaa Asp Trp Leu Pro Xaa
1               5

<210> SEQ ID NO 134
<211> LENGTH: 20
<212> TYPE: DNA
<213> ORGANISM: Artificial Sequence
<220> FEATURE:
<223> OTHER INFORMATION: Synthetic polynucleotide
```

```
<400> SEQUENCE: 134
catggccttc cgtgttccta                                               20

<210> SEQ ID NO 135
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 135
gcggcacgtc agatcca                                                  17

<210> SEQ ID NO 136
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 136
cttgaggcag atgaagaaga cc                                            22

<210> SEQ ID NO 137
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 137
actgacacca cttgttgctt cc                                            22
```